US007365202B2

(12) United States Patent
Tan et al.

(10) Patent No.: US 7,365,202 B2
(45) Date of Patent: Apr. 29, 2008

(54) POLYMORPHS OF AN ANDROGEN RECEPTOR MODULATOR

(75) Inventors: Lushi Tan, Edison, NJ (US); Robert S. Meissner, Schwenksville, PA (US); Wenjie Li, Hopewell Junction, NY (US); James J. Perkins, Churchville, PA (US); Aaron S. Cote, West Windsor, NJ (US); Joyce Stellabott, Perkasie, PA (US); Yuan-Hon Kiang, Newbury Park, CA (US)

(73) Assignee: Merck & Co., Inc., Rahway, NJ (US)

( * ) Notice: Subject to any disclaimer, the term of this patent is extended or adjusted under 35 U.S.C. 154(b) by 0 days.

(21) Appl. No.: 11/633,152

(22) Filed: Dec. 4, 2006

(65) Prior Publication Data

US 2007/0129548 A1     Jun. 7, 2007

Related U.S. Application Data

(60) Provisional application No. 60/748,028, filed on Dec. 7, 2005.

(51) Int. Cl.
*C07D 221/18*   (2006.01)

(52) U.S. Cl. ....................................................... 546/77
(58) Field of Classification Search .................. 546/77, 546/61
See application file for complete search history.

(56) References Cited

U.S. PATENT DOCUMENTS

| 5,187,278 | A | 2/1993 | King et al. |
| 7,186,838 | B2 | 3/2007 | Meissner et al. |
| 2006/0252937 | A1 | 11/2006 | Tan et al. |

FOREIGN PATENT DOCUMENTS

| WO | WO-03077919 | * | 9/2003 |
| WO | WO2006/121655 | | 11/2006 |

OTHER PUBLICATIONS

Rasmusson G.H., et al. "Azasteroids: Structure Activity Relationships for Inhibition of 5 alpha-Reductase and of Androgen Receptor Binding", J. Med. Chem, vol. 29, pp. 2298-2315 (1986).
Brooks J.R., et al. "5 alpha-Reductase Inhibitory and Anti-Androgenic Activities of Some 4-Azasteroids in the Rat", Steroids, vol. 47, pp. 1-19 (1986).
U.S. Appl. No. 11/605090 filed Nov. 28, 2006, Meissner et al.

* cited by examiner

*Primary Examiner*—D. Margaret Seaman
*Assistant Examiner*—Nizal S. Chandrakumar
(74) *Attorney, Agent, or Firm*—Curtis C. Panzer; Patricia A. Shatynski; Valerie J. Camara

(57) ABSTRACT

Compounds of structural formula I are modulators of the androgen receptor (AR) in a tissue selective manner. These compounds are useful in the enhancement of weakened muscle tone and the treatment of conditions caused by androgen deficiency or which can be ameliorated by androgen administration, including osteoporosis, osteopenia, glucocorticoid-induced osteoporosis, periodontal disease, bone fracture, bone damage following bone reconstructive surgery, sarcopenia, frailty, aging skin, male hypogonadism, postmenopausal symptoms in women, atherosclerosis, hypercholesterolemia, hyperlipidemia, obesity, aplastic anemia and other hematopoietic disorders, inflammatory arthritis and joint repair, HIV-wasting, prostate cancer, benign prostatic hyperplasia (BPH), abdominal adiposity, metabolic syndrome, type II diabetes, cancer cachexia, Alzheimer's disease, muscular dystrophies, cognitive decline, sexual dysfunction, sleep apnea, depression, premature ovarian failure, and autoimmune disease, alone or in combination with other active agents.

31 Claims, 21 Drawing Sheets

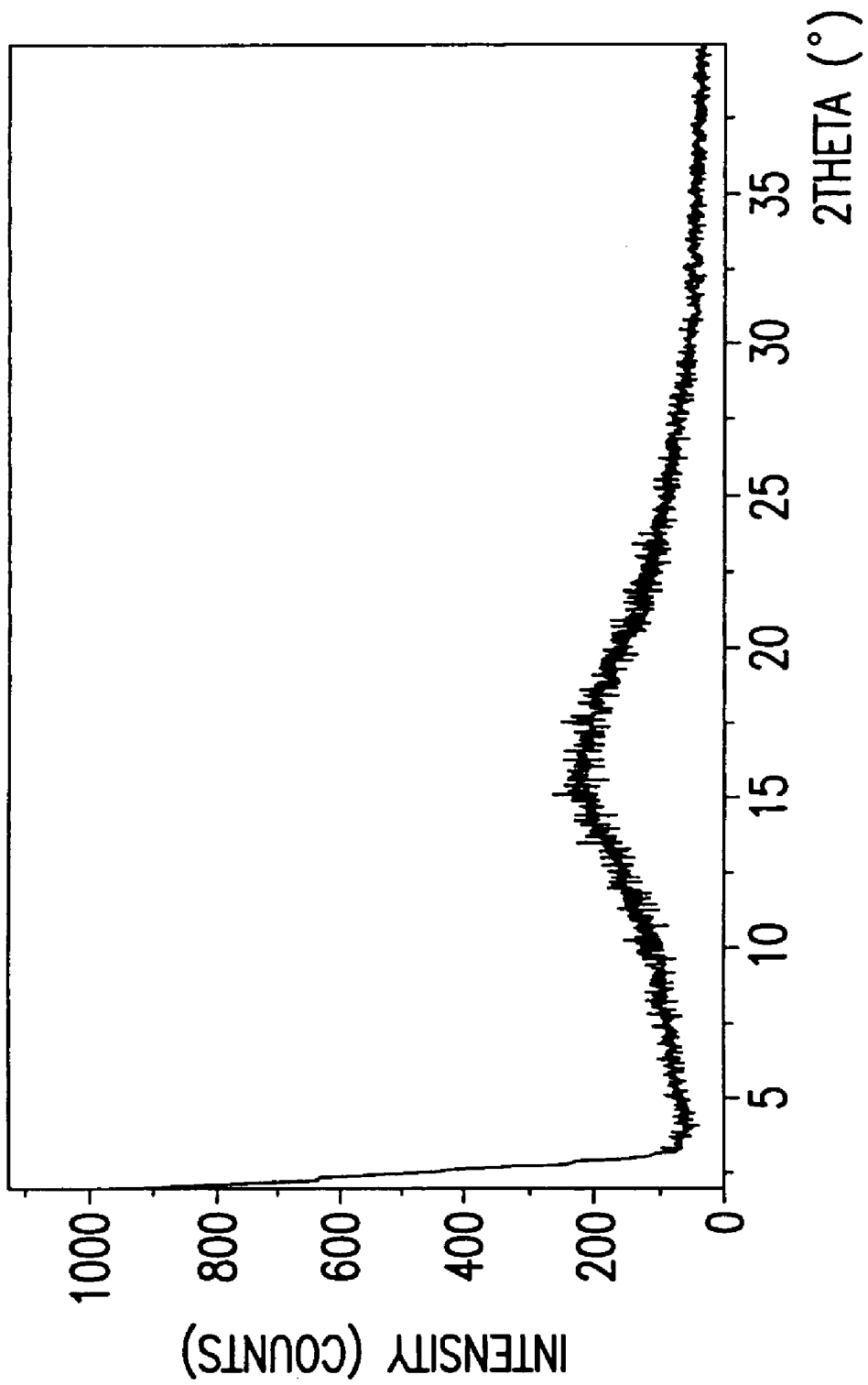

POLYMORPHS OF AN ANDROGEN RECEPTOR MODULATOR

RELATED APPLICATION DATA

This application claims priorty from U.S. Provisional Application Ser. No. 60/748,028, filed Dec. 7, 2005.

FIELD OF THE INVENTION

The present invention relates to crystalline and amorphous forms and solvates of N-(3H-imidazo[4,5-B]pyridin-2-ylmethyl)-2-fluoro-4-methyl-3-oxo-4-aza-5-alpha-androst-1-en-17-beta-carboxamide, a tissue-selective androgen receptor modulator (SARM). This SARM is thereby useful for the treatment of conditions caused by androgen deficiency or which can be ameliorated by androgen administration, such as osteoporosis, periodontal disease, bone fracture, frailty, and sarcopenia. Additionally, the SARM of the present invention can be used to treat mental disorders associated with low testosterone, such as depression, sexual dysfunction, and cognitive decline. The SARM, being an antagonist in specific tissues, may also useful in conditions where elevated androgen tone or activity causes symptoms, such as benign prostate hyperplasia and sleep apnea.

BACKGROUND OF THE INVENTION

The androgen receptor (AR) belongs to the superfamily of steroid/thyroid hormone nuclear receptors, whose other members include the estrogen receptor, the progesterone receptor, the glucocorticoid receptor, and the mineralocorticoid receptor. The AR is expressed in numerous tissues of the body and is the receptor through which the physiological as well as the pathophysiological effects of androgens, such as testosterone (T) and dihydrotestosterone (DHT), are mediated. Structurally, the AR is composed of three functional domains: the ligand binding domain (LBD), the DNA-binding domain, and amino-terminal domain. A compound that binds to the AR and mimics the effects of an endogenous AR ligand is referred to as an AR agonist, whereas a compound that inhibits the effects of an endogenous AR ligand is termed an AR antagonist.

Androgen ligand binding to the AR induces a ligand/receptor complex, which, after translocation into the nucleus of the cell, binds to regulatory DNA sequences (referred to as androgen response elements) within the promoter or enhancer regions of the target genes present in the nucleus. Other proteins termed cofactors are next recruited, which bind to the receptor leading to gene transcription.

Androgen therapy has been to treat a variety of male disorders such as reproductive disorders and primary or secondary male hypogonadism. Moreover, a number of natural or synthetic AR agonists have been investigated for the treatment of musculoskeletal disorders, such as bone disease, hematopoietic disorders, neuromuscular disease, rheumatological disease, wasting disease, and for hormone replacement therapy (HRT), such as female androgen deficiency. In addition, AR antagonists, such as flutamide and bicalutamide, are used to treat prostate cancer. It would therefore be useful to have available compounds that can activate ("agonize") the function of the AR in a tissue-selective manner that would produce the desired osteo- and myoanabolic effects of androgens without the negative androgenic properties, such as virilization and repression of high density lipoprotein cholesterol (HDL).

The beneficial effects of androgens on bone in postmenopausal osteoporosis were documented in recent studies using combined testosterone and estrogen administration [Hofbauer, et al., *Eur. J. Edocrinol.* 140: 271-286 (1999)]. In a large 2-year, double-blind comparison study, oral conjugated estrogen (CEE) and methyltestosterone combinations were demonstrated to be effective in promoting accrual of bone mass in the spine and hip, while conjugated estrogen therapy alone prevented bone loss [*J. Reprod. Med.*, 44: 1012-1020 (1999)].

Additionally, there is evidence that hot flushes decrease in women treated with CEE and methyltestosterone; however, 30% of the treated women suffered from significant increases in acne and facial hair, a complication of all current androgen pharmacotherapies [Watts, et al., *Obstet. Gynecol.*, 85: 529-537 (1995)]. It was also found that the addition of methyltestosterone to CEE decreased HDL levels, as seen in other studies. Thus, the virilizing potential and effects on lipid profile of current androgen therapies provide a rationale for developing tissue-selective androgen receptor agonists.

Androgens play an important role in bone metabolism in men [Anderson, et al., "Androgen supplementation in eugonadal men with osteoporosis—effects of six months of treatment on bone mineral density and cardiovascular risk factors," *Bone*, 18: 171-177 (1996)]. Even in eugonadal men with osteoporosis, the therapeutic response to testosterone treatment reveals that androgens exert important osteoanabolic effects. Mean lumbar BMD increased from 0.799 gm/cm2 to 0.839 g/cm2, in 5 to 6 months in response to 250 mg of testosterone ester administered intramuscularly. SARMs can thus be used to treat osteoporosis in men.

Androgen deficiency occurs in men with stage D prostate cancer (metastatic) who undergo androgen deprivation therapy (ADT). Endocrine orchiectomy is achieved by long acting GnRH agonists, while androgen receptor blockade is implemented with AR antagonists. In response to hormonal deprivation, these men suffered from hot flushes, significant bone loss, weakness, and fatigue. In a pilot study of men with stage D prostate cancer, osteopenia (50% vs. 38%) and osteoporosis (38% vs. 25%) were more common in men who had undergone ADT for greater than one year than the patients who did not undergo ADT [Wei, et al., *Urology*, 54: 607-611 (1999)]. Lumbar spine BMD was significantly lower in men who had undergone ADT. Thus tissue selective AR antagonists in the prostate that lack antagonistic action in bone and muscle can be useful agents for the treatment of prostate cancer, either alone or as an adjunct to traditional ADT [See also A. Stoch, et al., *J. Clin. Endocrin. Metab.*, 86: 2787-2791 (2001)].

Tissue-selective AR antagonists can also treat polycystic ovarian syndrome in postmenopausal women. See C. A. Eagleson, et al., "Polycystic ovarian syndrome: evidence that flutamide restores sensitivity of the gonadotropin-releasing hormone pulse generator to inhibition by estradiol and progesterone," *J. Clin. Endocrinol. Metab.*, 85: 4047-4052 (2000).

SARMs can also treat certain hematopoietic disorders as androgens stimulate renal hypertrophy and erythropoietin (EPO) production. Prior to the introduction of recombinant human EPO, androgens were employed to treat anemia caused by chronic renal failure. In addition, androgens increase serum EPO levels in anemic patients with non-severe aplastic anemia and myelodysplastic syndromes. Treatment for anemia will require selective action such as can be provided by SARMs.

SARMs can also have clinical value as an adjunct to the treatment of obesity. This approach to lowering body fat is supported by published observations that androgen administration reduced subcutaneous and visceral fat in obese patients [J. C. Lovejoy, et al., "Oral anabolic steroid treatment, but not parenteral androgen treatment, decreases abdominal fat in obese, older men," *Int. J. Obesity*, 19: 614-624 (1995)], [J. C. Lovejoy, et al., "Exogenous Androgens Influence Body Composition and Regional Body Fat Distribution in Obese Postmenopausal Women—A Clinical Research Center Study," *J. Clin. Endocrinol. Metab.*, 81: 2198-2203 (1996)]. Therefore, SARMs devoid of unwanted androgenic effects can be beneficial in the treatment of obesity.

Androgen receptor agonists can also have therapeutic value against metabolic syndrome (insulin resistance syndrome, syndrome X), particularly in men. Low levels of total and free testosterone and sex hormone-binding globulin (SHBG) in men have been associated with type 2 diabetes, visceral obesity, insulin resistance (hyperinsulinemia, dyslipidemia) and metabolic syndrome. D. Laaksonen, et al., *Diabetes Care*, 27 (5): 1036-1041(2004); see also D. Laaksonen, et al. *Euro. J Endocrin*, 149: 601-608 (2003); P. Márin, et al. *Int. J. Obesity*, 16: 991-997 (1992), and P. Márin, et al. *Obesity Res.*, 1(4): 245-251 (1993).

Androgen receptor agonists can also have therapeutic value against neurodegenerative diseases such as Alzheimer's disease (AD). The ability of androgens to induce neuroprotection through the androgen receptor was reported by J. Hammond, et al., "Testosterone-mediated neuroprotection through the androgen receptor in human primary neurons," *J. Neurochem.*, 77: 1319-1326 (2001). Gouras et al. reported that testosterone reduces secretion of Alzheimer's β-amyloid peptides and can therefore be used in the treatment of AD [(*Proc. Nat. Acad. Sci.*, 97: 1202-1205 (2000)]. A mechanism via inhibition of hyperphosphorylation of proteins implicated in the progression AD has also been described [S. Papasozomenos, "Testosterone prevents the heat shock-induced over activation of glycogen synthase kinase-3β but not of cyclin-dependent kinase 5 and c-Jun NH2-terminal kinase and concomitantly abolishes hyperphosphorylation of τ: Implications for Alzheimer's disease," *Proc. Nat. Acad. Sci.*, 99: 1140-1145 (2002)].

Androgen receptor agonists can also have a beneficial effect on muscle tone and strength. Recent studies have demonstrated that "physiologic androgen replacement in healthy, hypogonadal men is associated with significant gains in fat-free mass, muscle size and maximal voluntary strength," [S. Bhasin, et al., *J. Endocrin.*, 170: 27-38 (2001)].

Androgen receptor modulators can be useful in treating decreased libido in both men and women. Androgen deficiency in men is related to diminished libido. S. Howell et al., *Br. J. Cancer*, 82: 158-161. Low androgen levels contribute to the decline in sexual interest in many women during their later reproductive years. S. Davis, *J. Clin. Endocrinol. Metab.*, 84: 1886-1891 (1999). In one study, circulating free testosterone was positively correlated with sexual desire. Id. In another study, women with primary or secondary adrenal insufficiency were provided physiological DHEA replacement (50 mg/day). Compared with women taking placebo, DHEA-administered women showed an increase in the frequency of sexual thoughts, interest, and satisfaction. W. Arlt, et al., *N Engl. J. Med.* 341:1013-1020 (1999), see also, K. Miller, *J. Clin. Endocrinol. Metab.*, 86: 2395-2401 (2001).

Additionally, androgen receptor modulators may also be useful in treating cognitive impairment. In a recent study, high-dose oral estrogen either alone or in combination with high-dose oral methyltestosterone was given to postmenopausal women for a four-month period. Cognitive tests were administered before and after the four-month hormone treatment. The investigation found that women receiving a combination of estrogen (1.25 mg) and methyltestosterone (2.50 mg) maintained a steady level of performance on the Building Memory task, but the women receiving estrogen (1.25 mg) alone exhibited decreased performance. A. Wisniewski, *Horm. Res.* 58:150-155 (2002).

N-(3H-imidazo[4,5-b]pyridin-2-ylmethyl)-2-fluoro-4-methyl-3-oxo4-aza-5-alpha-androst-1-en-17-beta-carboxamide has the following structural formula:

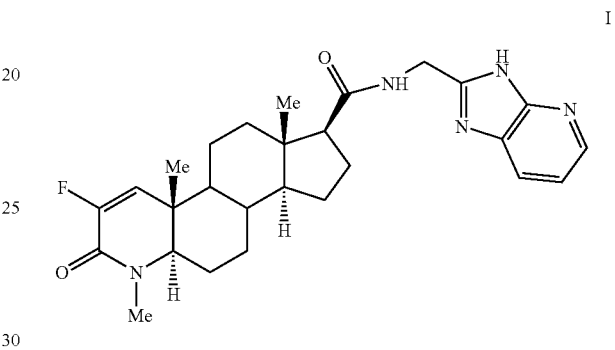

This compound has been previously disclosed in the international application, WO03/077919, published on Sep. 25, 2003.

SUMMARY OF THE INVENTION

The present invention relates to crystalline polymorphic, pseudopolymorphic and amorphous solid state forms of N-(3H-imidazo[4,5-b]pyridin-2-ylmethyl)-2-fluoro-4-methyl-3-oxo-4-aza-5-alpha-androst-1-en-17-beta-carboxamide its use, and pharmaceutical compositions. The present invention additionally provides processes for the preparation of amorphous and crystalline solid state forms of N-(3H-imidazo[4,5-b]pyridin-2-ylmethyl)-2 fluoro-4-methyl-3-oxo4-aza-5-alpha-androst-1-en-17-beta-carboxamide.

Knowledge of various physicochemical properties of an active material is important to optimize utility of that material in all aspects of a compound's life cycle including, for example, its manufacture and pharmaceutical processing, and/or its storage, shipping and therapeutic uses. Sometimes a pharmacologically active compound can not be fashioned into a suitable pharmaceutical compositon because the active compound has unfavorable physical properties such as, for example, poor milling properties or poor dissolution properties.

One aspect of the present invention provides crystalline polymorphic and pseudopolymorphic and amorphous solid state forms of N-(3H-imidazo[4,5-b]pyridin-2-ylmethyl)-2-fluoro-4-methyl-3-oxo-4-aza-5-alpha-androst-1-en-17-beta-carboxamide. The amorphous and crystalline solid forms of the present invention have good physiochemical properties; desirable stability characteristics; desirable medicinal properties; and good processing properties. The crystalline and amorphous solid state forms of the present invention can be incorporated into a variety of different formulation vehicles making them particularly suitable for pharmaceutical utility.

The solid state forms of the compound of formula I are effective as an androgen receptor agonist and are particularly effective as SARMs. The polymorphic, pseudopolymorphic and amorphous solid state forms of the present invention are, therefore useful for the treatment of conditions caused by androgen deficiency or which can be ameliorated by androgen administration.

BRIEF DESCRIPTION OF THE FIGURES

FIG. 21 is a XRPD of the amorphous form of compound I.

DETAILED DESCRIPTION OF THE INVENTION

Figure 1:
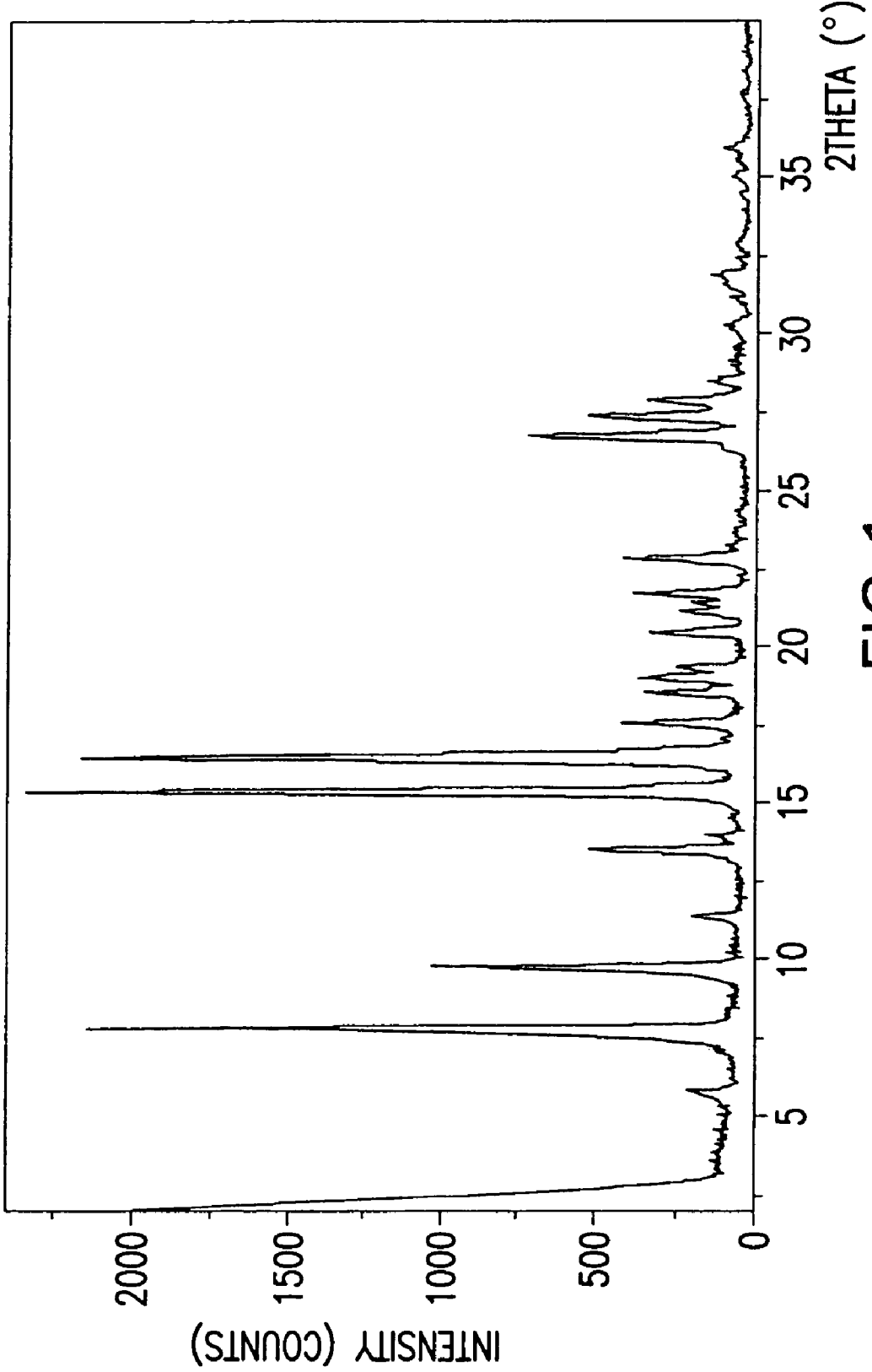
FIG. 1 is a characteristic X-ray diffraction pattern of the anhydrous crystalline form A of compound I.

The present invention provides polymorphic and pseudopolymorphic forms including crystalline, solvates, hydrates, and anhydrates, as well as amorphous solid state forms, of N-(3H-imidazo[4,5-b]pyridin-2-ylmethyl)-2-fluoro-4-methyl-3-oxo-4-aza-5-alpha-androst-1-en-17-beta-carboxamide having structural formula:

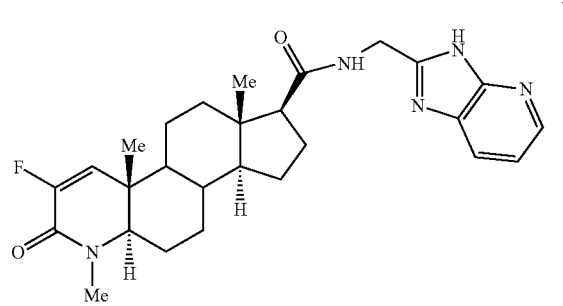

The present invention also relates to pharmaceutical compositions comprising solid state forms of the compound of the present invention and a pharmaceutically acceptable carrier.

Polymorphs are two or more crystalline phases of the same chemical compound that possess different arrangement and/or conformation of the molecules in a crystal lattice. Different polymorphs of an active pharmaceutical compound can exhibit different physical and chemical properties. Different physical and chemical properties of a given active pharmaceutical compound can also depend on moisture/solvent content. Pseudopolymorphs include hydrates and solvates of a compound. Pseudopolymorphs incorporate one or more solvents or water into the crystal lattice of the compound.

The solid state physical properties of a compound can be influenced by controlling the conditions under which the compounds are obtained in solid form. Different crystal structures of a compound may exhibit variations in physical and chemical properties such as color, stability, processability, dissolution and even bioavailability. For example, flowability, which affects how particles flow past each other, is one such solid state physical property that can affect how a compound is milled. To compensate for poor flowability and obtain a millable pharmaceutical tablet, often times a pharmaceutical formulator must add other agents to a pharmaceutical compositon such as talc or starch, to act as glidants or lubricants. It would be beneficial to minimize use of such agents by choosing a solid form of an active ingredient that exhibits favorable flowability and milling properties.

Another solid state physical property of a compound is the rate of dissolution in a fluid, such as water. The dissolution of an active ingredient may affect the storage stability of a pharmaceutical product. Additionally, the dissolution rate of an active ingredient affects the rate at which an orally-administered active ingredient can reach a subject's bloodstream. Choice of a suitable solid form can maximize the storage stability and/or the dissolution rate of an active ingredient.

Additionally, identification, manufacture, and control of specific solid state forms are of interest to the pharmaceutical industry during clinical trials or other research studies. If a given polymorphic form of a drug is not held constant during clinical studies, the exact dosage form being studied may not be comparable from one lot to another introducing a uncontrolled source of error to the study.

Generally, it is difficult to predict whether or not a given compound will form various crystalline solid state forms. It is even more difficult to predict the structural configurations and the physical properties of these different crystalline solid state forms.

It would be advantageous to identify and utilize the various polymorphs, pseudopolymorphs, and amorphous forms of a pharmaceutically active compound in order to create an arsenal of solid forms with varying physical properties. In this manner, a pharmaceutical dosage form can be designed with a specific desirable property, such as for example, a specific dissolution rate, milling property, thermal stability or shelf-life.

One embodiment of the invention is a crystalline solid form A free base of N-(3H-imidazo[4,5-b]pyridin-2-ylmethyl)-2-fluoro-4-methyl-3-oxo-4-aza-5-alpha-androst-1-en-17-beta-carboxamide having a X-ray powder diffraction (XRPD) pattern with characteristic diffraction peaks corresponding 2-theta values of 5.6±0.1, 7.6±0.1, and 9.6±0.1. The anhydrous crystalline form A is further characterized by the additional diffraction peaks at 2-theta values of 11.2±0.1, 13.4±0.1, and 15.2±0.1. The anhydrous crystalline form A is still further characterized by diffraction peaks at 2-theta values of 16.3±0.1 and 17.3±0.1.

Figure 2:
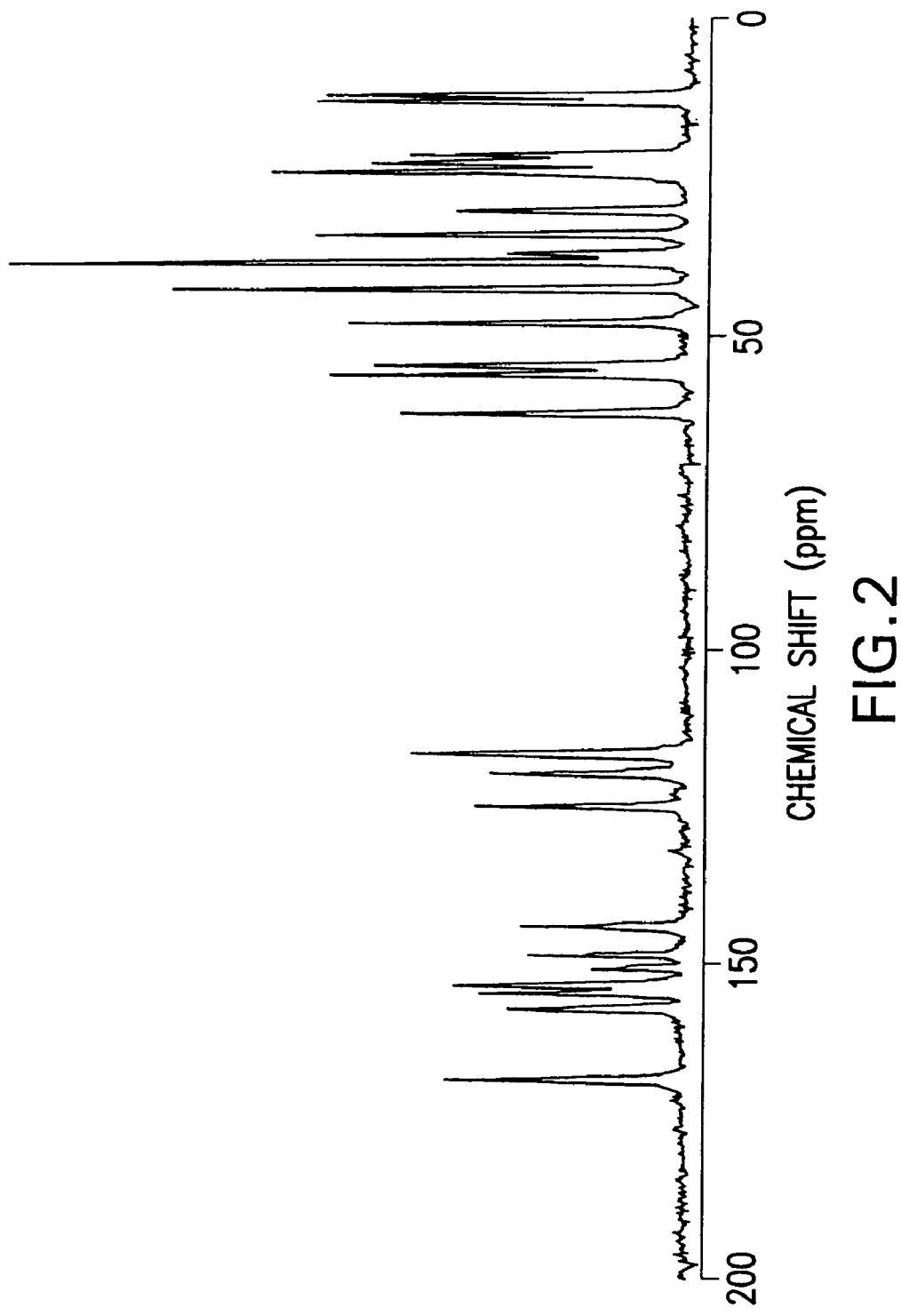
FIG. 2 is a carbon-13 cross-polarization magic-angle spinning (CPMAS) nuclear magnetic resonance (NMR) spectrum of the anhydrous crystalline Form A of compound I.

The anhydrous crystalline solid state Form A free base of compound of formula I exhibits a solid-state carbon-13 cross-polarization magic-angle spinning (CPMAS) nuclear magnetic resonance (NMR) spectrum (carbon-13 CPMAS NMR) spectrum having characteristic signals with chemical shift values of 39.7, 118.3, 169.2, and 12.6±0.1 p.p.m. The crystalline solid Form A is further characterized as having signals with chemical shift values of 44.0, 121.4, 158.2, and 13.7±0.1 p.p.m. An even further characteristic of the anhydrous crystalline Form A of compound I exhibits signals with chemical shift values of 49.5, 145.4, 126.5, and 25.0±0.1 p.p.m. FIG. 2 shows a solid-state carbon-13 CPMAS NMR spectrum for the anhydrous crystalline Form A of the compound of formula 1.

Figure 3:
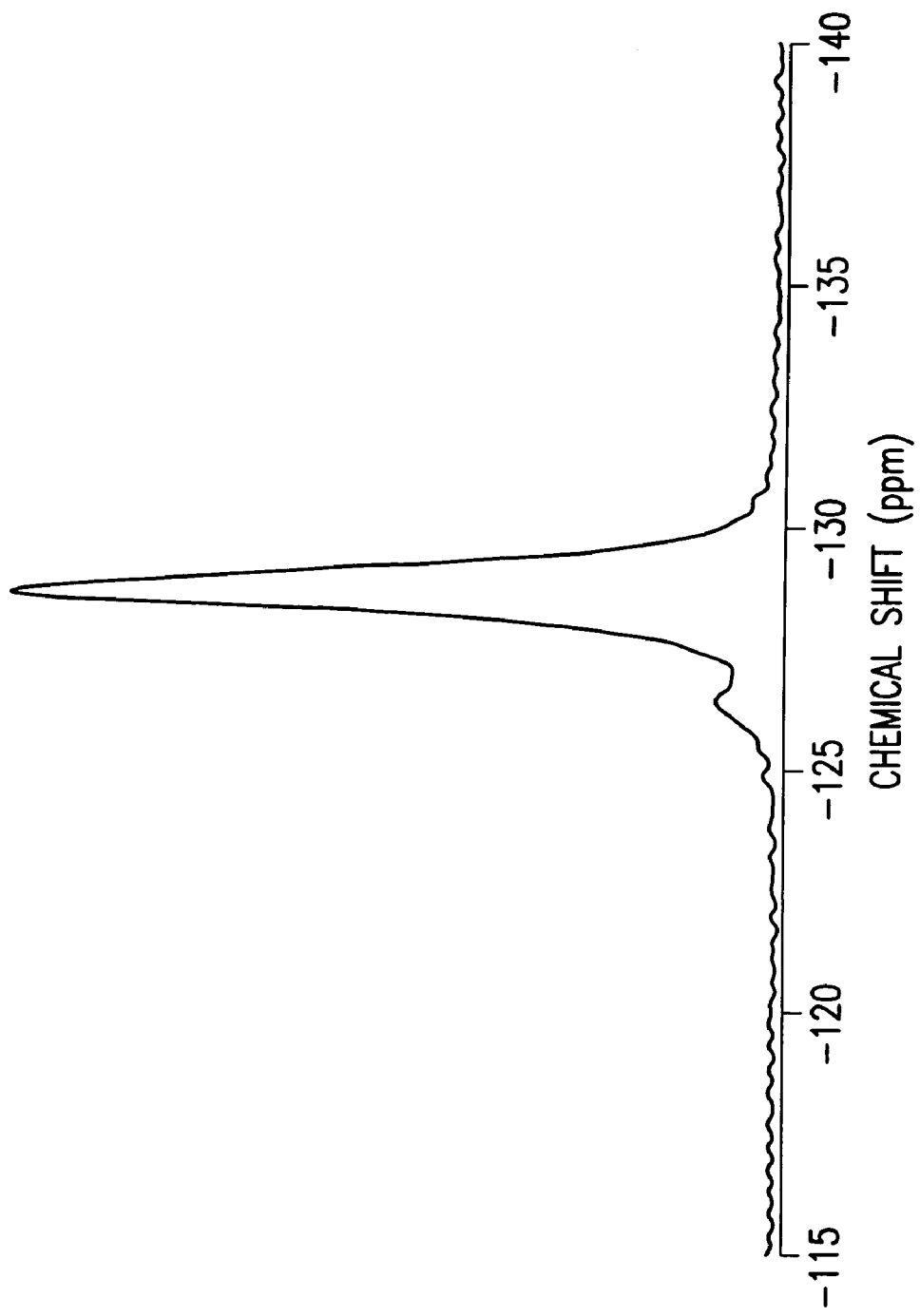
FIG. 3 is a fluorine-19 cross-polarization magic-angle spinning (CPMAS) nuclear magnetic resonance (NMR) spectrum of the anhydrous crystalline Form A of compound I.

In yet another embodiment, the solid-state fluorine-19 cross-polarization magic-angle spinning (CPMAS) nuclear magnetic resonance (NMR) spectrum for the anhydrous crystalline Form A of compound I is shown in FIG. 3. The anhydrous crystalline solid state form exhibits a characteristic signal with chemical shift value of −128.9±0.1 p.p.m.

Figure 4:
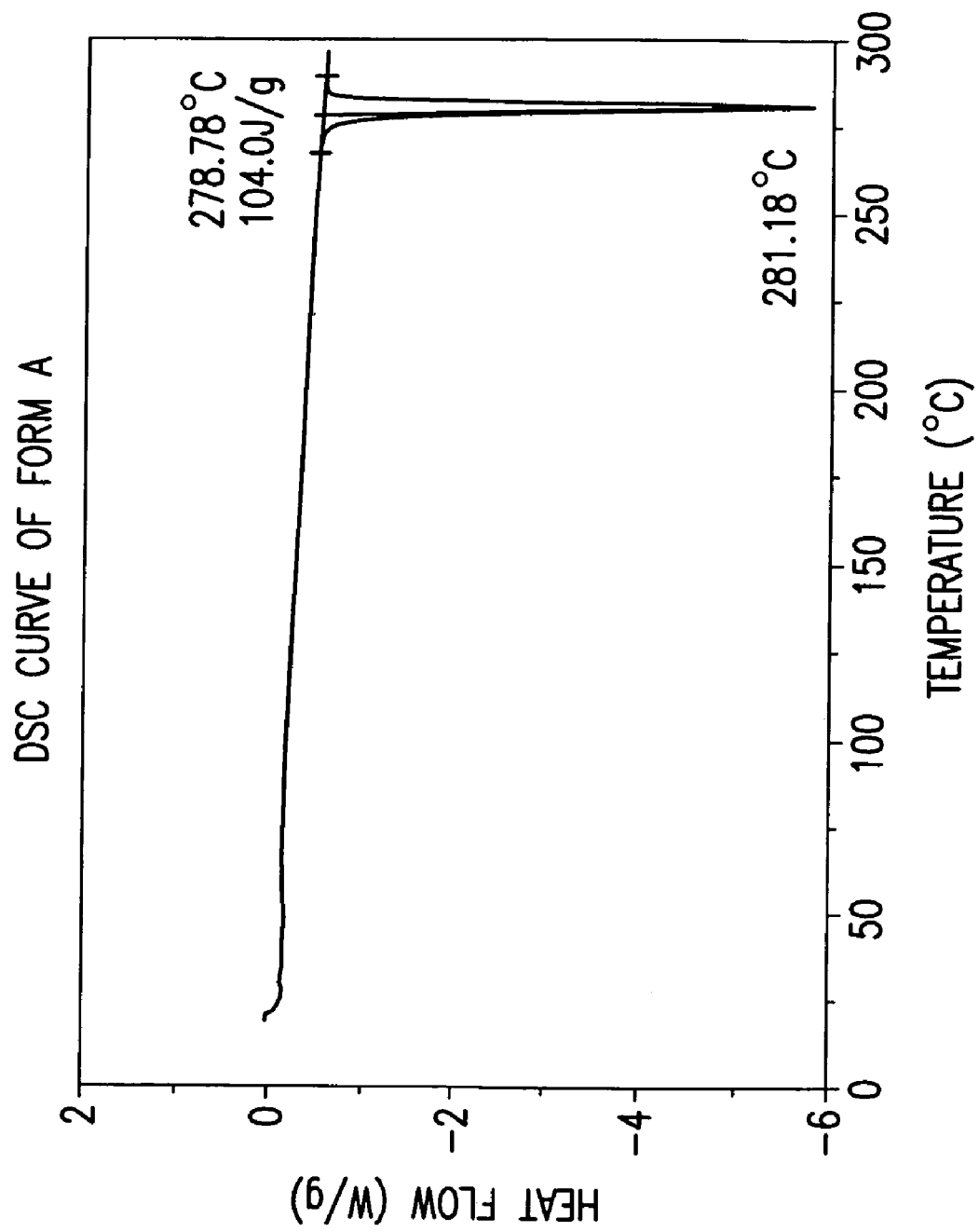
FIG. 4 is the typical DSC curve of the anhydrous crystalline Form A of compound I.

In one embodiment of the invention, the anhydrous crystalline Form A of compound I has a DSC curve as shown in FIG. 4. The melting endotherm exhibits a peak at approximately 281.2° C.

One embodiment of the invention relates to a process for making the anhydrous crystalline form A of the compound of formula I comprising: a) dissolving the compound in at least one solvent, to form a mixture; b) refluxing the mixture until crystallization is complete and solids are fromed; c) isolating the solids; and d) drying the solids.

In one embodiment of the invention, the at least one solvent is selected from 1,2-dimethoxyethane, isopropyl alcohol, isopropyl acetate, and acetone.

In one embodiment of the invention, isolating the solids further comprises filtering of the solids via a vacuum filter and washing the solids with at least one wash solvent selected from 1,2-dimethoxyethane, isopropyl alcohol, isopropyl acetate, and acetone.

In another embodiment of the invention, the solvent is 1,2-dimethoxyethane.

Figure 5:
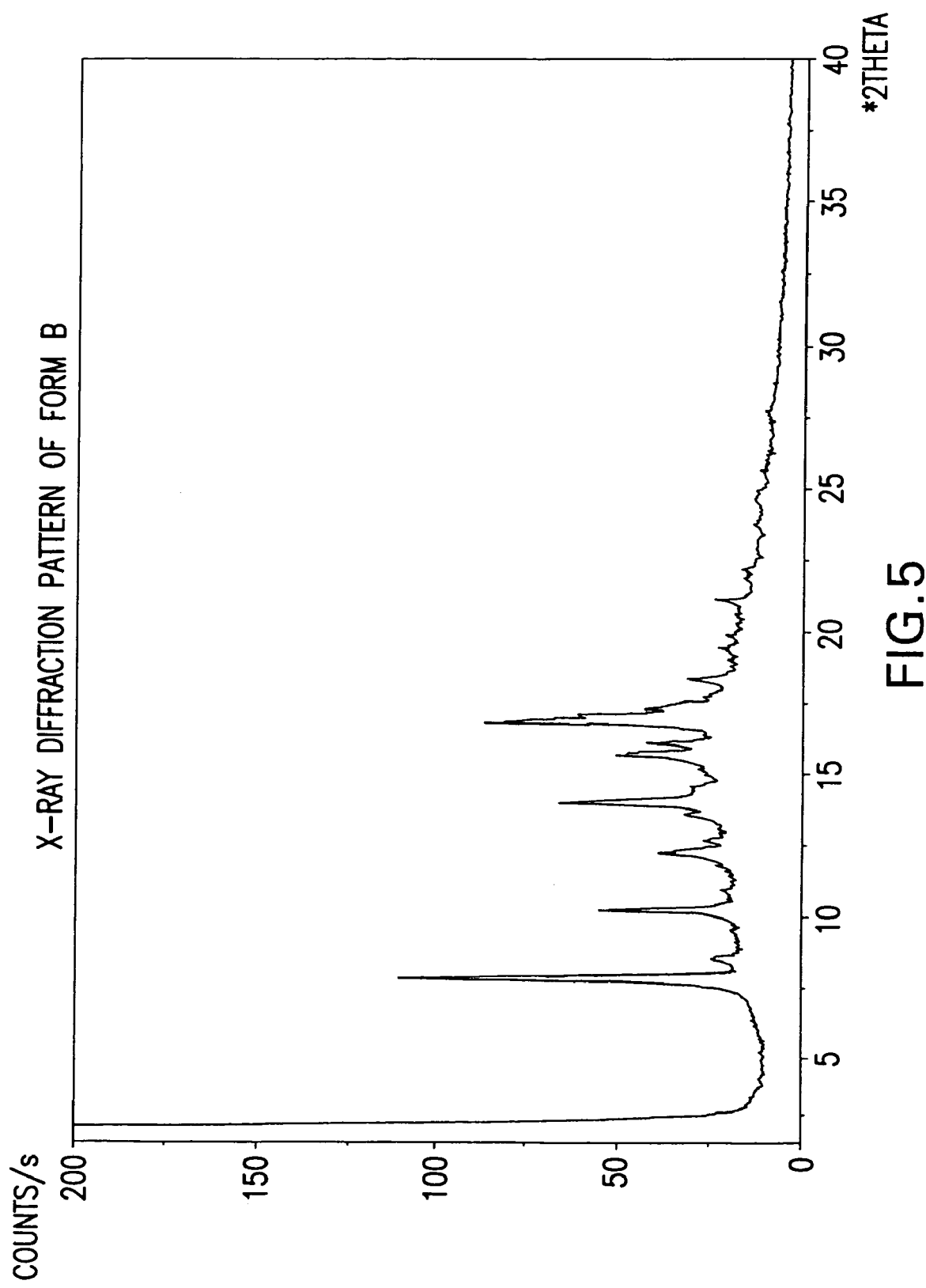
FIG. 5 is a X-ray diffraction pattern of the crystalline Form B of compound I.

One embodiment of the invention is a hygroscopic crystalline Form B, of N-(3H-imidazo[4,5-b]pyridin-2-ylmethyl)-2-fluoro-4-methyl-3-oxo-4-aza-androst-1-en-17-beta-carboxamide having a XRPD pattern with characteristic diffraction peaks corresponding 2-theta values of 7.8±0.1, 8.5±0.1, and 10.2±0.1. The hygroscopic crystalline Form B is further characterize additional diffraction peaks at 2-theta values of 12.2±0.1, 12.6±0.1, and 13.5±0.1. The hygroscopic crystalline Form B is still further characterized by diffraction peaks at 2-theta values of 13.9±0.1 and 16.8±0.1. A XRPD of hygroscopic crystalline Form B is presented in FIG. 5.

Figure 6:
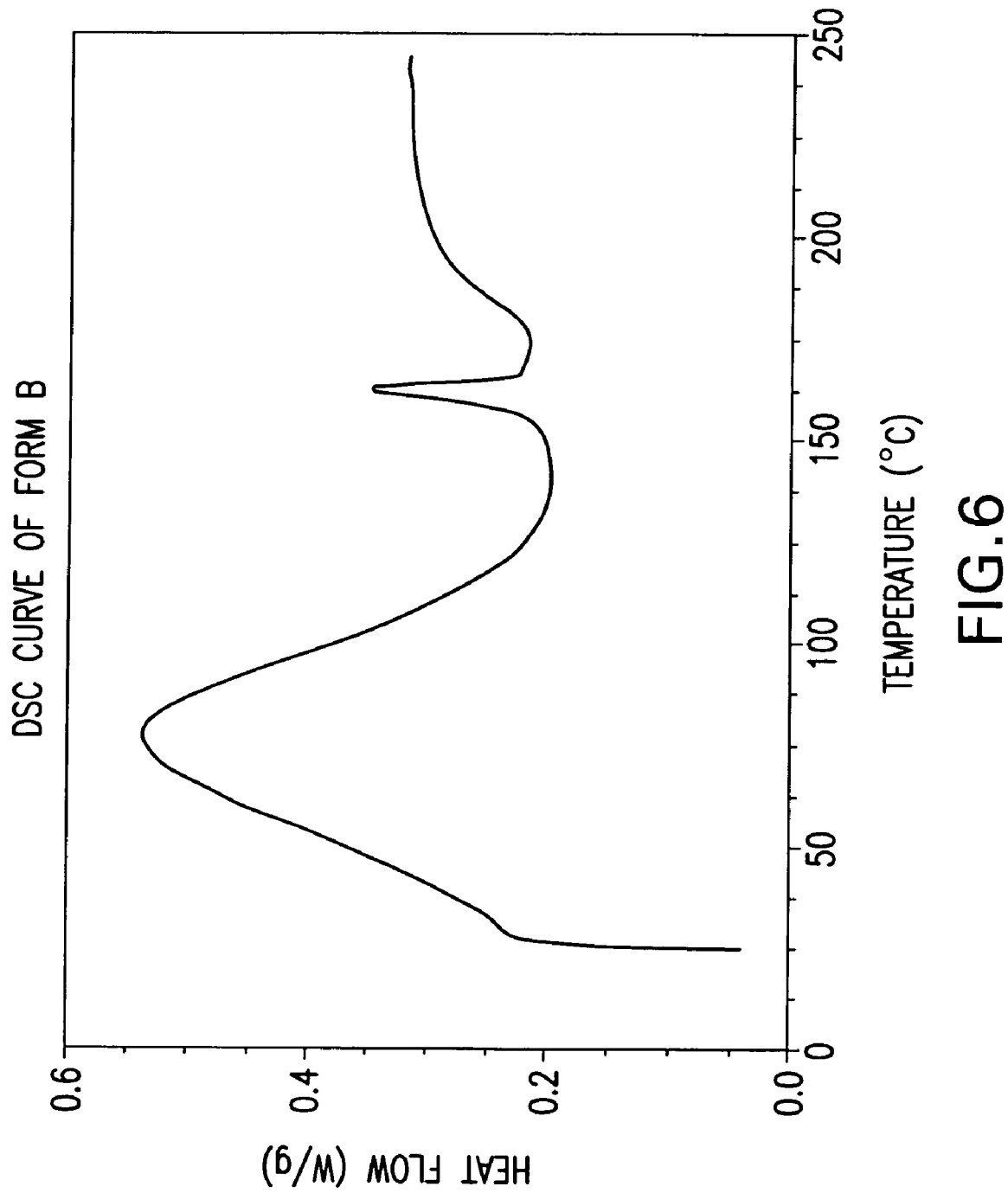
FIG. 6 is the typical DSC curve of the crystalline Form B of compound I.

In one embodiment of the invention, the hygroscopic crystalline Form B of compound I has a DSC curve as shown in FIG. 6. The DSC thermogram shows a broad endotherm centered at about 66.0° C. corresponding to the initial weight loss in TGA, followed by a melting endotherm at about 164.0° C.

Another embodiment of the invention comprises formation of hygroscopic crystalline Form B of compound I by: dissolving amorphous N-(3H-imidazo[4,5-b]pyridin-2-ylmethyl)-2-fluoro-4-methyl-3-oxo-4-aza-5α-androst-1-en-17β-carboxamide in a solvent; warming the mixture to ensure the amorphous form is dissolved; cooling the mixture; allowing the mixture to form needles (crystals), washing formed solids with a wash solvent; and drying the solids. In one embodiment, the solvent is ethanol and the wash solvent is ethanol. In another embodiment of the invention, the ratio of amorphous form to solvent is about 3:4 on a mass basis for example 3 gms of amporphous form of the compound and 4 (approximately 5 ml of ethanol). In yet another embodiement, the solution is heated to about 60° C.

In dynamic hygroscopicity tests, hygroscopic crystalline Form B gradually uptakes about 7% of moisture from about 25% to about 95% relative humidity (RH) at 25° C. The weight increase was based on the initial total sample weight at 25% RH. Additionally, hygroscopic crystalline Form B loses about 8% of its total weight at 25° C. when the relative humidity decreases from 95% to 5% RH. Crystalline Form B slowly loses crystallinity post moisture adsorption-desorption.

Figure 7:
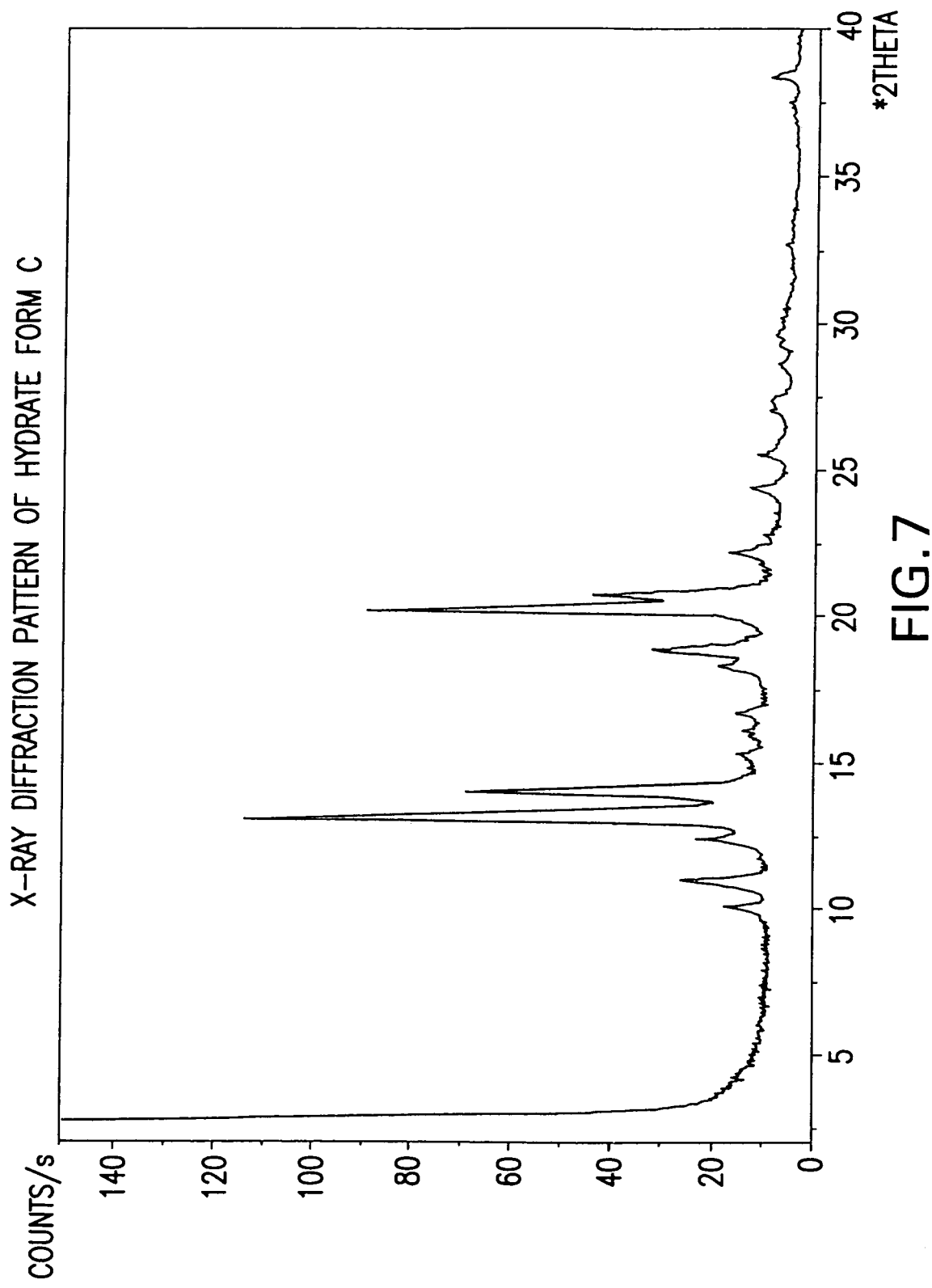
FIG. 7 is a X-ray diffraction pattern of the crystalline hydrate Form C of compound I.

Another embodiment of the invention is crystalline hydrate solid state Form C of the compound of formula I having a XRPD pattern with characteristic diffraction peaks corresponding 2-theta values of 10.1±0.1, 11.0±0.1, and 12.4±0.1. The crystalline hydrate Form C is further characterized by the additional diffraction peaks at 2-theta values of 13.2±0.1, 14.1±0.1, and 18.9±0.1. The crystalline hydrate Form C is still further characterized by diffraction peaks at 2-theta values of 20.3±0.1 and 22.7±0.1. A XRPD of crystalline hydrate Form C is shown in FIG. 7.

Figure 8:
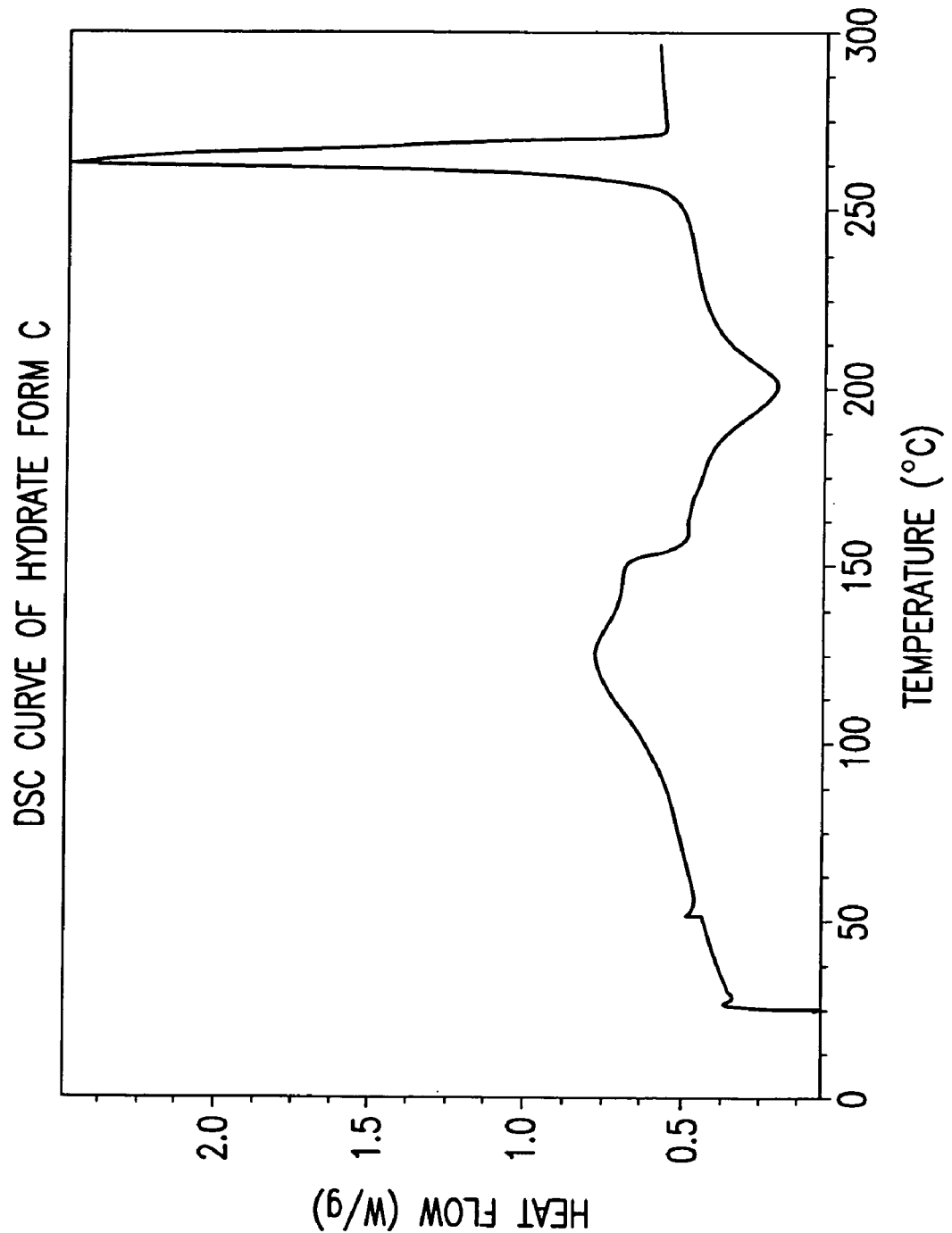
FIG. 8 is a DSC curve of the crystalline hydrate Form C of compound I.

Another embodiment of the invention is a DSC curve of the crystalline hydrate Form C of compound I depicted in FIG. 8. A broad dehydration endotherm centered at about 127.7° C. is followed by a crystallization exothermic activity at about 200.9° C. and a melting/decomposition endotherm at about 268.0° C. An initial weight loss of about 4.5% for Form C between about 25° C. and about 150° C. is attributed to dehydration (theoretical for monohydrate 3.6%), followed by thermal decomposition above 250° C.

Crystalline hydrate Form C may be made by suspending crystalline ethanolate Form G in water in an agitated vessel and letting the mixture age for a period of time. In one embodiment of the invention, ther ratio of crystalline ethanolate Form G to water is about 1:100 on a mass basis.

Figure 9:
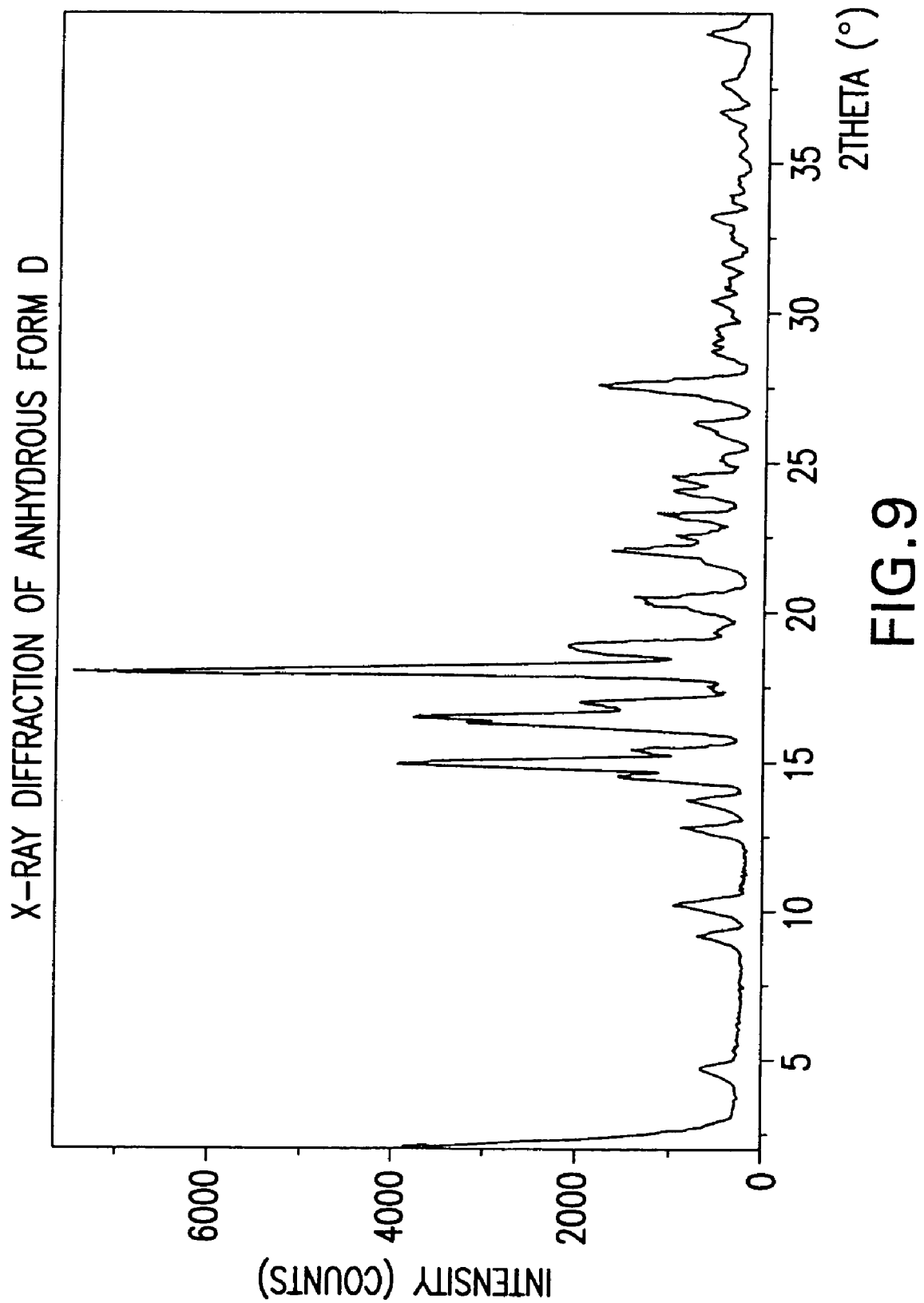
FIG. 9 is a X-ray diffraction pattern of the anhydrous crystalline Form D of compound I.

One embodiment of the invention is anhydrous crystalline Form D of the compound of formula I having a XRPD pattern with characteristic diffraction peaks corresponding 2-theta values of 8.8±0.1, 9.9±0.1, and 12.5±0.1. The anhydrous crystalline Form D is further characterized by the additional diffraction peaks at 2-theta values of 14.8±0.1, 16.3±0.1, and 17.9±0.1. The anhydrous crystalline Form D is still further characterized by diffraction peaks at 2-theta values of 14.3 ±0.1, 15.2±0.1 and 16.8±0.1. A XRPD of anhydrous crystalline Form D is shown in FIG. 9.

Figure 10:
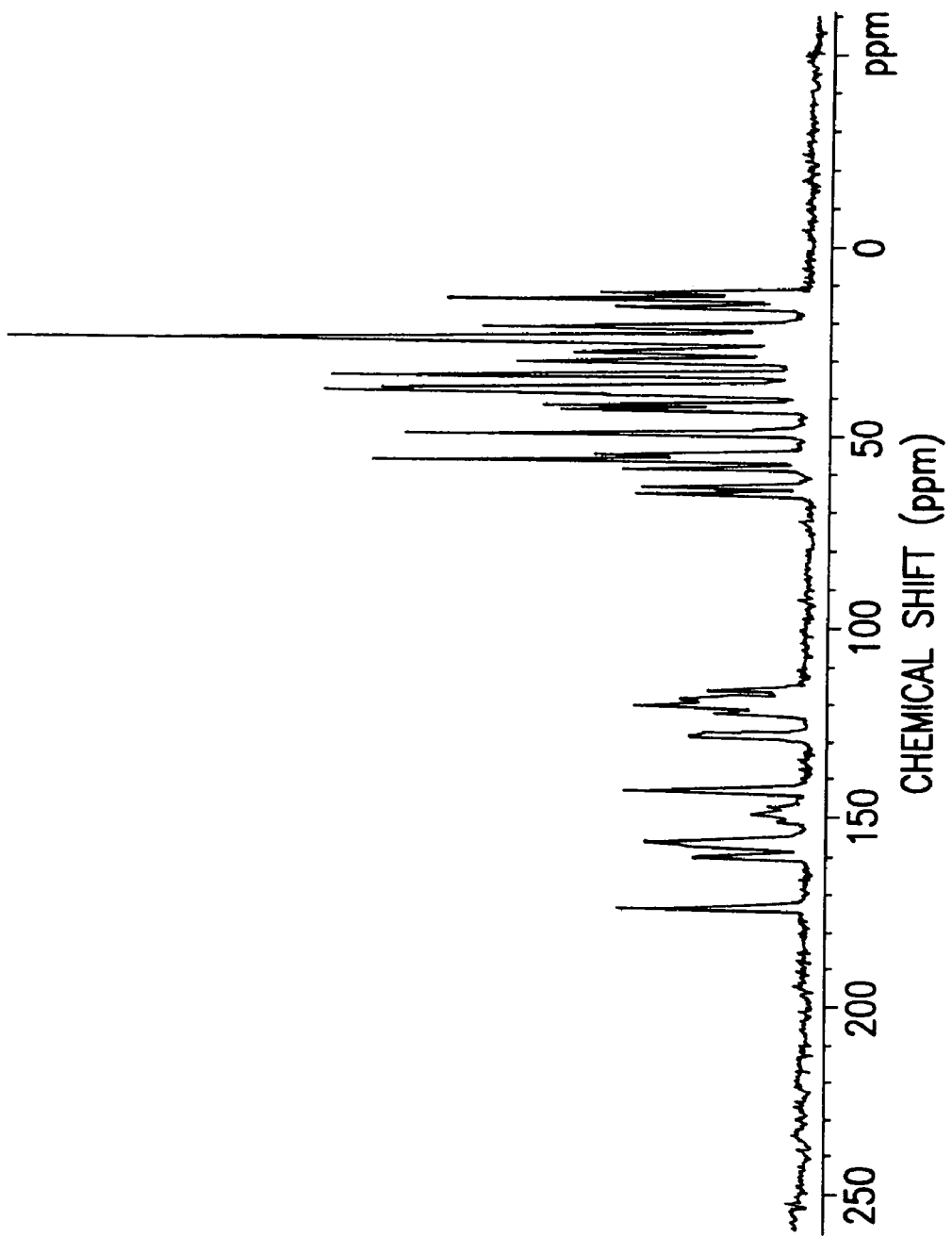
FIG. 10 is a carbon-13 cross-polarization magic-angle spinning (CPMAS) nuclear magnetic resonance (NMR) spectrum of the anhydrous crystalline Form D of compound I.

The anhydrous crystalline solid state Form D free base of compound of formula I exhibits a solid-state carbon-13 cross-polarization magic-angle spinning (CPMAS) nuclear magnetic resonance (NMR) spectrum (carbon-13 CPMAS NMR) spectrum having characteristic signals with chemical shift values of 23.8, 37.9, and 174.1±0.1 p.p.m. The crystalline solid Form D is further characterized as having signals with chemical shift values of 13.8, 48.8, and 156.9±0.1 p.p.m. An even further characteristic of the anhydrous crystalline Form D of compound I exhibits signals with chemical shift values of 20.9, 33.6, and 121.2±0.1 p.p.m. FIG. 10 shows a solid-state carbon-13 CPMAS NMR spectrum for the anhydrous crystalline Form D of the compound of formula 1.

Figure 11:
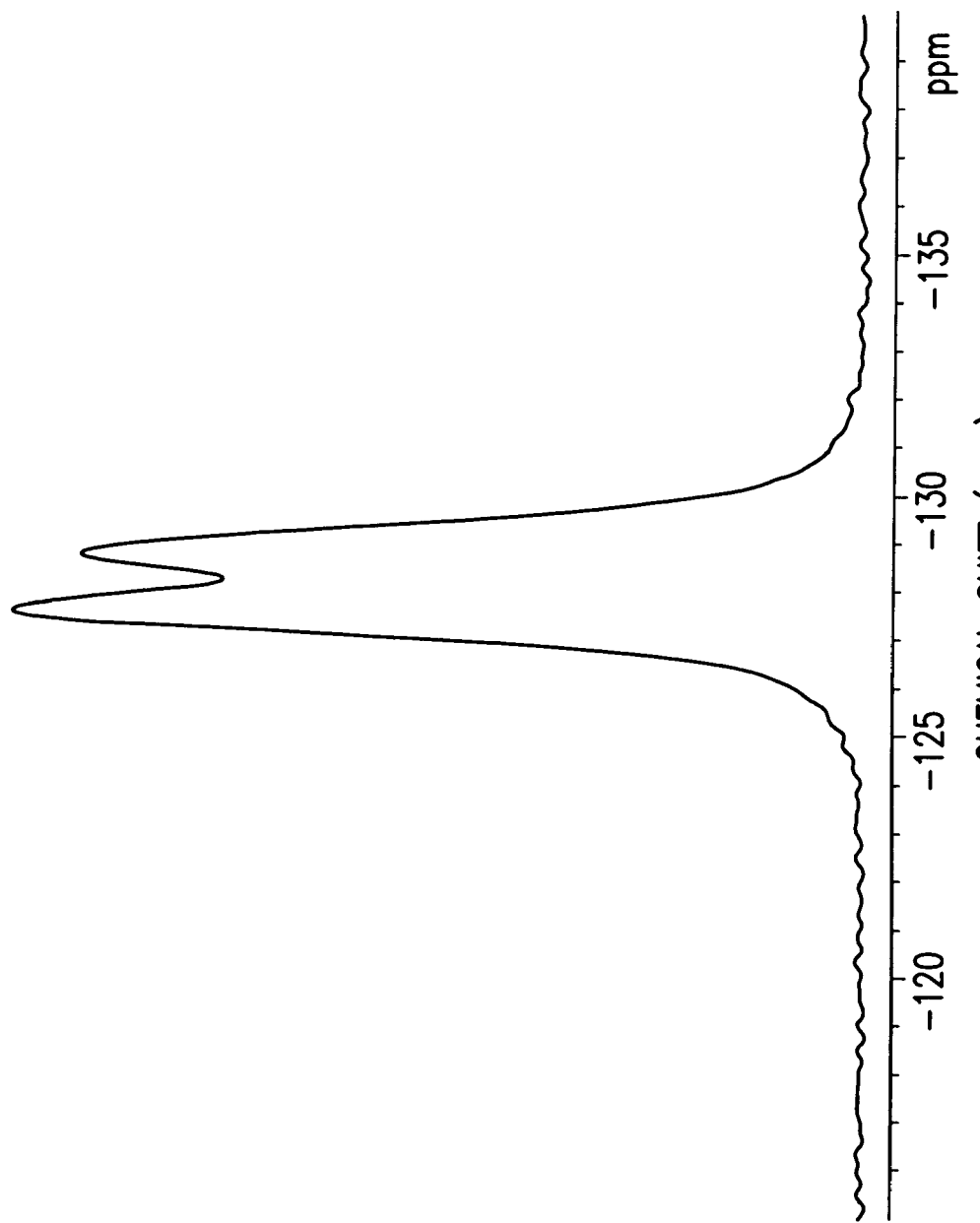
FIG. 11 is a fluorine-19 cross-polarization magic-angle spinning (CPMAS) nuclear magnetic resonance (NMR) spectrum of the anhydrous crystalline Form D of compound I.

In yet another embodiment, the solid-state fluorine-19 CPMAS NMR spectrum for the anhydrous crystalline Form D of compound I is shown in FIG. 11. The anhydrous crystalline solid state form exhibits a characteristic signal with chemical shift values of −127.7, and −128.9±0.1 p.p.m.

Figure 12:
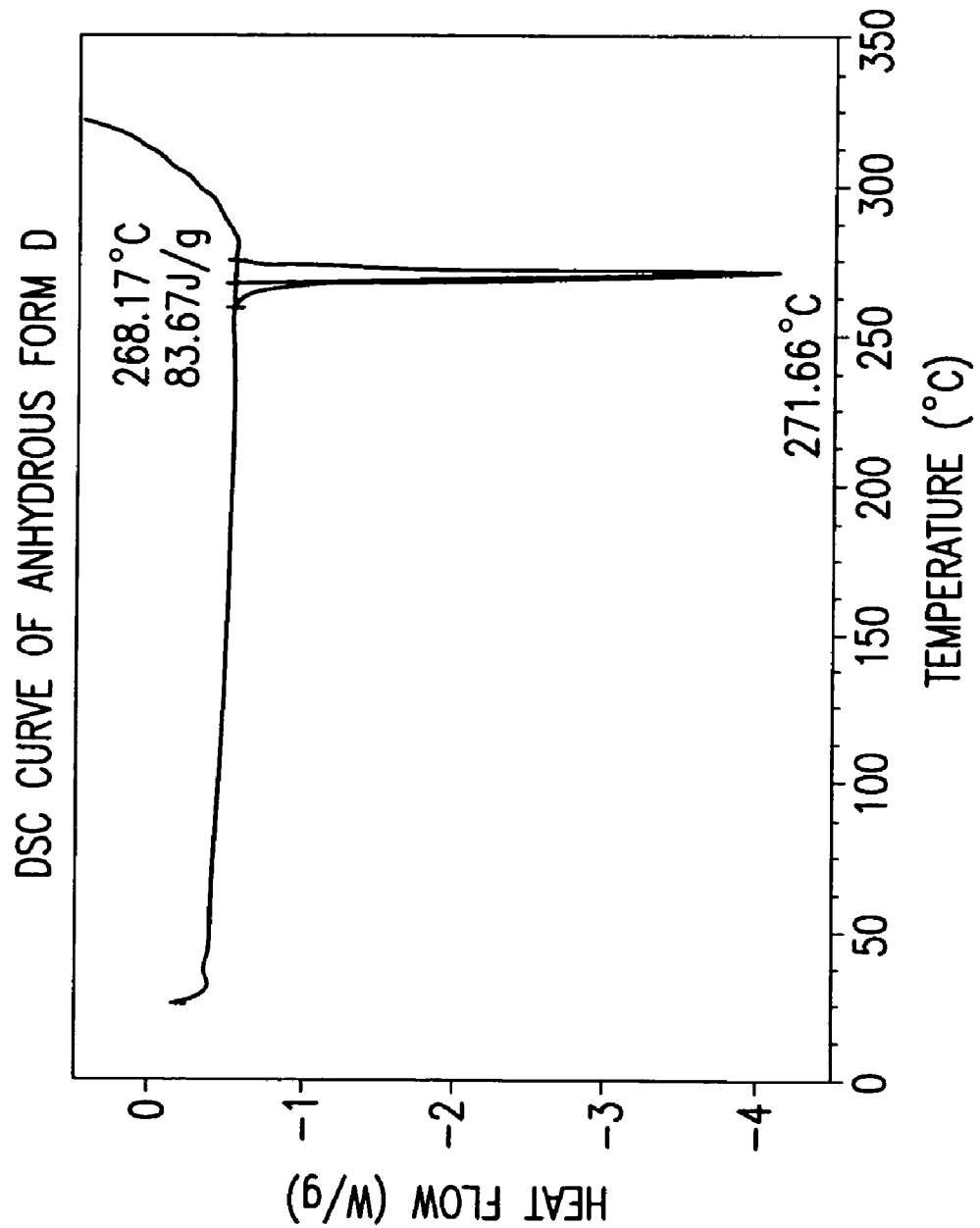
FIG. 12 is a DSC curve of the anhydrous crystalline Form D of compound I.

Another embodiment of the invention is a DSC curve of Form D of compound I depicted in FIG. 12. The DSC curve shows a melting endotherm with peak at about 273° C.

The anhydrous crystalline Form D is prepared by dissolving tetrahydrate Form E in at least one solvent to form a solution; charging at least one antisolvent to the solution until the solution is supersaturated; aging the batch and optionally adding more anti-solvent or cooling the batch until solids form. Solid formation from the supersaturated solution may be facilitated by seeding the solution with Form D seeds.

Non-limiting examples of the at least one solvent are selected from selected from dimethylacetamide (DMAc), methanol, dimethyl sulfoxide (DMSO), N,N-Dimethylformamide (DMF), and N-Methyl-2-Pyrrolidone (NMP). Non-limiting examples of the at least one antisolvent are chosen from heptane, toluene, cyclohexane, water, acetonitrile, isopropyl acetate, isobutyl acetate and methyl tertiary-butyl ether (MTBE). Non-limiting examples of solvent/anti-solvent systems include: methanol/water, DMSO/water, and NMP/water.

Figure 13:
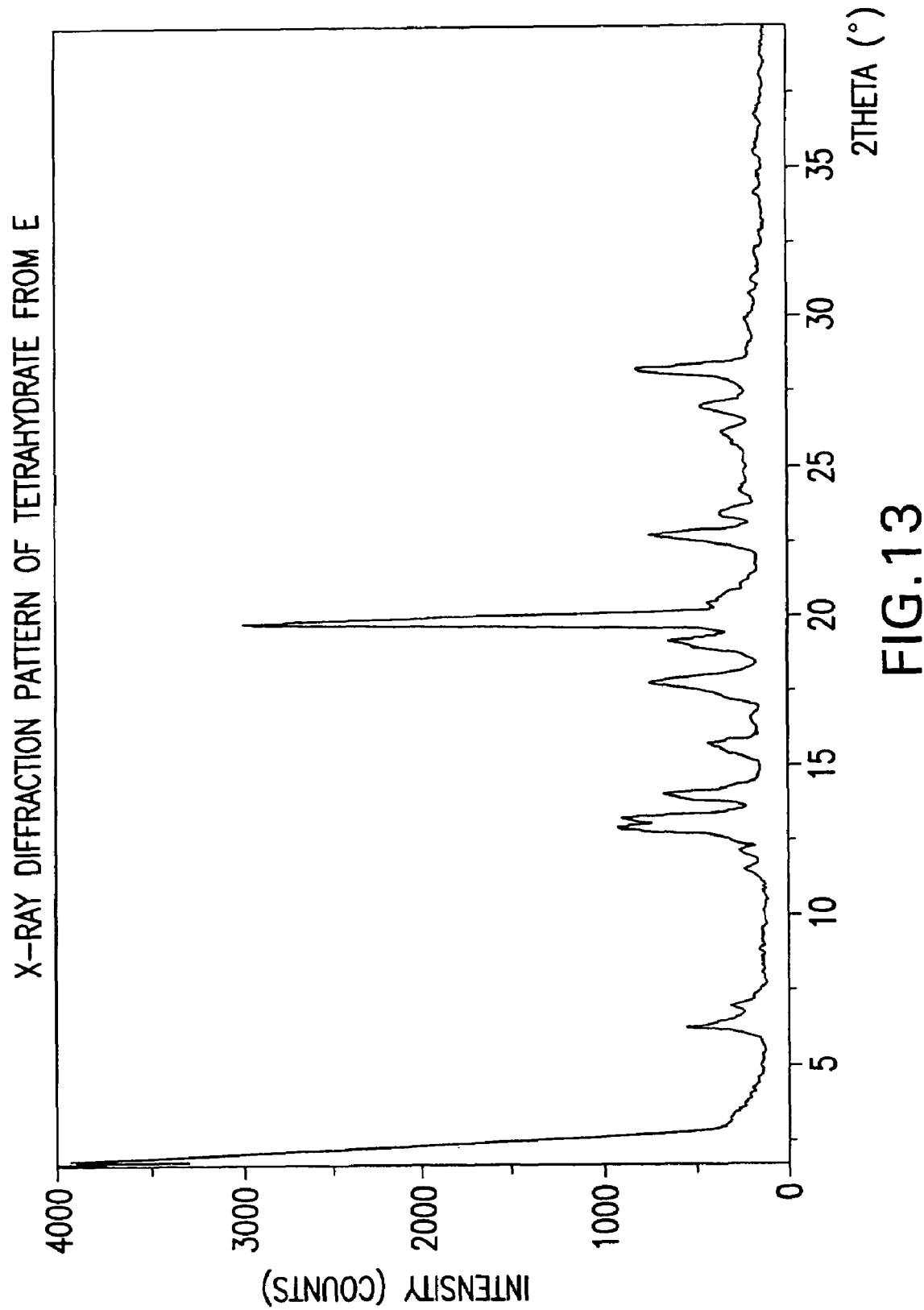
FIG. 13 is a XRPD of the crystalline Tetrahydrate Form E of compound I.

FIG. 13 shows the X-ray diffraction pattern for the crystalline tetrahydrate Form E, another embodiment of the invention. Tetrahydrate Form E with characteristic diffraction peaks corresponding 2-theta values of 6.1±0.1, 12.8±0.1, and 13.1±0.1. The tetrahydrate Form E is further characterized by the additional diffraction peaks at 2-theta values of 13.9±0.1, 17.6±0.1, and 19.0±0.1. The tetrahydrate Form E is still further characterized by diffraction peaks at 2-theta values of 19.8±0.1 and 22.6±0.1.

Figure 14:
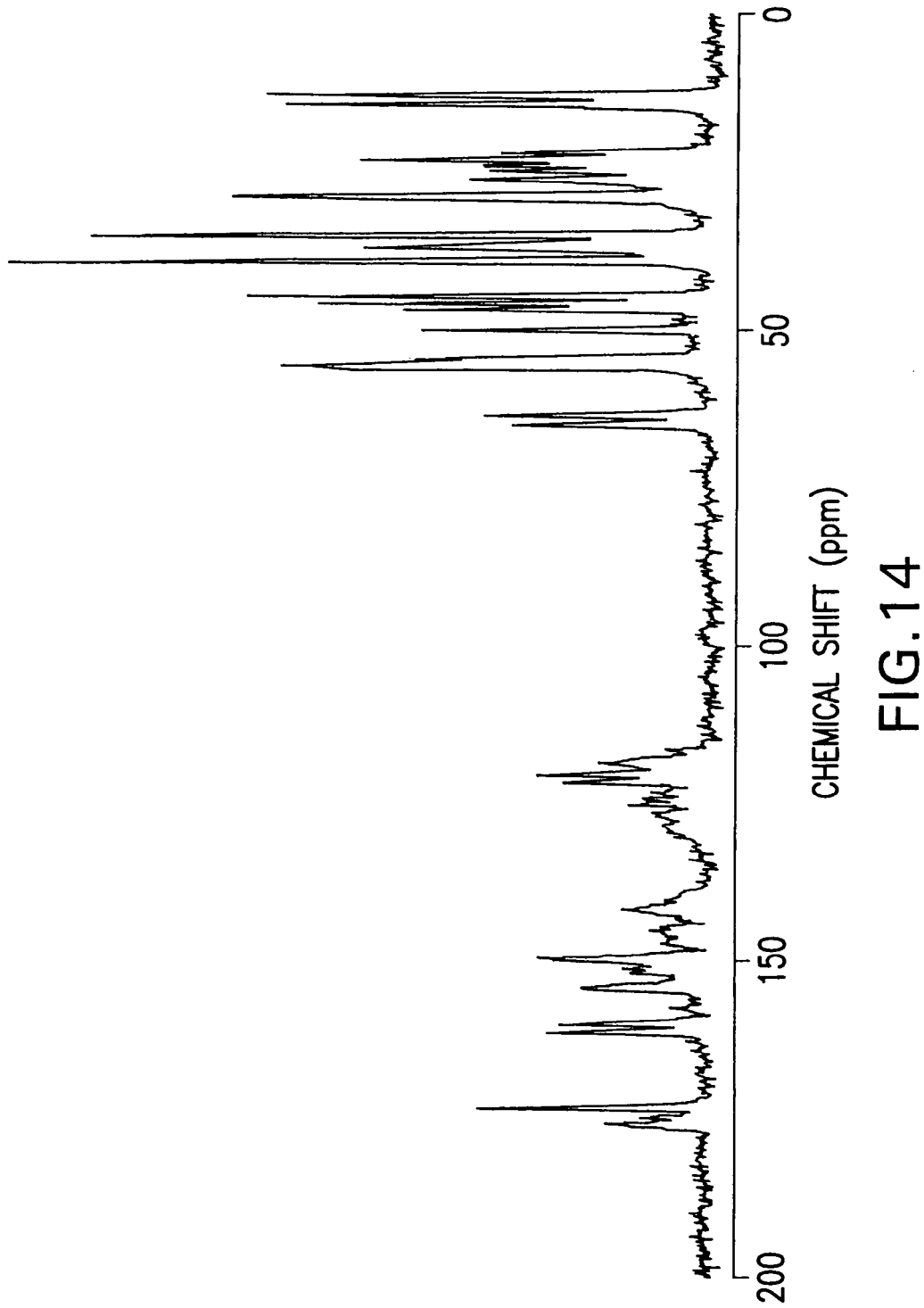
FIG. 14 is a carbon-13 cross-polarization magic-angle spinning (CPMAS) nuclear magnetic resonance (NMR) spectrum of the crystalline Tetrahydrate Form E of compound I.

The tetrahyrate Form E free base of compound of formula I exhibits a solid-state carbon-13 cross-polarization magic-angle spinning (CPMAS) nuclear magnetic resonance (NMR) spectrum (carbon-13 CPMAS NMR) spectrum having characteristic signals with chemical shift values of 13.1, 28.9, 39.3, and 154.2±0.1 p.p.m. The Tetrahyrate Form E is further characterized as having signals with chemical shift values of 14.6, 49.9, 173.2, and 120.6±0.1 p.p.m. An even further characteristic of the Tetrahyrate Form F of compound I exhibits signals with chemical shift values of 23.4, 35.1, 63.6, and 161.1±0.1 p.p.m. FIG. 14 shows a solid-state carbon-13 CPMAS NMR spectrum for the Tetrahyrate Form F of the compound of formula 1.

Figure 15:
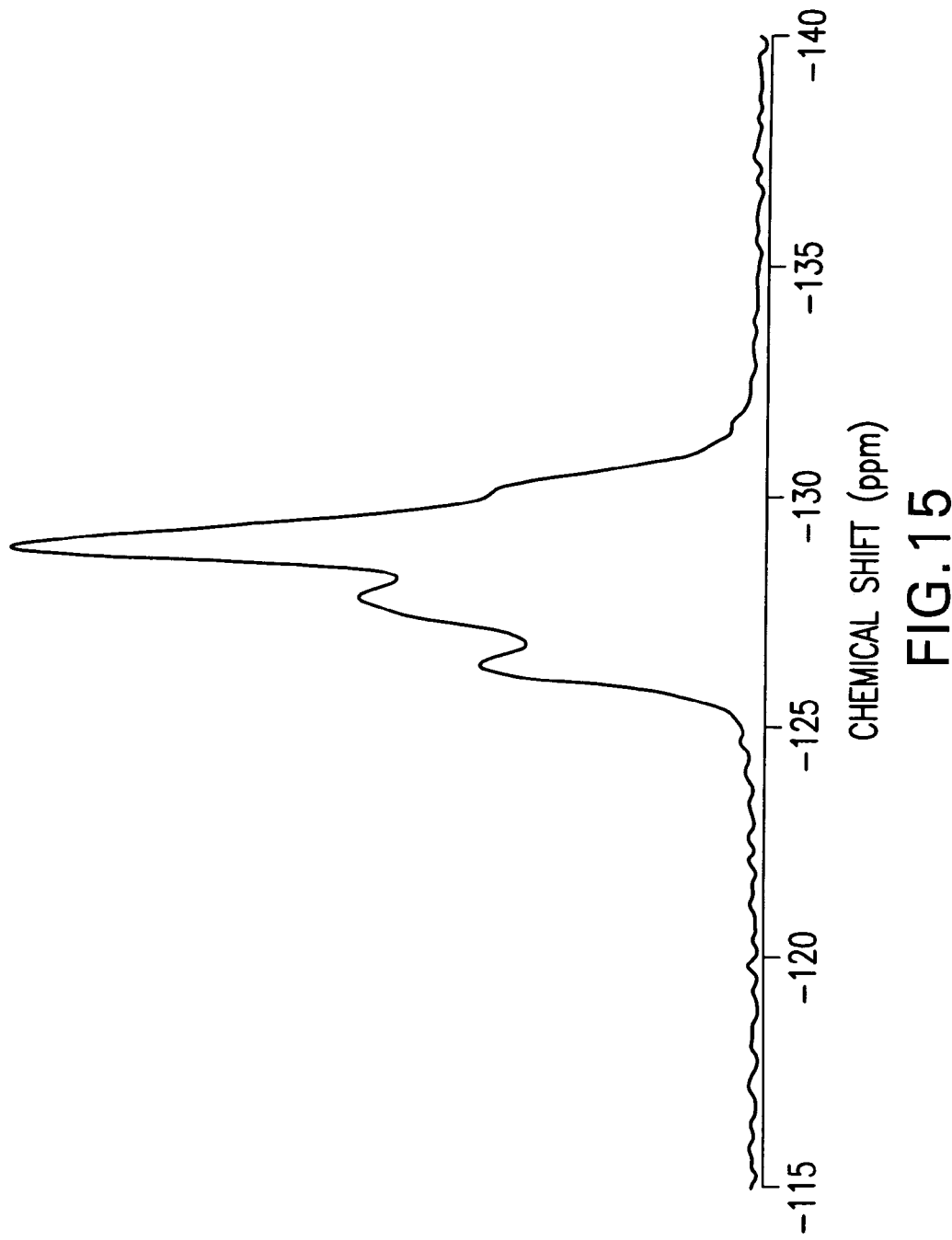
FIG. 15 is a fluorine-19 cross-polarization magic-angle spinning (CPMAS) nuclear magnetic resonance (NMR) spectrum of the crystalline Tetrahydrate Form E of compound I.

In yet another embodiment, the solid-state fluorine-19 CPMAS NMR spectrum for the Tetrahyrate Form E of compound I is shown in FIG. 15. The Tetrahyrate Form E exhibits a characteristic signal with chemical shift values of −126.5, −128.0, and −129.3±0.1 p.p.m.

Figure 16:
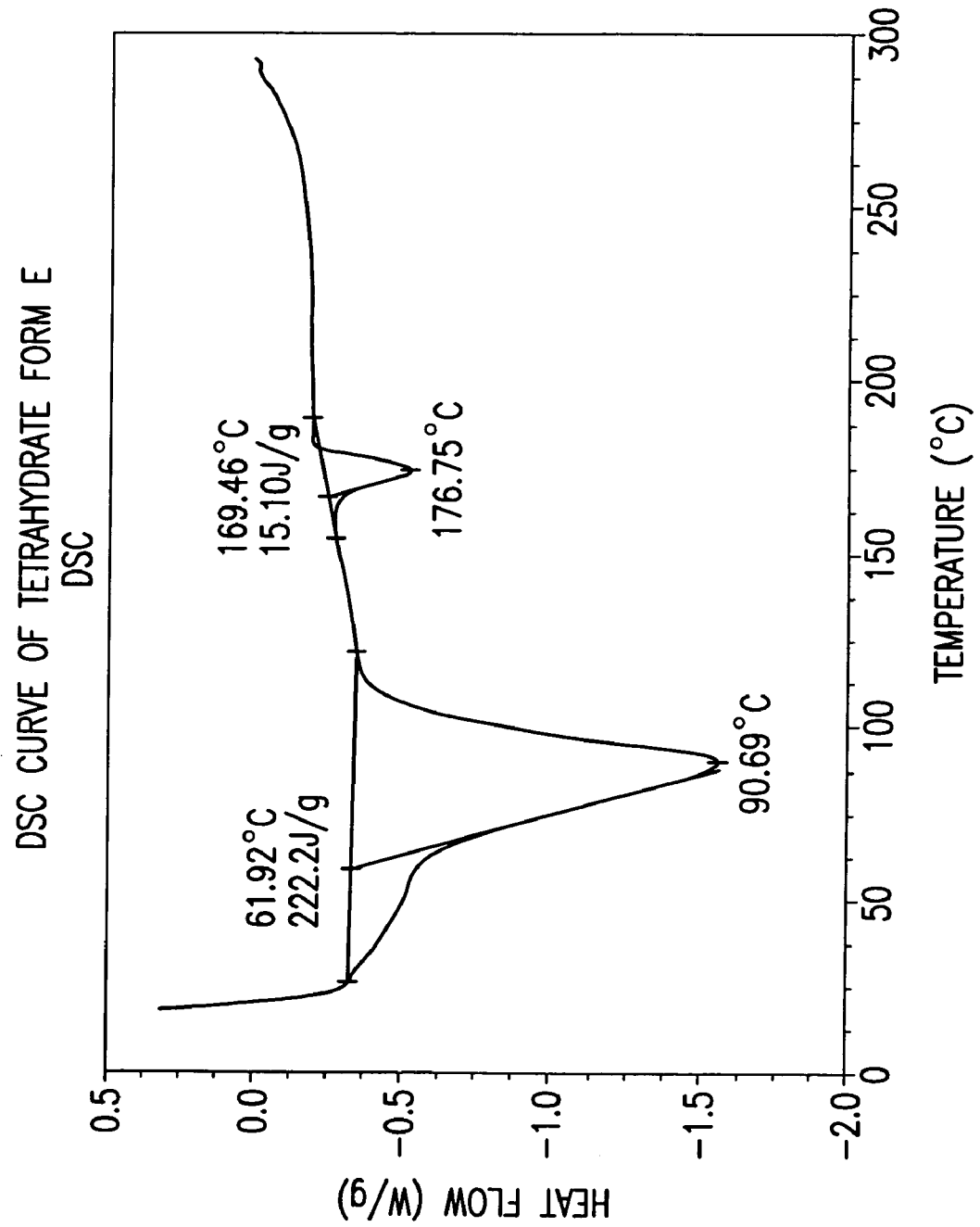
FIG. 16 is a DSC curve of the crystalline Tetrahydrate Form E of compound I.

FIG. 16 is a DSC curve of the crystalline tetrahydrate Form E of compound I. The broad endotherm centered around 90° C. is from the loss of water from the sample followed by the recrystallization to a new form, followed by the melting endotherm of this form at about 177° C.

The tetrahydrate Form E can be prepared by placing the anhydrous crystalline free base Form A in solutions having a pH of about 2 or less at room temperature and ambient conditions.

Figure 17:
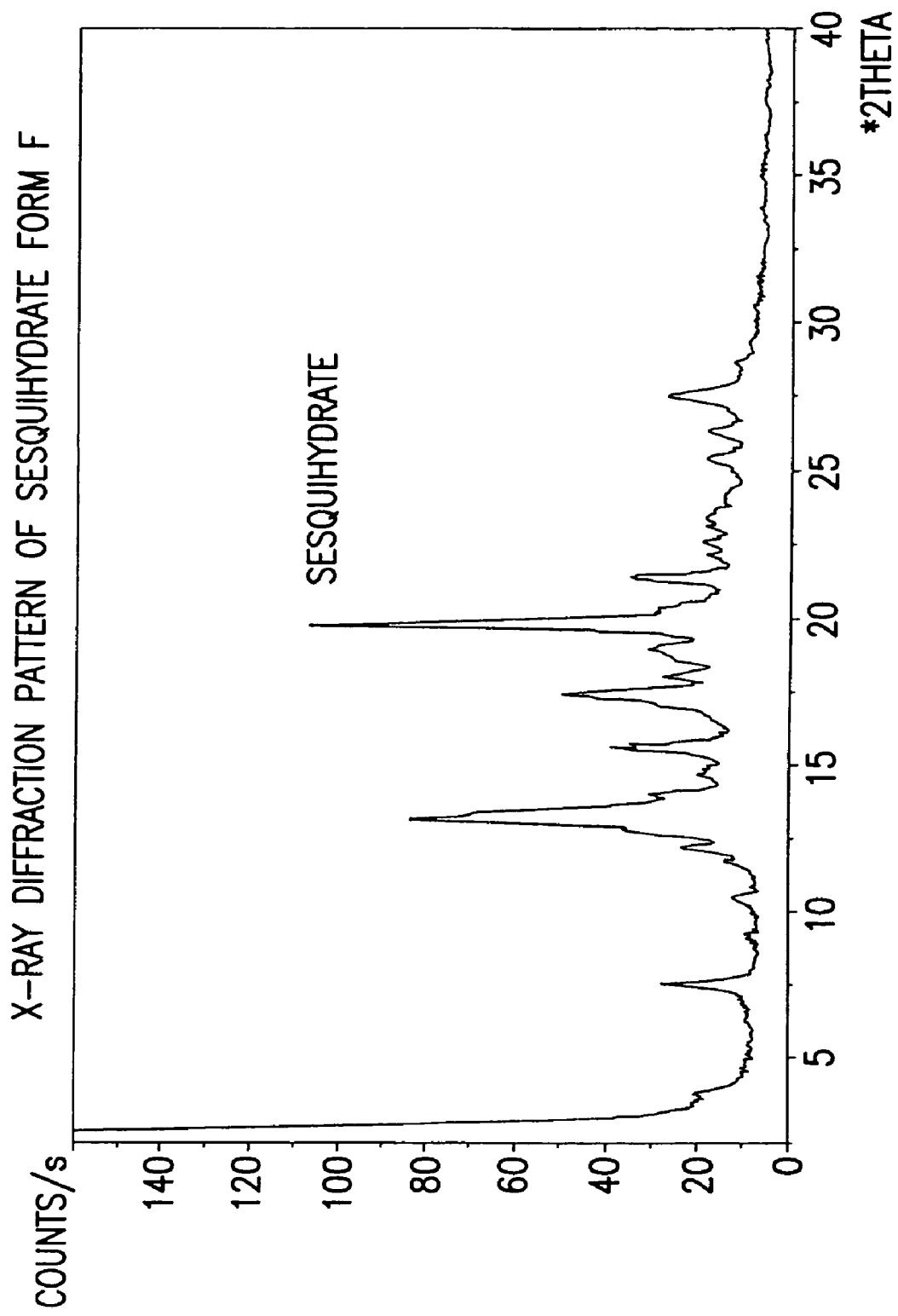
FIG. 17 is a X-ray diffraction pattern of the Sesquihydrate Form F of compound I.

Another embodiment of the invention is the Sesquihydrate Form F of compound I having a XRPD pattern with characteristic diffraction peaks corresponding 2-theta values of 6.3±0.1, 7.6±0.1, and 12.5±0.1. The sesquihydrate Form F is further characterized by the additional diffraction peaks at 2-theta values of 13.5±0.1, 15.5±0.1, and 18.3±0.1. The sesquihydrate Form F is still further characterized by diffraction peaks at 2-theta values of 19.7±0.1 and 21.0±0.1. A XRPD of sesquihydrate Form F is shown in FIG. 17.

Figure 18:
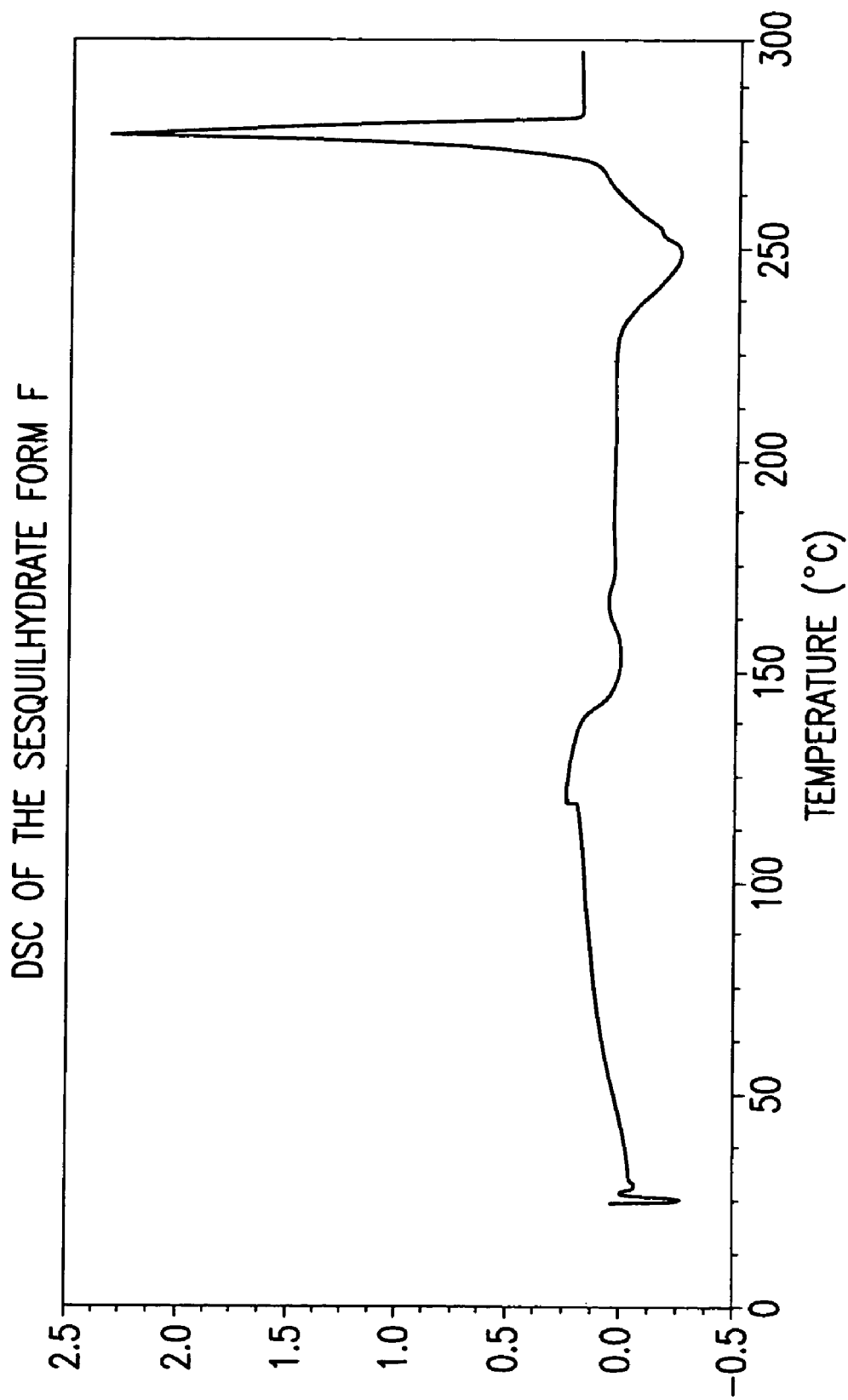
FIG. 18 is a TGA curve of the Sesquihydrate Form F of compound I

FIG. 18 is a DSC curve of the Sesquihydrate Form F of compound I. The DSC trace is qualitatively similar to the DSC trace of the Tetrahydrate Form E with a significant decrease in the endotherm seen from dehydration. The DSC trace was conducted from 25° C. to 350° C. with a heating rate of 10° C./min in a closed pan. A total weight loss, based on the initial weight of the sample, of about 5.1% was realized. The theorectical weight loss for a sesquihydrate was calculated to be 5.3%.

Sesquihydrate Form F can be prepared by vacuum drying the tetrahydrate Form E at 40° C. for at least 10 hours.

Figure 19:
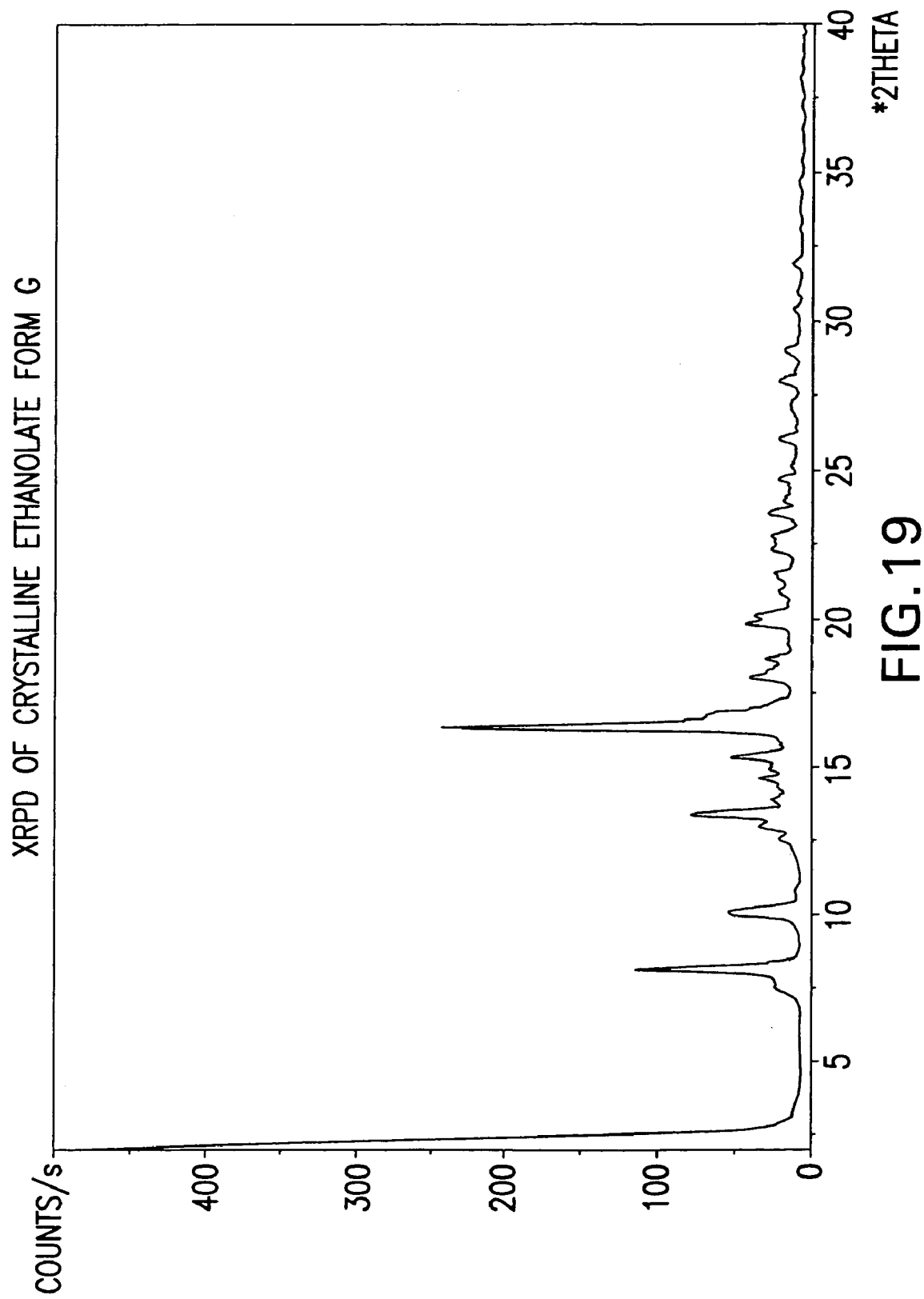
FIG. 19 is a X-ray diffraction pattern of crystalline ethanolate Form G of compound I.

One embodiment of the invention is a crystalline ethanolate Form G of compound I having a X-ray powder diffraction (XRPD) pattern with characteristic diffraction peaks corresponding 2-theta values of 8.2±0.1, 10.0±0.1, and 13.4±0.1. The crystalline ethanolate Form G is further characterized by the additional diffraction peaks at 2-theta values of 14.6±0.1, 15.3±0.1, and 16.4±0.1. The anhydrous crystalline ethanolate Form G is still further characterized by diffraction peaks at 2-theta values of 18.1±0.1 and 19.8±0.1. FIG. 19 shows the X-ray diffraction pattern for the crystalline ethanolate Form G.

Figure 20:
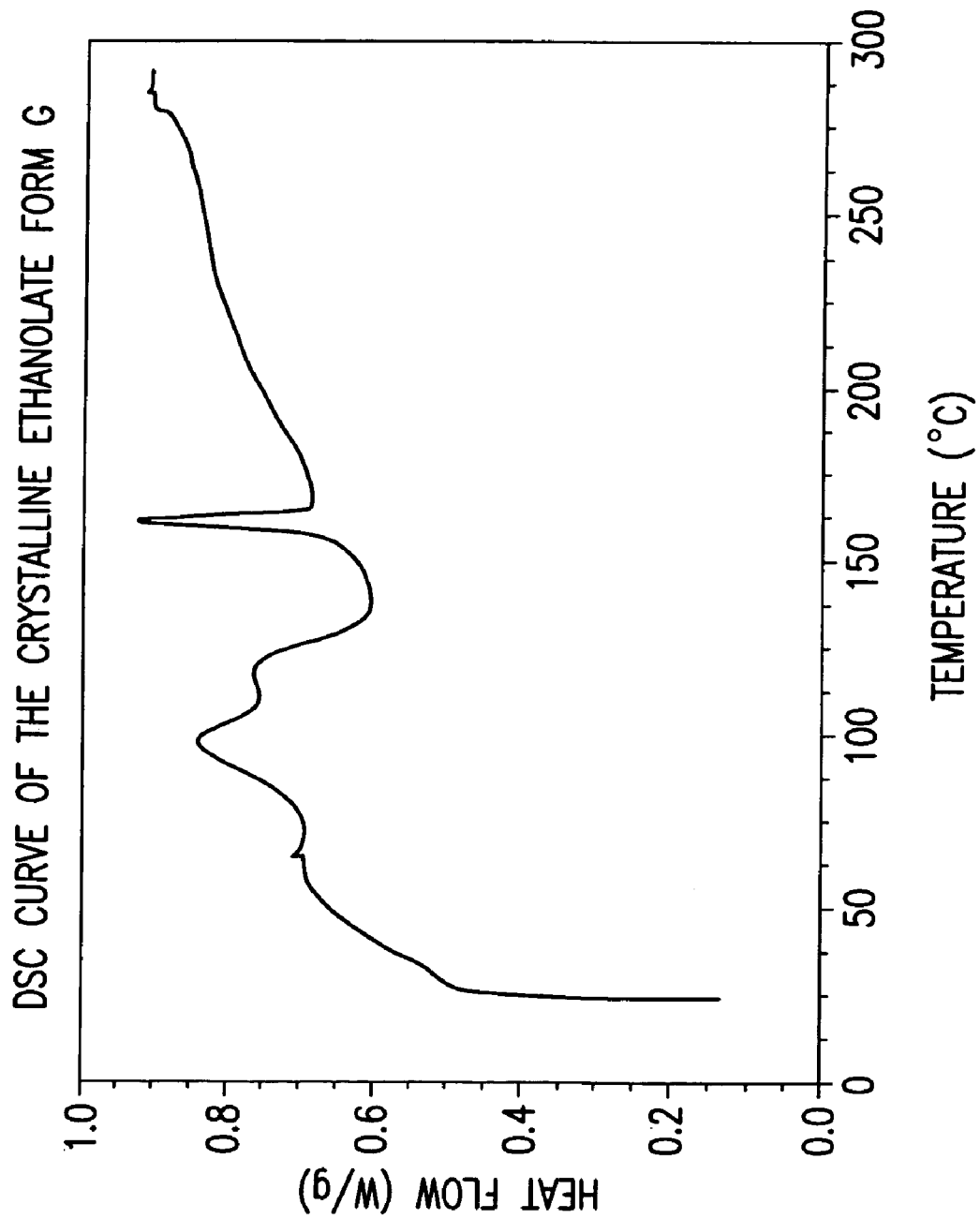
FIG. 20 is a typical DSC curve of the crystalline ethanolate Form G of compound I.

FIG. 20 depicts a representative DSC curve of the crystalline ethanolate Form G of compound I. The DSC trace of the crystalline ethanolate Form G shows two broad desolvation endotherms centered at about 97.1° C. and 121.6° C., followed by a melting endotherm at about 165.9° C.

A total weight loss of about 5.0% is typical for crystalline ethanolate Form G between 25° C. to 100° C. Thermal decomposition occurs above about 250° C. The gas liberated from the initial weight loss was analyzed as ethanol using a mass spectrometer connected to the TGA furnace exhaust.

The crystalline ethanolate Form G may be formed by dissolving amorphous N-(3H-imidazo[4,5-b]pyridin-2-ylmethyl)-2-fluoro-4-methyl-3-oxo-4-aza-5α-androst-1-en-17β-carboxamide in ethanol and heating the solution to about 60° C. followed by cooling of the mixture to room temperature so as to form solids.

One embodiment, a polymorph/pseudopolymorph in accordance with the present invention is "substantially pure" and has a polymorphic/pseudomorphic purity of about at least 85%. That is, with reference to a particular crystalline form, the crystalline form comprises less than about 15% by weight of impurities, including other polymorphic, amorphous, and/or pseudopolymorphic forms. In a variant of this embodiment, the polymorphic/psuedopolymorphic purity is at least 95%.

In another embodiment, the amorphous form of the compound of formula I is "substantially pure" and has a purity of about at least 85%. That is, with reference to the solid form of the compound of formula I, the amorphous form comprises less than about 15% by weight of impurities, including other polymorphic, and/or pseudopolymorphic forms. In a variant of this embodiment, the amorphous purity is at least 95%. The XRPD pattern of a typical amorphous material is shown in FIG. 21.

X-ray powder diffraction studies are widely used to characterize molecular structures, crystallinity, and polymorphism. The X-ray powder diffraction (XRPD) pattern of the crystalline form of the compound of formula I was generated on a Philips Analytical X'Pert PRO X-ray Diffraction System with PW3040/60 console. A PW3373/00 ceramic Cu LEF X-ray tube K-Alpha radiation was used as the source.

In addition to the X-ray powder diffraction patterns described above, the crystalline form of compound I was further characterized by their solid-state carbon-13 and fluorine-19 nuclear magnetic resonance (NMR) spectra. The solid-state carbon-13 NMR spectra were obtained on a Bruker DSX 400WB NMR system using a Bruker 4 mm double resonance CPMAS probe. The carbon-13 NMR spectra utilized proton/carbon-13 cross-polarization magic-angle spinning with variable-amplitude cross polarization and total-sideband-suppression. The samples were spun at 10.0 kHz, and a total of 1024 scans were collected with a recycle delay of 10 seconds. A line broadening of 10 Hz was applied to the spectra before FT was performed. Chemical shifts are reported on the TMS scale using the carbonyl carbon of glycine (176.03 p.p.m.) as a secondary reference.

The solid-state fluorine-19 NMR spectra were obtained on a Bruker DSX 500WB NMR system using a Bruker 4 mm H/F/X probe. The NMR spectra utilized proton/fluorine-19 cross-polarization magic-angle spinning with variable-amplitude cross polarization and TPPM decoupling at 62.5 kHz. The samples were spun at 15.0 kHz, and a total of 150 scans were collected with a recycle delay of 5 seconds. A line broadening of 10 Hz was applied to the spectrum before FT was performed. Chemical shifts are reported using poly(tetrafluoroethylene) (Teflon®) as an external secondary reference which was assigned a chemical shift of −122 ppm.

Differential Scanning Calorimeter (DSC) data were acquired using TA Instruments DSC 2910 or equivalent instrumentation. Between 1 and 6 mg sample is weighed into an open pan. This pan is then crimped and placed at the sample position in the calorimeter cell. An empty pan is placed at the reference position. The calorimeter cell is closed and a flow of nitrogen is passed through the cell. The heating program is set to heat the sample at a heating rate of 10° C./min to a temperature of approximately 300° C. The heating program is started. When the run is completed, the data are analyzed using the DSC analysis program contained in the system software. The melting endotherm is integrated between baseline temperature points that are above and below the temperature range over which the endotherm is observed. The data reported are the onset temperature, peak temperature and enthalpy.

One embodiment of the invention is an amorphous solid form of N-(3H-imidazo[4,5-b]pyridin-2-ylmethyl)-2-fluoro-4-methyl-3-oxo-4-aza-5-alpha-androst-1-en-17-beta-carboxamide. FIG. 21 depicts a typical XRPD pattern for the amorphous form of compound I.

The solid state forms of the present invention can include a mixture of two or more forms. The mixtures of the solid states in accordance with the present invention will have X-ray diffraction peaks characteristic of each of the various polymorphic forms present in the mixture.

The solid state forms of the compound of the present invention identified as a SARM are useful to treat diseases or conditions caused by androgen deficiency which can be ameliorated by androgen administration. Such amorphous, solvates, and crystalline forms are ideal for the treatment of osteoporosis in women and men as a monotherapy or in combination with inhibitors of bone resorption, such as bisphosphonates, estrogens, SERMs, cathepsin K inhibitors, $\alpha v \beta 3$ integrin receptor antagonists, calcitonin, and proton pump inhibitors. They can also be used with agents that stimulate bone formation, such as parathyroid hormone or analogs thereof. The various solid forms of the SARM compound of the present invention can also be employed for treatment of prostate disease, such as prostate cancer and benign prostatic hyperplasia (BPH). Moreover, the solid state forms of the compound of this invention exhibit minimal effects on skin (acne and facial hair growth) and can be useful for treatment of hirsutism. Additionally, the compound of structural formula I can stimulate muscle growth and can be useful for treatment of sarcopenia and frailty. They can be employed to reduce visceral fat in the treatment of obesity. Moreover, compound of this invention can exhibit androgen agonism in the central nervous system and can be useful to treat vasomotor symptoms (hot flush) and to increase energy and libido. They can be used in the treatment of Alzheimer's disease.

The solid forms of compound of formula I can also be used in the treatment of prostate cancer, either alone or as an adjunct to GnRH agonist/antagonist therapy, for their ability to restore bone, or as a replacement for antiandrogen therapy because of their ability to antagonize androgen in the prostate, and minimize bone depletion. Further, the compound of the present invention can be used for their ability to restore bone in the treatment of pancreatic cancer as an adjunct to treatment with antiandrogen, or as monotherapy for their antiandrogenic properties, offering the advantage over traditional antiandrogens of being bone-sparing. Additionally, compounds of this invention can increase the number of blood cells, such as red blood cells and platelets, and can be useful for the treatment of hematopoietic disorders, such as aplastic anemia. Thus, considering their tissue selective androgen receptor agonism listed above, the crystalline and amorphous forms of the compound of formula I are ideal for hormone replacement therapy in hypogonadic (androgen deficient) men.

This invention is also concerned with safely and specifically treating a male subject with abdominal adiposity, metabolic syndrome (also known as the 'insulin resistance syndrome' and 'Syndrome X'), and type II diabetes.

The compound of formula I has been found to be tissue-selective modulators of the androgen receptor (SARMs). In one aspect, the solid state forms of the compound of the present invention can be useful to activate the function of the androgen receptor in a mammal, and in particular to activate the function of the androgen receptor in bone and/or muscle tissue and block or inhibit ("antagonize") the function of the androgen receptor in the prostate of a male individual or in the uterus of a female individual.

A further aspect of the present invention is the use of amorphous and crystalline forms of compound of formula I to attenuate or block the function of the androgen receptor in the prostate of a male individual or in the uterus of a female individual induced by AR agonists, but not in hair-growing skin or vocal cords, and activate the function of the androgen receptor in bone and/or muscle tissue, but not in organs which control blood lipid levels (e.g. liver).

The compound of structural formula I displays submicromolar binding affinity for the androgen receptor and is useful in treating mammals suffering from disorders related to androgen receptor function. Therapeutically effective amounts of the compound, including polymorph(s), pseudopolymorph(s), and amorphous forms, and mixtures thereof, are administered to the mammal, to treat disorders related to androgen receptor function, such as, androgen deficiency, disorders which can be ameliorated by androgen replacement, or which can be improved by androgen replacement, including: enhancement of weakened muscle tone, osteoporosis, osteopenia, glucocorticoid-induced osteoporosis, periodontal disease, bone fracture (for example, vertebral and non-vertebral fractures), bone damage following bone reconstructive surgery, sarcopenia, frailty, aging skin, male hypogonadism, postmenopausal symptoms in women, atherosclerosis, hypercholesterolemia, hyperlipidemia, obesity, aplastic anemia and other hematopoietic disorders, pancreatic cancer, inflammatory arthritis and joint repair, HIV-wasting, prostate cancer, benign prostatic hyperplasia (BPH), cancer cachexia, Alzheimer's disease, muscular dystrophies, cognitive decline, sexual dysfunction, sleep apnea, depression, premature ovarian failure, and autoimmune disease. Treatment is effected by administration of a therapeutically effective amount of a compound of structural formula I to a mammal in need of such treatment. In addition, the solid state forms of the compound of formula I are useful as ingredients in pharmaceutical compositions alone or in combination with other active agents.

In one embodiment, the amorphous and crystalline solid forms of the compound of the present invention can be used to treat conditions in a male individual which are caused by androgen deficiency or which can be ameliorated by androgen replacement, including, but not limited to, osteoporosis, osteopenia, glucocorticoid-induced osteoporosis, periodontal disease, HIV-wasting, prostate cancer, cancer cachexia, obesity, arthritic conditions, anemias, such as for example, aplastic anemia, muscular dystrophies, and Alzheimer's disease, cognitive decline, sexual dysfunction, sleep apnea, depression, benign prostatic hyperplasia (BPH), abdominal obesity, metabolic syndrome, type II diabetes, and atherosclerosis, alone or in combination with other active agents. Treatment is effected by administration of a therapeutically effective amount of the compound of structural formula I to a male individual in need of such treatment.

"Arthritic condition" or "arthritic conditions" refers to a disease wherein inflammatory lesions are confined to the joints or any inflammatory conditions of the joints, most notably osteoarthritis and rheumatoid arthritis (Academic Press Dictionary of Science Technology; Academic Press; 1st edition, Jan. 15, 1992). The compound of formula I of the present invention is also useful, alone or in combination, to treat or prevent arthritic conditions, such as Behcet's disease; bursitis and tendinitis; CPPD deposition disease; carpal tunnel syndrome; Ehlers-Danlos syndrome; fibromyalgia; gout; infectious arthritis; inflammatory bowel disease; juvenile arthritis; lupus erythematosus; lyme disease; marfan syndrome; myositis; osteoarthritis; osteogenesis imperfecta; osteonecrosis; polyarteritis; polymyalgia rheumatica; psoriatic arthritis; Raynaud's phenomenon; reflex sympathetic dystrophy syndrome; Reiter's syndrome; rheumatoid arthritis; scleroderma; and Sjogren's syndrome. An embodiment of the invention encompasses the treatment or prevention of an arthritic condition which comprises administering a therapeutically effective amount of the amorphous and crystalline forms, either alone or as a mixture, of the compound of formula I. A subembodiment is the treatment or prevention of osteoarthritis, which comprises administering a therapeutically effective amount of a Compound of Formula I. See: Cutolo M, Seriolo B, Villaggio B, Pizzorni C, Craviotto C, Sulli A. *Ann. N.Y. Acad. Sci.* 2002 June; 966:131-42; Cutolo, M. *Rheum Dis Clin North Am* 2000 November; 26(4):881-95; Bijlsma J W, Van den Brink H R. *Am J Reprod Immunol* 1992 October-December; 28(3-4): 231-4; Jansson L, Holmdahl R.; Arthritis Rheum 2001 September; 44(9):2168-75; and Purdie D W. Br *Med Bull* 2000; 56(3):809-23. Also, see Merck Manual, 17th edition, pp. 449-451.

When used in combination to treat arthritic conditions, the compound of formula I can be used with any of the drugs disclosed herein as useful for combination therapy, or can be used with drugs known to treat or prevent arthritic conditions, such as corticosteroids, cytoxic drugs (or other disease modifying or remission inducing drugs), gold treatment, methotrexate, NSAIDs, and COX-2 inhibitors.

In another embodiment, the compound of the present invention can be used to treat conditions in a female individual which are caused by androgen deficiency or which can be ameliorated by androgen replacement, including, but not limited to, osteoporosis, osteopenia, aging skin, glucocorticoid-induced osteoporosis, postmenopausal symptoms, periodontal disease, HIV-wasting, cancer cachexia, obesity, anemias, such as for example, aplastic anemia, muscular dystrophies, Alzheimer's disease, premature ovarian failure, cognitive decline, sexual dysfunction, depression, inflammatory arthritis and joint repair, atherosclerosis, and autoimmune disease, alone or in combination with other active agents. Treatment is effected by administration of a therapeutically effective amount of a compound of structural formula I to a female individual in need of such treatment.

The compound of formula I is also useful in the enhancement of muscle tone in mammals, such as for example, humans. The amorphous and crystalline forms of the compound of structural formula I can also be employed as adjuncts to traditional androgen depletion therapy in the treatment of prostate cancer to restore bone, minimize bone loss, and maintain bone mineral density. In this manner, they can be employed together with traditional androgen deprivation therapy, including GnRH agonists/antagonists, such as those disclosed in P. Limonta, et al., *Exp. Opin. Invest. Drugs,* 10: 709-720 (2001); H. J. Stricker, *Urology,* 58 (Suppl. 2A): 24-27 (2001); R. P. Millar, et al., *British Medical Bulletin,* 56: 761-772 (2000); and A. V. Schally et al., *Advanced Drug Delivery Reviews,* 28: 157-169 (1997). The solid state forms of the compound of formula I can be used in combination with antiandrogens, such as flutamide, 2-hydroxyflutamide (the active metabolite of flutamide), nilutamide, and bicalutamide (Casodex™) in the treatment of prostate cancer.

Further, the present invention can also be employed in the treatment of pancreatic cancer, either for their androgen antagonist properties or as an adjunct to an antiandrogen, such as flutamide, 2-hydroxyflutamide (the active metabolite of flutamide), nilutamide, and bicalutamide (Casodex™).

The term "treating cancer" or "treatment of cancer" refers to administration to a mammal afflicted with a cancerous condition and refers to an effect that alleviates the cancerous condition by killing the cancerous cells, but also to an effect which results in the inhibition of growth and/or metastasis of the cancer.

The compound of structural formula I can minimize the negative effects on lipid metabolism which may exhibit advantages over existing approaches for hormone replacement therapy in hypogonadic (androgen deficient) male individuals.

Additionally, the compound of structural formula I can increase the number of blood cells, such as red blood cells and platelets, and can be used for treatment of hematopoietic disorders, such as aplastic anemia.

In one embodiment of the invention, therapeutically effective amounts of the amorphous, polymorphic, and pseudopolymorphic forms of the compound of formula I, either alone or in combination, are administered to the mammal, to treat or improve disorders selected from enhancement of weakened muscle tone, osteoporosis, osteopenia, glucocorticoid-induced osteoporosis, periodontal disease, bone fracture, bone damage following bone reconstructive surgery, sarcopenia, frailty, aging skin, male hypogonadism, postmenopausal symptoms in women, atherosclerosis, hypercholesterolemia, hyperlipidemia, obesity, aplastic anemia and other hematopoietic disorders, pancreatic cancer, inflammatory arthritis and joint repair, HIV-wasting, prostate cancer, benign prostatic hyperplasia (BPH), cancer cachexia, Alzheimer's disease, muscular dystrophies, cognitive decline, sexual dysfunction, sleep apnea, depression, premature ovarian failure, and autoimmune disease.

In another embodiment, therapeutically effective amounts of the amorphous or crystalline forms of the compound of formula I, either alone or in combination, can be used to treat or improve a disorder selected from weakened muscle tone, osteoporosis, osteopenia, glucocorticoid-induced osteoporosis, periodontal disease, bone fracture, bone damage following bone reconstructive surgery, sarcopenia, Alzheimer's disease, and frailty.

In another embodiment, the amorphous and crystalline forms of the compound in accordance with the invention can be used to treat or improve a disorder such as male hypogonadism, postmenopausal symptoms in women, atherosclerosis, hypercholesterolemia, hyperlipidemia, obesity, aplastic anemia and other hematopoietic disorders, pancreatic cancer, inflammatory arthritis and joint repair, HIV-wasting, prostate cancer, benign prostatic hyperplasia (BPH), cancer cachexia, muscular dystrophies, cognitive decline, sexual dysfunction, sleep apnea, depression, premature ovarian failure, and autoimmune disease.

The solid state forms of the compound in accordance with the present invention can be administered in their enantiomerically pure form. Racemic mixtures can be separated into their individual enantiomers by any of a number of conventional methods. These include chiral chromatography, derivatization with a chiral auxiliary followed by separation by chromatography or crystallization, and fractional crystallization of diastereomeric salts.

As used herein, the compound of formula I of the present invention which functions as an "agonist" of the androgen receptor can bind to the androgen receptor and initiate a physiological or a pharmacological response characteristic of that receptor. The term "tissue-selective androgen receptor modulator" refers to an androgen receptor ligand that mimics the action of a natural ligand in some tissues but not in others. A "partial agonist" is an agonist which is unable to induce maximal activation of the receptor population, regardless of the amount of compound applied. A "full agonist" induces full activation of the androgen receptor population at a given concentration. A compound of formula I which functions as an "antagonist" of the androgen receptor can bind to the androgen receptor and block or inhibit the androgen-associated responses normally induced by a natural androgen receptor ligand.

The term "therapeutically effective amount" means the amount the compound of structural formula I that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts.

By "pharmaceutically acceptable" it is meant that the carrier, diluent or excipient must be compatible with the other ingredients of the formulation and not be deleterious to the recipient thereof.

The terms "administration of a compound" and "administering a compound" should be understood to mean providing a compound of the invention or a prodrug of a compound of the invention to the individual in need of treatment.

By the term "modulating a function mediated by the androgen receptor in a tissue selective manner" it is meant modulating a function mediated by the androgen receptor selectively (or discriminately) in anabolic (bone and/or muscular) tissue (bone and muscular) in the absence of such modulation at androgenic (reproductive) tissue, such as the prostate, testis, seminal vesicles, ovary, uterus, and other sex accessory tissues. In one embodiment, the function of the androgen receptor in anabolic tissue is activated whereas the function of the androgen receptor in androgenic tissue is blocked or suppressed. In another embodiment, the function of the androgen receptor in anabolic tissue is blocked or suppressed whereas the function of the androgen receptor in androgenic tissue is activated.

The administration of an amorphous or crystalline form of the compound of structural formula I, in order to practice the present methods of therapy, is carried out by administering an effective amount of the compound to the patient in need of such treatment or prophylaxis. The need for a prophylactic administration according to the methods of the present invention is determined via the use of well-known risk factors. The effective amount of an individual compound is determined, in the final analysis, by the physician in charge of the case, but depends on factors such as the exact disease to be treated, the severity of the disease and other diseases or conditions from which the patient suffers, the chosen route of administration, other drugs and treatments which the patient can concomitantly require, and other factors in the physician's judgment.

If formulated as a fixed dose, such combination products employ the amorphous and crystalline forms of the compound of formula I within the dosage range described below and the other pharmaceutically active agent(s) within its approved dosage range. The amorphous and crystalline forms of the compound can alternatively be used sequentially with known pharmaceutically acceptable agent(s) when a combination formulation is inappropriate.

Generally, the daily dosage of an amorphous or crystalline form of the compound of structural formula I can be varied over a wide range from about 0.01 to about 1000 mg per adult human per day. For example, dosages range from about 0.1 to about 200 mg/day. For oral administration, the compositions can be provided in the form of tablets containing from about 0.01 to about 1000 mg, such as for example, 0.01, 0.05, 0.1, 0.5, 1.0, 2.5, 3.0, 5.0, 6.0, 10.0, 15.0, 25.0, 50.0, 75, 100, 125, 150, 175, 180, 200, 225, and 500 milligrams of the active ingredient for the symptomatic adjustment of the dosage to the mammal to be treated.

The dose can be administered in a single daily dose or the total daily dosage can be administered in divided doses of two, three or four times daily. Furthermore, based on the properties of the individual compound selected for administration, the dose can be administered less frequently, e.g., weekly, twice weekly, monthly, etc. The unit dosage will, of course, be correspondingly larger for the less frequent administration.

When administered via intranasal routes, transdermal routes, by rectal or vaginal suppositories, or through an intravenous solution, the dosage administration will, of course, be continuous rather than intermittent throughout the dosage regimen.

Exemplifying the invention is a pharmaceutical composition comprising any of the amorphous and crystalline forms of the compound, either alone or in combination, described above and a pharmaceutically acceptable carrier. An illustration of the invention is a process for making a pharmaceutical composition comprising combining one or more of the amorphous or crystalline forms of the compound of formula with a pharmaceutically acceptable carrier.

Formulations of the tissue-selective androgen receptor modulator employed for medical use comprise an amorphous or crystalline solid form of the compound of formula I together with an acceptable carrier thereof and optionally other therapeutically active ingredients. The carrier must be pharmaceutically acceptable in the sense of being compatible with the other ingredients of the formulation and not being deleterious to the recipient subject of the formulation.

The present invention, therefore, further provides a pharmaceutical formulation comprising amorphous or crystalline forms of the compound of structural formula I together with a pharmaceutically acceptable carrier thereof. The formulations include those suitable for oral, rectal, intravaginal, intranasal, topical and parenteral (including subcutaneous, intramuscular and intravenous administration). In one embodiment, the formulations are those suitable for oral administration.

Suitable topical formulations of a compound of formula I include transdermal devices, aerosols, creams, solutions, ointments, gels, lotions, dusting powders, and the like. The topical pharmaceutical compositions containing the compounds of the present invention ordinarily include about 0.005% to about 5% by weight of the active compound in admixture with a pharmaceutically acceptable vehicle. Transdermal skin patches useful for administering the compounds of the present invention include those well known to those of ordinary skill in that art.

The formulations can be presented in a unit dosage form and can be prepared by any of the methods known in the art of pharmacy. All methods include the step of bringing the active compound in association with a carrier, which constitutes one or more ingredients. In general, the formulations are prepared by uniformly and intimately bringing the active compound in association with a liquid carrier, a waxy solid carrier or a finely divided solid carrier, and then, if needed, shaping the product into the desired dosage form.

Formulations of the present invention suitable for oral administration can be presented as discrete units such as capsules, cachets, tablets or lozenges, each containing a predetermined amount of the active compound; as a powder or granules; or a suspension or solution in an aqueous liquid or non-aqueous liquid, e.g., a syrup, an elixir, or an emulsion.

A tablet can be made by compression or molding, optionally with one or more accessory ingredients. Compressed tablets can be prepared by compressing in a suitable machine the active compound in a free flowing form, e.g., a powder or granules, optionally mixed with accessory ingredients, e.g., binders, lubricants, inert diluents, disintegrating agents or coloring agents. Molded tablets can be made by molding in a suitable machine a mixture of the active compound, preferably in powdered form, with a suitable carrier. Suitable binders include, without limitation, starch, gelatin, natural sugars such as glucose or beta-lactose, corn sweeteners, natural and synthetic gums such as acacia, tragacanth or sodium alginate, carboxymethyl-cellulose, polyethylene glycol, waxes and the like. Non-limiting representative lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

Oral liquid forms, such as syrups or suspensions in suitably flavored suspending or dispersing agents such as the synthetic and natural gums, for example, tragacanth, acacia, methyl cellulose and the like, can be made by adding the active compound to the solution or suspension. Additional dispersing agents which can be employed include glycerin and the like.

Formulations for vaginal or rectal administration can be presented as a suppository with a conventional carrier, i.e., a base that is nontoxic and nonirritating to mucous membranes, compatible with a compound of structural formula I, and is stable in storage and does not bind or interfere with the release of the amorphous or crystalline forms of the compound of formula I. Suitable bases include: cocoa butter (theobroma oil), polyethylene glycols (such as carbowax and polyglycols), glycol-surfactant combinations, polyoxyl 40 stearate, polyoxyethylene sorbitan fatty acid esters (such as Tween, Myrj, and Arlacel), glycerinated gelatin, and hydrogenated vegetable oils. When glycerinated gelatin suppositories are used, a preservative such as methylparaben or propylparaben can be employed.

Topical preparations containing the active drug component can be admixed with a variety of carrier materials well known in the art, such as, e.g., alcohols, aloe vera gel, allantoin, glycerine, vitamin A and E oils, mineral oil, PPG2 myristyl propionate, and the like, to form, e.g., alcoholic solutions, topical cleansers, cleansing creams, skin gels, skin lotions, and shampoos in cream or gel formulations.

The amorphous and crystalline forms of N-(3H-imidazo [4,5-b]pyridin-2-ylmethyl)-2-fluoro-4-methyl-3-oxo-4-aza-5-alpha-androst-1-en-17-beta-carboxamide of present invention can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The SARM of the present invention can also be delivered by the use of monoclonal antibodies as individual carriers to which the compound molecules are coupled. The compound of the present invention can also be coupled with soluble polymers as targetable drug carriers. Such polymers can include polyvinyl-pyrrolidone, pyran copolymer, polyhydroxypropylmethacrylamide-phenol, polyhydroxy-ethylaspartamidephenol, or polyethylene-oxide polylysine substituted with palmitoyl residues. Furthermore, the compound of the present invention can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

Formulations suitable for parenteral administration include formulations that comprise a sterile aqueous preparation of the active compound which can be isotonic with the blood of the recipient. Such formulations suitably comprise a solution or suspension of a compound that is isotonic with the blood of the recipient subject. Such formulations can contain distilled water, 5% dextrose in distilled water or saline and the active compound. Useful formulations also comprise concentrated solutions or solids comprising the solid state form of the compound of formula I which on dilution with an appropriate solvent give a solution suitable for parenteral administration.

The pharmaceutical composition and method of the present invention can further comprise other therapeutically active compounds usually applied in the treatment of the above mentioned conditions, including osteoporosis, periodontal disease, bone fracture, bone damage following bone reconstructive surgery, sarcopenia, frailty, aging skin, male hypogonadism, post-menopausal symptoms in women, atherosclerosis, hypercholesterolemia, hyperlipidemia, hematopoietic disorders, such as for example, aplastic anemia, pancreatic cancer, Alzheimer's disease, inflammatory arthritis, and joint repair.

For the treatment and prevention of osteoporosis, the solid state forms of N-(3H-imidazo[4,5-b]pyridin-2-ylmethyl)-2-fluoro-4-methyl-3-oxo-4-aza-5-alpha-androst-1-en-17-beta-carboxamide of the present invention can be administered in combination with at least one bone-strengthening agent selected from antiresorptive agents, osteoanabolic agents, and other agents beneficial for the skeleton through mechanisms which are not precisely defined, such as calcium supplements, flavonoids, and vitamin D analogs. The conditions of periodontal disease, bone fracture, and bone damage following bone reconstructive surgery can also benefit from these combined treatments. For example, the amorphous and crystalline forms of the compound of the instant invention can be effectively administered in combination with effective amounts of other agents such as estrogens, bisphosphonates, SERMs, cathepsin K inhibitors, αvβ3 integrin receptor antagonists, vacuolar ATPase inhibitors, the polypeptide osteoprotegerin, antagonists of VEGF, thiazolidinediones, calcitonin, protein kinase inhibitors, parathyroid hormone (PTH) and analogs, calcium receptor antagonists, growth hormone secretagogues, growth hormone releasing hormone, insulin-like growth factor, bone morphogenetic protein (BMP), inhibitors of BMP antagonism, prostaglandin derivatives, fibroblast growth factors, vitamin D and derivatives thereof, vitamin K and derivatives thereof, soy isoflavones, calcium salts, and fluoride salts. The conditions of periodontal disease, bone fracture, and bone damage following bone reconstructive surgery can also benefit from these combined treatments.

In one embodiment of the present invention, the amorphous and crystalline forms of the compound of the instant invention can be effectively administered in combination with an effective amount of at least one bone-strengthening agent chosen from estrogen, and estrogen derivatives, alone or in combination with progestin or progestin derivatives; bisphosphonates; antiestrogens or selective estrogen receptor modulators; αvβ3 integrin receptor antagonists; cathepsin K inhibitors; osteoclast vacuolar ATPase inhibitors; calcitonin; and osteoprotegerin.

In the treatment of osteoporosis, the activity of the various solid state forms of the compound of the present invention are distinct from that of the anti-resorptive agents: estrogens, bisphosphonates, SERMs, calcitonin, cathepsin K inhibitors, vacuolar ATPase inhibitors, agents interfering with the RANK/RANKL/Osteoprotegerin pathway, p38 inhibitors or any other inhibitors of osteoclast generation or osteoclast activation. Rather than inhibiting bone resorption, the SARM of the present invention aids in the stimulation of bone formation, acting, for example, on cortical bone, which is responsible for a significant part of bone strength. The thickening of cortical bone substantially contributes to a reduction in fracture risk, especially fractures of the hip. The combination of the tissue-SARM of structural formula I with anti-resorptive agents such as for example estrogen or estrogen derivatives, bisphosphonates, antiestrogens, SERMs, calcitonin, αvβ3 integrin receptor antagonists, HMG-CoA reductase inhibitors, vacuolar ATPase inhibitors, and cathepsin K inhibitors is particularly useful due to the complementary effect of the bone anabolic and antiresorptive actions.

Non-limiting representatives of estrogen and estrogen derivatives include steroidal compounds having estrogenic activity such as, for example, 17β-estradiol, estrone, conjugated estrogen (PREMARIN®), equine estrogen, 17β-ethynyl estradiol, and the like. The estrogen or estrogen derivative can be employed alone or in combination with a progestin or progestin derivative. Nonlimiting examples of progestin derivatives are norethindrone and medroxyprogesterone acetate.

Non-limiting examples of bisphosphonate compounds which can also be employed in combination with a compound of the present invention include:

(a) alendronate (also known as alendronic acid, 4-amino-1-hydroxybutylidene-1,1-bisphosphonic acid, alendronate sodium, alendronate monosodium trihydrate or 4-amino-1-hydroxybutylidene-1,1-bisphosphonic acid monosodium trihydrate. Alendronate is described in U.S. Pat. No. 4,922,007, to Kieczykowski et al., issued May 1, 1990; U.S. Pat. No. 5,019,651, to Kieczykowski, issued May 28, 1991; U.S. Pat. No. 5,510,517, to Dauer et al., issued Apr. 23, 1996; U.S. Pat. No. 5,648,491, to Dauer et al., issued Jul. 15, 1997;

(b) [(cycloheptylamino)-methylene]-bis-phosphonate (incadronate), which is described in U.S. Pat. No. 4,970,335, to Isomura et al., issued Nov. 13, 1990;

(c) (dichloromethylene)-bis-phosphonic acid (clodronic acid) and the disodium salt (clodronate), which are described in Belgium Patent 672,205 (1966) and *J. Org. Chem* 32, 4111 (1967);

(d) [1-hydroxy-3-(1-pyrrolidinyl)-propylidene]-bis-phosphonate (EB-1053);

(e) (1-hydroxyethylidene)-bis-phosphonate (etidronate);

(f) [1-hydroxy-3-(methylpentylamino)propylidene]-bis-phosphonate (ibandronate), which is described in U.S. Pat. No. 4,927,814, issued May 22, 1990;

(g) (6-amino-1-hydroxyhexylidene)-bis-phosphonate (neridronate);

(h) [3-(dimethylamino)-1-hydroxypropylidene]-bis-phosphonate (olpadronate);
(i) (3-amino-1-hydroxypropylidene)-bis-phosphonate (pamidronate);
(j) [2-(2-pyridinyl)ethylidene]-bis-phosphonate (piridronate), which is described in U.S. Pat. No. 4,761,406;
(k) [1-hydroxy-2-(3-pyridinyl)-ethylidene]-bis-phosphonate (risedronate);
(l) {[(4-chlorophenyl)thio]methylene}-bis-phosphonate (tiludronate), which is described in U.S. Pat. No. 4,876,248, to Breliere et al., Oct. 24, 1989;
(m) [1-hydroxy-2-(1H-imidazol-1-yl)ethylidene]-bis-phosphonate (zoledronate); and
(n) [1-hydroxy-2-imidazopyridin-(1,2-a)-3-ylethylidene]-bis-phosphonate (minodronate).

In one embodiment of the methods and compositions of the present invention, the bisphosphonate is chosen from alendronate, clodronate, etidronate, ibandronate, incadronate, minodronate, neridronate, olpadronate, pamidronate, piridronate, risedronate, tiludronate, zoledronate, pharmaceutically acceptable salts of these bisphosphonates, and mixtures thereof. In one variant, the bisphosphonate is selected from alendronate, risedronate, zoledronate, ibandronate, tiludronate, and clodronate. In a subclass of this class, the bisphosphonate is alendronate, pharmaceutically acceptable salts and hydrates thereof, and mixtures thereof. A particular pharmaceutically acceptable salt of alendronate is alendronate monosodium. Pharmaceutically acceptable hydrates of alendronate monosodium include the monohydrate and the trihydrate. A particular pharmaceutically acceptable salt of risedronate is risedronate monosodium. Pharmaceutically acceptable hydrates of risedronate monosodium include the hemi-pentahydrate.

Still further, antiestrogenic compounds such as raloxifene (see, e.g., U.S. Pat. No. 5,393,763), clomiphene, zuclomiphene, enclomiphene, nafoxidene, CI-680, CI-628, CN-55, 945-27, Mer-25, U-11,555A, U-100A, and salts thereof, and the like (see, e.g., U.S. Pat. Nos. 4,729,999 and 4,894,373) can be employed in combination with a compound of structural formula I in the methods and compositions of the present invention. These agents are also known as SERMs, or selective estrogen receptor modulators, agents known in the art to prevent bone loss by inhibiting bone resorption via pathways believed to be similar to those of estrogens.

Non-limiting representatives of SERMs include, for example, tamoxifen, raloxifene, lasofoxifene, toremifene, azorxifene, EM-800, EM-652, TSE 424, clomiphene, droloxifene, idoxifene, and levormeloxifene [Goldstein, et al., "A pharmacological review of selective estrogen receptor modulators," *Human Reproduction Update*, 6: 212-224 (2000); Lufkin, et al., *Rheumatic Disease Clinics of North America*, 27: 163-185 (2001), and "Targeting the Estrogen Receptor with SERMs," *Ann. Rep. Med. Chem.* 36: 149-158 (2001)].

αvβ3 Integrin receptor antagonists suppress bone resorption and can be employed in combination with the SARM of structural formula I for the treatment of bone disorders including osteoporosis. For example, reference is made to W. J. Hoekstra and B. L. Poulter, *Curr. Med. Chem.* 5: 195-204 (1998) and references cited therein. Other αvβ3 antagonists are described in R. M. Keenan et al., *J. Med. Chem.* 40: 2289-2292 (1997); R. M. Keenan et al., *Bioorg. Med. Chem. Lett.* 8: 3165-3170 (1998); and R. M. Keenan et al., *Bioorg. Med. Chem. Lett.* 8: 3171-3176 (1998).

Cathepsin K, formerly known as cathepsin O2, is a cysteine protease and is described in PCT International Application Publication No. WO 96/13523; U.S. Pat. Nos. 5,501,969 and 5,736,357. Cysteine proteases, specifically cathepsins, are linked to a number of disease conditions, such as tumor metastasis, inflammation, arthritis, and bone remodeling. At acidic pH's, cathepsins can degrade type-I collagen. Cathepsin protease inhibitors can inhibit osteoclastic bone resorption by inhibiting the degradation of collagen fibers and are thus useful in the treatment of bone resorption diseases, such as osteoporosis. Non-limiting examples of cathespin K inhibitors can be found in PCT International Publications WO 01/49288 and WO 01/77073.

Members of the class of HMG-CoA reductase inhibitors, known as the "statins," have been found to trigger the growth of new bone, replacing bone mass lost as a result of osteoporosis (see *The Wall Street Journal*, Friday, Dec. 3, 1999, page B1). Therefore, the statins hold promise for the treatment of bone resorption. Examples of HMG-CoA reductase inhibitors include statins in their and pharmaceutically acceptable salts and esters thereof, including but not limited to lovastatin (U.S. Pat. No. 4,342,767); simvastatin (see U.S. Pat. No. 4,444,784); dihydroxy open-acid simvastatin, particularly the ammonium or calcium salts thereof; pravastatin, particularly the sodium salt thereof (see U.S. Pat. No. 4,346,227); fluvastatin, particularly the sodium salt thereof (see U.S. Pat. No. 5,354,772); atorvastatin, particularly the calcium salt thereof (see U.S. Pat. No. 5,273,995); cerivastatin, particularly the sodium salt thereof (see U.S. Pat. No. 5,177,080), rosuvastatin, also known as ZD4522 (see U.S. Pat. No. 5,260,440) and pitavastatin, also referred to as NK-104, itavastatin, or nisvastatin (see PCT international application publication number WO 97/23200).

Osteoclast vacuolar ATPase inhibitors, also called proton pump inhibitors, can be employed together with the solid forms of the SARM of structural formula I of the present invention. The proton ATPase which is found on the apical membrane of the osteoclast has been reported to play a significant role in the bone resorption process. Therefore, this proton pump represents an attractive target for the design of inhibitors of bone resorption which are potentially useful for the treatment and prevention of osteoporosis and related metabolic diseases [see C. Farina et al., *DDT*, 4: 163-172 (1999)].

The angiogenic factor VEGF has been shown to stimulate the bone-resorbing activity of isolated mature rabbit osteoclasts via binding to its receptors on osteoclasts [see M. Nakagawa et al., *FEBS Letters*, 473: 161-164 (2000)]. Therefore, the development of antagonists of VEGF binding to osteoclast receptors, such as KDR/Flk-1 and Flt-1, can provide yet a further approach to the treatment or prevention of bone resorption.

Activators of the peroxisome proliferator-activated receptor-γ (PPARγ), such as the thiazolidinediones (TZD's), inhibit osteoclast-like cell formation and bone resorption in vitro. Results reported by R. Okazaki et al. in *Endocrinology*, 140: 5060-5065 (1999) point to a local mechanism on bone marrow cells as well as a systemic one on glucose metabolism. Nonlimiting examples of PPARγ, activators include the glitazones, such as troglitazone, pioglitazone, rosiglitazone, and BRL 49653.

Calcitonin can also be employed together with the SARMs of structural formula I. Calcitonin is preferentially employed as salmon nasal spray (Azra et al., Calcitonin. 1996. In: J. P. Bilezikian, et al., Ed., *Principles of Bone Biology*, San Diego: Academic Press; and Silverman, "Calcitonin," *Rheumatic Disease Clinics of North America*, 27: 187-196, 2001)

Protein kinase inhibitors can also be employed together with the SARMs of structural formula I. Kinase inhibitors include those disclosed in WO 01/17562 and are in one embodiment selected from inhibitors of p38. Non-limiting examples of p38 inhibitors useful in the present invention include SB 203580 [Badger et al., *J. Pharmacol. Exp. Ther.,* 279: 1453-1461 (1996)].

Osteoanabolic agents are those agents that are known to build bone by increasing the production of the bone protein matrix. Such osteoanabolic agents include, for example, parathyroid hormone (PTH) and fragments thereof, such as naturally occurring PTH (1-84), PTH (1-34), analogs thereof, native or with substitutions and particularly parathyroid hormone subcutaneous injection. PTH has been found to increase the activity of osteoblasts, the cells that form bone, thereby promoting the synthesis of new bone (*Modern Drug Discovery,* Vol. 3, No. 8, 2000). An injectable recombinant form of human PTH, Forteo (teriparatide), has received regulatory approval in the U.S. for the treatment of osteoporosis.

Also useful in combination with the SARM of the present invention are calcium receptor antagonists which induce the secretion of PTH as described by Gowen et al., *J. Clin. Invest.* 105: 1595-604 (2000).

Additional osteoanabolic agents include growth hormone secretagogues, growth hormone, growth hormone releasing hormone and the like can be employed with the compounds according to structural formula I for the treatment of osteoporosis. Non-limiting examples of representative growth hormone secretagogues are disclosed in U.S. Pat. Nos. 3,239,345, 4,036,979, 4,411,890, 5,206,235, 5,283,241, 5,284,841, 5,310,737, 5,317,017, 5,374,721, 5,430,144, 5,434,261, 5,438,136, 5,494,919, 5,494,920, 5,492,916 and 5,536,716; European Patent Pub. Nos. 0,144,230 and 0,513,974; articles, *Science,* 260 1640-1643 (Jun. 11, 1993); *Ann. Rep. Med. Chem.,* 28: 177-186 (1993); *Bioorg. Med. Chem. Lett.,* 4: 2709-2714 (1994); and *Proc. Natl. Acad. Sci. USA,* 92: 7001-7005 (1995).

Insulin-like growth factor (IGF) can also be employed together with the SARM of structural formula I. Insulin-like growth factors can be selected from Insulin-like Growth Factor I, alone or in combination with IGF binding protein 3 and IGF II [See Johannson and Rosen, "The IGFs as potential therapy for metabolic bone diseases," 1996, In: Bilezikian, et al., Ed., *Principles of Bone Biology,* San Diego: Academic Press; and Ghiron et al., *J. Bone Miner. Res.* 10: 1844-1852 (1995)].

Bone morphogenetic protein (BMP) can also be employed together with the SARMs of structural formula I. Bone morphogenetic protein includes BMP 2, 3, 5, 6, 7, as well as related molecules TGF beta and GDF 5 [Rosen et al., "Bone morphogenetic proteins," 1996. In: J. P. Bilezikian, et al., Ed., *Principles of Bone Biology,* San Diego: Academic Press; and Wang E A, *Trends Biotechnol.,* 11: 379-383 (1993)].

Inhibitors of BMP antagonism can also be employed together with the SARM of structural formula I. In one embodiment, BMP antagonist inhibitors are chosen from inhibitors of the BMP antagonists SOST, noggin, chordin, gremlin, and dan [see Massague and Chen, "Controlling TGF-beta signaling," *Genes Dev.,* 14: 627-644, 2000; Aspenberg et al., *J. Bone Miner. Res.* 16: 497-500, 2001; and Brunkow et al., *Am. J. Hum. Genet.* 68: 577-89 (2001)].

The tissue-selective androgen receptor modulators of the present invention can also be combined with the polypeptide osteoprotegerin for the treatment of conditions associated with bone loss, such as osteoporosis. The osteoprotegerin can be selected from mammalian osteoprotegerin and human osteoprotegerin. The polypeptide osteoprotegerin, a member of the tumor necrosis factor receptor super-family, is useful to treat bone diseases characterized by increased bone loss, such as osteoporosis. Reference is made to U.S. Pat. No. 6,288,032.

Prostaglandin derivatives can also be employed together with the SARMs of structural formula I. Non-limiting representatives of prostaglandin derivatives are selected from agonists of prostaglandin receptors EP1, EP2, EP4, FP, IP and derivatives thereof [Pilbeam et al., "Prostaglandins and bone metabolism," 1996. In: Bilezikian, et al. Ed. Principles of Bone Biology, San Diego: Academic Press; Weinreb et al., *Bone,* 28: 275-281 (2001)].

Fibroblast growth factors can also be employed together with the SARMs of structural formula I. Fibroblast growth factors include aFGF, bFGF and related peptides with FGF activity [Hurley Florkiewicz, "Fibroblast growth factor and vascular endothelial growth factor families," 1996. In: J. P. Bilezikian, et al., Ed. Principles of Bone Biology, San Diego: Academic Press].

In addition to bone resorption inhibitors and osteoanabolic agents, there are also other agents known to be beneficial for the skeleton through mechanisms which are not precisely defined. These agents can also be favorably combined with the SARMs of structural formula I.

Vitamin D, vitamin D derivatives and analogs can also be employed together with the SARMs of structural formula I. Vitamin D and vitamin D derivatives include, for example, $D_3$ (cholecaciferol), $D_2$ (ergocalciferol), 25-OH-vitamin $D_3$, $1\alpha,25(OH)_2$ vitamin $D_3$, $1\alpha$-OH-vitamin $D_3$, $1\alpha$-OH-vitamin $D_2$, dihydrotachysterol, 26,27-F6-$1\alpha,25(OH)_2$ vitamin $D_3$, 19-nor-$1\alpha,25(OH)_2$ vitamin $D_3$, 22-oxacalcitriol, calcipotriol, $1\alpha,25(OH)_2$-16-ene-23-yne-vitamin $D_3$ (Ro 23-7553), EB1089, 20-epi-$1\alpha,25(OH)_2$ vitamin $D_3$, KH1060, ED71, $1\alpha,24(S)$-$(OH)_2$ vitamin $D_3$, $1\alpha,24(R)$—$(OH)_2$ vitamin $D_3$ [See, Jones G., "Pharmacological mechanisms of therapeutics: vitamin D and analogs," 1996. In: J. P. Bilezikian, et al. Ed. Principles of Bone Biology, San Diego: Academic Press].

Vitamin K and Vitamin K derivatives can also be employed together with the various solid forms of the SARM of the present invention. Vitamin K and vitamin K derivatives include menatetrenone (vitamin $K_2$) [see Shiraki et al., *J. Bone Miner. Res.,* 15: 515-521 (2000)].

Soy isoflavones, including ipriflavone, can be employed together with the SARM of the present invention.

Fluoride salts, including sodium fluoride (NaF) and monosodium fluorophosphate (MFP), can also be employed together with the SARM of structural formula I. Dietary calcium supplements can also be employed together with the SARM of structural formula I. Dietary calcium supplements include calcium carbonate, calcium citrate, and natural calcium salts (Heaney. Calcium. 1996. In: J. P. Bilezikian, et al., Ed., Principles of Bone Biology, San Diego: Academic Press).

Daily dosage ranges for bone resorption inhibitors, osteoanabolic agents and other agents which can be used to benefit the skeleton when used in combination with a compound of structural formula I are those which are known in the art. In such combinations, generally the daily dosage range for the SARM of structural formula I ranges from about 0.01 to about 1000 mg per adult human per day, such as for example, from about 0.1 to about 200 mg/day. However, adjustments to decrease the dose of each agent can be made due to the increased efficacy of the combined agent.

In particular, when a bisphosphonate is employed, dosages from about 2.5 to about 100 mg/day (measured as the free bisphosphonic acid) are appropriate for treatment, such as for example ranging from 5 to 20 mg/day, or about 10 mg/day. Prophylactically, doses of about 2.5 to about 10 mg/day and especially about 5 mg/day should be employed. For reduction in side-effects, it can be desirable to administer the combination of a compound of structural formula I and the bisphosphonate once a week. For once weekly administration, doses ranging from about 15 mg to about 700 mg per week of bisphosphonate and from about 0.07 to about 7000 mg of a compound of structural formula I can be employed, either separately, or in a combined dosage form. A compound of structural formula I can be favorably administered in a controlled-release delivery device, particularly for once weekly administration.

For the treatment of atherosclerosis, hypercholesterolemia, and hyperlipidemia, the compound of structural formula I can be effectively administered in combination with one or more additional active agents. The additional active agent or agents can be chosen from lipid-altering compounds such as HMG-CoA reductase inhibitors, agents having other pharmaceutical activities, and agents that have both lipid-altering effects and other pharmaceutical activities. Non-limiting examples of HMG-CoA reductase inhibitors include statins in their lactonized or dihydroxy open acid forms and pharmaceutically acceptable salts and esters thereof, including but not limited to lovastatin (see U.S. Pat. No. 4,342,767); simvastatin (see U.S. Pat. No. 4,444,784); dihydroxy open-acid simvastatin, particularly the ammonium or calcium salts thereof; pravastatin, particularly the sodium salt thereof (see U.S. Pat. No. 4,346,227); fluvastatin, particularly the sodium salt thereof (see U.S. Pat. No. 5,354,772); atorvastatin, particularly the calcium salt thereof (see U.S. Pat. No. 5,273,995); cerivastatin, particularly the sodium salt thereof (see U.S. Pat. No. 5,177,080), and nisvastatin, also referred to as NK-104 (see PCT international application publication number WO 97/23200).

Additional active agents which can be employed in combination with the compound of structural formula I include, but are not limited to, HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; cholesterol absorption inhibitors, such as SCH-58235, also known as ezetimibe and 1-(4-fluorophenyl)-3(R)-[3(S)-(4-fluorophenyl)-3-hydroxypropyl)]-4(S)-(4-hydroxyphenyl)-2-azetidinone, which is described in U.S. Pat. Nos. 5,767,115 and 5,846,966; bile acid sequestrants; LDL (low density lipoprotein) receptor inducers; platelet aggregation inhibitors, for example glycoprotein IIb/IIIa fibrinogen receptor antagonists and aspirin; human peroxisome proliferator activated receptor gamma (PPARγ), agonists, including the compounds commonly referred to as glitazones, for example troglitazone, pioglitazone and rosiglitazone and, including those compounds included within the structural class known as thiazolidinediones as well as those PPARγ, agonists outside the thiazolidinedione structural class; PPARα agonists, such as clofibrate, fenofibrate including micronized fenofibrate, and gemfibrozil; PPAR dual α/γ agonists; vitamin $B_6$ (also known as pyridoxine) and the pharmaceutically acceptable salts thereof such as the HCl salt; vitamin $B_{12}$ (also known as cyanocobalamin); folic acid or a pharmaceutically acceptable salt or ester thereof such as the sodium salt and the methylglucamine salt; anti-oxidant vitamins such as vitamin C and E and beta carotene; beta-blockers; angiotensin II antagonists such as losartan; angiotensin converting enzyme inhibitors, such as enalapril and captopril; calcium channel blockers, such as nifedipine and diltiazem; endothelin antagonists; agents such as LXR ligands that enhance ABC1 gene expression; bisphosphonate compounds, such as alendronate sodium; and cyclooxygenase-2 inhibitors, such as rofecoxib and celecoxib, as well as other agents known to be useful in the treatment of these conditions.

Daily dosage ranges for HMG-CoA reductase inhibitors when used in combination with the compound of structural formula I correspond to those which are known in the art. Similarly, daily dosage ranges for the HMG-CoA synthase inhibitors; squalene epoxidase inhibitors; squalene synthetase inhibitors (also known as squalene synthase inhibitors), acyl-coenzyme A: cholesterol acyltransferase (ACAT) inhibitors including selective inhibitors of ACAT-1 or ACAT-2 as well as dual inhibitors of ACAT-1 and -2; microsomal triglyceride transfer protein (MTP) inhibitors; probucol; niacin; cholesterol absorption inhibitors including ezetimibe; bile acid sequestrants; LDL (low density lipoprotein) receptor inducers; platelet aggregation inhibitors, including glycoprotein IIb/IIIa fibrinogen receptor antagonists and aspirin; human peroxisome proliferator activated receptor gamma (PPARγ) agonists; PPARα agonists; PPAR dual α/γ agonists; vitamin $B_6$; vitamin $B_{12}$; folic acid; anti-oxidant vitamins; beta-blockers; angiotensin II antagonists; angiotensin converting enzyme inhibitors; calcium channel blockers; endothelin antagonists; agents such as LXR ligands that enhance ABC1 gene expression; bisphosphonate compounds; and cyclooxygenase-2 inhibitors also correspond to those which are known in the art, although due to the combined action with the compounds of structural formula I, the dosage can be somewhat lower when administered in combination.

One embodiment of the invention is a method for affecting a bone turnover marker in a mammal comprising administering a therapeutically effective amount of the compound according to formula I. Non-limiting examples of bone turnover markers can be selected from urinary C-telopeptide degradation products of type I collagen (CTX), urinary N-telopeptide cross-links of type I collagen (NTX), osteocalcin (bone G1a protein), dual energy x-ray absorptionmetry (DXA), bone specific alkaline phosphatase (BSAP), quantitative ultrasound (QUS), and deoxypyridinoline (DPD) crosslinks.

In accordance with the method of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating diseases caused by androgen deficiency or that can be ameliorated by addition of androgen.

Abbreviations Used in the Description of the Preparation of the Compounds of the Present Invention:

| | |
|---|---|
| AcOH | Acetic acid |
| CBZ-glycine | Protected from of glycine ($C_{10}H_{11}NO_4$) |
| DHT | Dihydrotestosterone |
| DMEM | Dulbecceo modified eagle media |
| DMSO | Dimethyl sulfoxide |

| | |
|---|---|
| DMF | N,N-Dimethylformamide |
| EDC | 1-(3-Dimethylaminopropyl)3-ethylcarbodiimide HCl |
| EDTA | Ethylenediaminetetraacetic acid |
| EtOAc | Ethyl acetate |
| EtOH | Ethanol |
| FBS | Fetal bovine serum |
| FCS | Fetal calf serum |
| HAP | Hydroxyapatite |
| HEPES | (2-Hydroxyethyl)-1-piperazineethanesulfonic acid |
| HOAt | 1-hydroxy-7-azabenzotriazole |
| HOBt | N-hydroxybenzotriazole |
| HPLC | High-performance liquid chromatography |
| LCMS | Liquid chromotography/mass spectroscopy |
| LDA | Lithium diisopropylamide |
| MeOH | Methanol |
| NMM | N-methylmorpholine |
| n-Bu4NI | Tetra-n-butylammonium iodide |
| Pd/C | Palladium/carbon |
| Rt or rt | Room temperature |
| TEGM | Binding buffer |
| THF | Tetrehydrofuran |

The compounds of this invention may be prepared by employing reactions as shown in the following schemes, in addition to other standard manipulations that are known in the literature or exemplified in the experimental procedures.

EXAMPLE 1

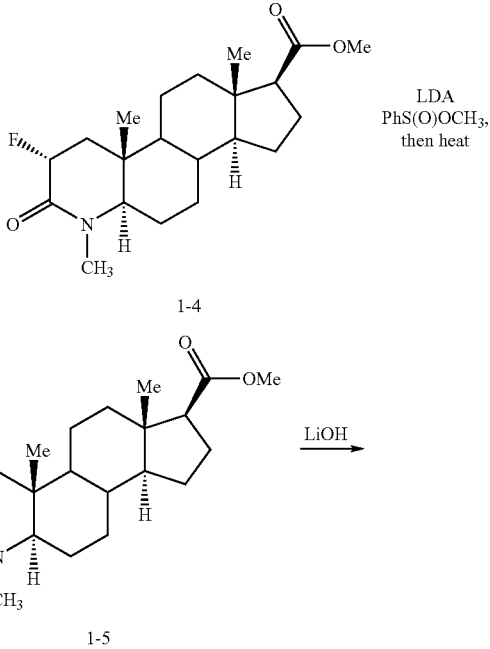

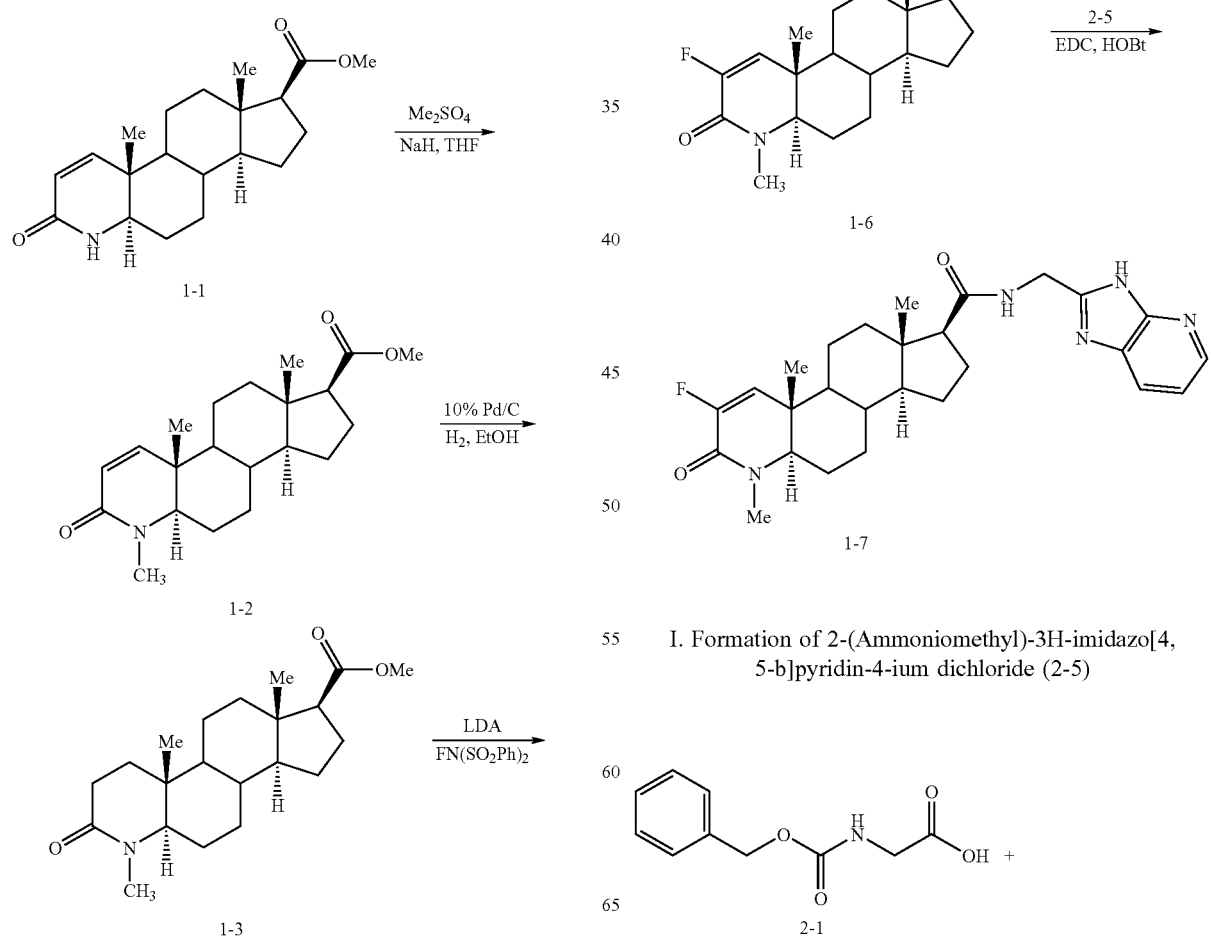

I. Formation of 2-(Ammoniomethyl)-3H-imidazo[4,5-b]pyridin-4-ium dichloride (2-5)

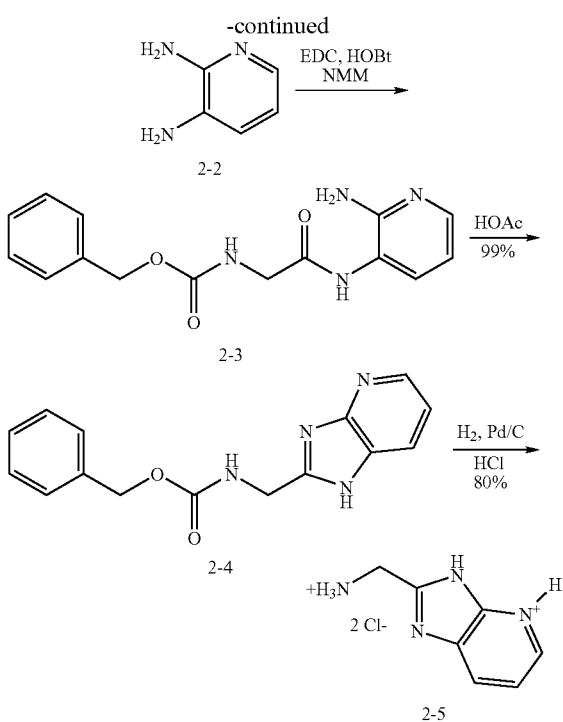

Step I.A: N-(2-aminopyridin-3-yl)-N'-carboxybenzylglycinamide (2-3)

A mixture of 2,3-diaminopyridine, (2-1, 20.866 g, 191.2 mmol), Cbz-glycine (2-2, 40 g, 191.2 mmol), EDC (43.93 g, 229.44 mmol), HOAT (26.02 g, 191.2 mmol) and NMM (82.12 mL, 764.81 mmol) in DMF (300 mL) was stirred for 20 hr. The mixture was diluted with H$_2$O (500 mL) and extracted with EtOAc (3×500 mL). The combined organic portions were washed with sat. NaHCO$_3$, brine, and dried over MgSO$_4$ and then concentrated to give the product 2-3 as a brown solid.

$^1$H NMR (500 MHz, CD$_3$OD) 7.82 (d, 1H, J=5 Hz), 7.49 (d, 1H, J=8 Hz), 7.31 (m, 5H), 6.65 (m, 1H), 5.12 (s, 2H). HRMS (ES, M+1) calc'd 301.1295. found 301.1296.

Step I.B: Benzyl 3H-imidazo[4.5-b]pyridin-2-ylmethylcarbamate (2-4)

The aminopyridine 2-3 (46 g, 153 mmol) was dissolved in 300 mL of AcOH and heated to 120° C. for 20 hours. The reaction mixture was cooled to room temperature and concentrated to give the desired product 2-4 as the acetate salt.
$^1$H NMR (500 MHz, CD$_3$OD) 8.32 (m, 1H), 7.95 (m, 1H), 7.34 (m, 6H), 7.08 (m, 1H), 5.14 (s, 2H), 4.87 (s, 2H). HRMS (ES, M+1) calc'd 283.1190. found 283.1192.

Step I.C: 2-(Ammoniomethyl)-3H-imidazo[4,5-b]pyridin-4-ium dichloride (2-5)

To a mixture of 2-4 (52 g, 151.88 mmol) in 1000 mL of 1:1 AcOH/MeOH was added 20 g 10% Pd/C. The reaction mixture was stirred under 1 atm H$_2$ for 20 hours. The mixture was filtered through a celite pad, concentrated, and then azeotroped with dioxane to give tan oil. The semisolid or thick oil was suspended in 200 mL dioxane and 200 mL 4.0 M HCl/dioxane was added to produce a tan suspension. The solid was collected, washed with dioxane (200 mL) and dried in vacuo to give 2-5 as a tan solid. $^1$H NMR (500 MHz, CD$_3$OD) 8.75 (d, 1H, J=8 Hz), 8367 (d, 1H, J=6 Hz), 7.85 (m, 1H), 4.88 (s, 2H). HRMS (ES, M+1) calc'd 149.0822. found 149.0812.

II. Amorphous Form of N-(3H-imidazo[4,5-b]pyridin-2-ylmethyl)-2-fluoro-4-methyl-3-oxo-4-aza-5-alpha-androst-1-en-17-beta-carboxamide (1-7)

Step II.A: 4-methyl-3-oxo-4-aza-5α-androst-1-ene-17β-carboxylic acid methyl ester (1-2)

A mixture of 1-1 (J. Med. Chem. 29 2298-2315 (1986)) (120 g, 362.04 mmol), 60% NaH (18.7 g, mmol), dimethylsulfate (68.50 g, 543.05 mmol), and THF (1200 mL) was stirred at ambient temperature for 14 hours. Warmed to 60° C. for 2.0 hours and then the reaction was quenched by the slow addition of 40 mL conc. HCl while purging the headspace with nitrogen. Evaporated to ⅕ volume and then diluted with 1500 mL water. The solid was collected, washed with water, hexanes and dried in vacuo to give 1-2 as a pale yellow solid.

Step II.B: 4-methyl-3-oxo-4-aza-5α-androstane-17β-carboxylic acid methyl ester (1-3)

To a solution of 1-2 (20 g, 57.9 mmol) in EtOH (100 mL) was added 10% Pd/C (5.0 g) and the mixture was stirred under 1 atm H$_2$ for 14 hours. The mixture was filtered through a celite pad, concentrated and then dried in vacuo to give 1-3 as a white solid solid.

Step II.C: 2α-Fluoro-4-methyl-3-oxo-4-aza-5α-androstane-17β-carboxylic acid methyl ester (1-4)

To a solution of 1-3 (12 g, 34.53 mmol) in THF (100 mL) at −78° C. was added a solution of 1.5 M LDA in THF (27.6 mL, 41.44 mmol) dropwise over 20 min and then stirred 1 h. A solution of FN(SO$_2$Ph)$_2$ (13.07 g, 41.44 mmol) in THF (40 mL) was then added over 20 min. After 30 min, the cooling bath was removed and the reaction was stirred for 14 h. Et$_2$O was added, and the mixture was washed with water, saturated aqueous sodium hydrogencarbonate, brine, dried (MgSO$_4$) and then concentrated. Chromatography on silica gel (hexanes to EtOAc as eluent) gave 1-4 as a colorless solid.
MS calculated M+H: 366. found 366.1.

Step II.D: 2-Fluoro-4-methyl-3-oxo-4-aza-5α-androst-1-ene-17β-carboxylic acid methyl ester (1-5)

To a solution of 1-4 (30 g, 82.1 mmol) in THF (400 mL) at −78° C. was added a solution of 1.5 M LDA in THF (71.1 mL, 107 mmol) dropwise over 30 min and then stirred 1 h. Methyl benzenesulfinate (19.23 g, 123 mmol) was then added over 15 min. After 30 min, the cooling bath was removed and the reaction was stirred for 1 h. Et$_2$O was added, and the mixture was washed with water, saturated aqueous sodium hydrogencarbonate, brine, dried (MgSO$_4$) and then concentrated. The residue was dissolved in toluene (200 mL) and heated at reflux for 2 h. Solvent evaporation and chromatography of the residue on silica gel (hexanes to 50% EtOAc/hexanes as eluent) gave 1-5 as a pale yellow solid.
MS calculated M+H: 364. found 364.1.

Step II.E: 2-Fluoro-4-methyl-3-oxo-4-aza-5α-androst-1-ene-17β-carboxylic acid (1-6)

To a solution of 1-5 (6.2 g, 17.1 mmol) in 1,4-dioxane (50 mL) was added a solution of lithium hydroxide (1.07 g, 25.6 mmol) in water (30 mL), and the mixture heated at 100° C. for 3 h. After cooling, the mixture was diluted with ethyl acetate, separated, and the organics washed with 1N HCl, brine, dried (MgSO$_4$) and then concentrated to give 1-6 as a pale yellow solid.

MS calculated M+H: 350. found 350.

Step II.F: N-(3H-imidazo[4,5-b]pyridin-2-ylmethyl)-2-fluoro-4-methyl-3-oxo-4-aza-5α-androst-1-en-17β-carboxamide (1-7)

A mixture of 1-6 (15 g, 42.9 mmol), EDC (9.88 g, 51.5 mmol), HOBt (6.96 g, 51.510 mmol), NMM (18.9 mL, 171.70 mmol) and 2-5 (10.43 g, 47.217 mmol) in DMF (200 mL) was heated to 40° C. for 4.0 hours and then stirred at ambient temperature for 14 hr. The mixture was diluted with water, filtered, and the solids washed with water and then dried under vacuum. Chromatography on silica gel (hexanes to 70:25:5 CHCl$_3$/EtOAc/MeOH as eluent) gave 1-7 as a colorless amorphous solid. $^1$H NMR (500 MHz, CDCl$_3$) 8.45 (m, 1H), 7.95 (m, 1H), 7.23 (m, 1H), 6.14 (d, 1H, J=8 Hz), 4.72 (m, 2H), 3.40 (dd, 1H, J=4 Hz, 13 Hz), 2.94 (s, 3H), 2.23 (m, 2H), 1.96 (m, 2H), 1.53-1.86 (m, 7H), 1.25-1.39 (m, 3H), 1.12 (m, 1H), 1.04 (m, 2H), 0.95 (s, 3H), 0.68 (s, 3H). MS calculated M+H: 480.2770. found 480.2740.

EXAMPLE 2

Anhydrous Crystalline Form A of N-(3H-imidazo[4,5-b]pyridin-2-ylmethyl)-2-fluoro-4-methyl-3-oxo-4-aza-5α-androst-1-en-17β-carboxamide The amorphous N-(3H-imidazo[4,5-b]pyridin-2-ylmethyl)-2-fluoro-4-methyl-3-oxo-4-aza-5α-androst-1-en-17β-carboxamide (1-7) was dissolved in 1,2-dimethoxyethane. The solution was heated to reflux. After about 2 minutes, crystallization occurred. The slurry was refluxed for 2 hours, cooled to rt, and filtered. The solid was washed with 1,2-dimethoxyethane and dried to produce the anhydrous crystalline form A of N-(3H-imidazo[4,5-b]pyridin-2-ylmethyl)-2-fluoro-4-methyl-3-oxo-4-aza-5α-androst-1-en-17β-carboxamide.

EXAMPLE 3

Hygroscopic Crystalline Form B of N-(3H-imidazo[4,5-b]pyridin-2-ylmethyl)-2-fluoro-4-methyl-3-oxo-4-aza-5α-androst-1-en-17β-carboxamide Amorphous N-(3H-imidazo[4,5-b]pyridin-2-ylmethyl)-2-fluoro-4-methyl-3-oxo-4-aza-5α-androst-1-en-17β-carboxamide (3.0 gm) (1-7) was dissolved in 5 mL. ethanol with warming. The mixture was allowed to cool to room temperature. After six hours, needles began to form. The mixture was allowed to stand overnight. The precipitated solid was collected and washed with ethanol. The washed solids were allowed to dry for 24 hours.

EXAMPLE 4

Crystalline Hydrate Form C of N-(3H-imidazo[4,5-b]pyridin-2-ylmethyl)-2-fluoro-4-methyl-3-oxo-4-aza-5α-androst-1-en-17β-carboxamide Crystalline ethanolate Form G (approximately 10 mg) was suspended in 1 mL of water in an agitated vessel. The suspension was allowed to stir for 3 hours. The solids were allowed to settle out. XRPD analysis of the dried solids revealed crystalline crystalline hydrate Form C.

EXAMPLE 5

Crystalline Anhydrous Form D of N-(3H-imidazo[4,5-b]pyridin-2-ylmethyl)-2-fluoro-4-methyl-3-oxo-4-aza-5α-androst-1-en-17β-carboxamide Crystalline tetrahydrate Form E (1.5 gm) and methanol (15 gm, 19 mL) was charged into a 125 mL jacketed flask equipped with banana blade agitation. The jacket temperatue was set to 20° C. The solids dissolved at 20° C. The mixture was seeded with Form A (30 mg) and allowed to age for 1 hour. Deionized water (DIW) (19 mL) was charged to the jacketed flask over an eight hour period. After approximately 1 mL of DIW was charged, the Form A seed had dissolved. After about 9 mL of DIW was charged, the batch was reseeded with approximately 5 mg of Form A seed. The batch was aged overnight following the initial water charge. Approximately one third of the mixture in the jacketed flask (13 mL) was removed and placed into a covered graduated cylinder. The solids settled out. The liquid portion of the sample in the graduated cylinder was pipeted off and filtered through a Whatman™ filter. The remaining portion of the sample in the graduated cylinder was filtered on a filter pot equipped with a vacuum. The sample was then washed with DIW three times. The filtered wet cake was dried in vacuum oven at 35° C. XRPD analysis of the dried solids revealed crystalline Form A.

4.81 mL of DIW was added to the remaining mixture in the jacketed flask over a 4 hour period. The batch was then allowed to age overnight. Subsequently, approximately one half of the mixture remaining in the jacketed flask (15.4 mL) was placed in a covered graduated cylinder. The solids were allowed to settle out. The liquid portion of the sample in the graduated cylinder was pipeted off and filtered through a Whatman™ filter. The wet solids portion of the sample was filtered on a filter pot equipped with a vacuum. The sample was then washed with DIW three times. The filtered wet cake was dried in a vacuum oven at 35° C. XRPD analysis of the dried solids revealed crystalline Form A.

Subsequently, 3.95 mL of DIW was added to the remaining mixture in the jacketed flask over a 4 hour period. The batch was aged for four hours. The agitation was turned off and the solids were allowed to settle out. The liquid portion of the sample in the graduated cylinder was pipeted off and filtered through a Whatman™ filter. The wet solids were filtered on a filter pot equipped with a vacuum. The sample was then washed with DIW three times. The filtered wet cake was dried in a vacuum oven at 35° C. XRPD analysis of the dried solids revealed crystalline anhydrous Form D.

EXAMPLE 6

Crystalline Tetrahydrate Form E of N-(3H-imidazo[4,5-b]pyridin-2-ylmethyl)-2-fluoro-4-methyl-3-oxo-4-aza-5α-androst-1-en-17β-carboxamide Anhydrous crystalline Form A of N-(3H-imidazo[4,5-b]pyridin-2-ylmethyl)-2-fluoro-4-methyl-3-oxo-4-aza-5α-androst-1-en-17β-carboxamide (52.46 mg) was weighed out and dissolved in 50 mL of 0.1 N hydrochloric acid with stirring to form a clear solution. After 24 hours, the sample was adjusted to pH 1.5 with several drops of 50% NaOH to encourage precipitation. The solution still did not precipitate out, so 100.25 additional mg of the anhydrous crystalline Form A was added to the solution to encourage precipitation. The solution went mostly clear and then solids began to precipitate out. The sample equilibrated for 4 more days at which time the solids were centrifuged out, filtered, and rinsed with cold water. XRPD analysis of the dried sample revealed chrystalline Tetrahydrate Form E.

EXAMPLE 7

Crystalline Sesquihydrate Form F of N-(3H-imidazo[4,5-b]pyridin-2-ylmethyl)-2-fluoro-4-methyl-3-oxo-4-aza-5α-androst-1-en-17β-carboxamide A portion of anhydrous crystalline Form A of N-(3H-imidazo[4,5-b]pyridin-2-ylmethyl)-2-fluoro-4-methyl-3-oxo-4-aza-5α-androst-1-en-17β-carboxamide as described in Example 2, was vacuum dried at 40 C oven for two hours and an aliquot was removed for analysis while the rest of the sample continued drying overnight. The sample was then removed and also analyzed. Both the 2 hour and overnight vacuum dried samples were characterized by XRPD and determined to be the same: crystalline sesquihydrate Form F.

EXAMPLE 8

Ethanolate Form G of N-(3H-imidazo[4,5-b]pyridin-2-ylmethyl)-2-fluoro-4-methyl-3-oxo-4-aza-5α-androst-1-en-17β-carboxamide (2-1)

The amorphous N-(3H-imidazo[4,5-b]pyridin-2-ylmethyl)-2-fluoro-4-methyl-3-oxo-4-aza-5α-androst-1-en-17β-carboxamide (9.5 gms) (1-7) was dissolved in 75 mL of ethanol at 60° C. The mixture was allowed to cool to room temperature. After two hours, the solid was collected and washed with 25 mL ethanol. The washed solids were allowed to air dry for 24 hours to give a colorless solid. The dried solids were analyzed by XRPD and determined to be of amorphous form.

EXAMPLE 9

Pharmaceutical Composition

As a specific embodiment of this invention, 100 mg of the anhydrous crystalline Form D of N-(3H-imidazo[4,5-b]pyridin-2-ylmethyl)-2-fluoro-4-methyl-3-oxo-4-aza-5α-androst-1-en-17β-carboxamide, is formulated with sufficient finely divided lactose to provide a total amount of 580 to 590 mg to fill a size 0, hard gelatin capsule.

While the foregoing specification teaches the principles of the present invention, with examples provided for the purpose of illustration, it is understood that the practice of the invention encompasses all of the usual variations, adoptions, or modifications, as being within the scope of the following claims and their equivalents.

Assays

In Vitro and In Vivo Assays for SARM Activity Identification of Compounds

The compounds exemplified in the present application exhibited activity in one or more of the following assays.

Hydroxylapatite-Based Radioligand Displacement Assay of Compound Affinity for Endogenously Expressed AR Materials:

Binding Buffer: TEGM (10 mM Tris-HCl, 1 mM EDTA, 10% glycerol, 1 mM beta-mecaptoethanol, 10 mM Sodium Molybdate, pH 7.2)

50% HAP Slurry: Calbiochem Hydroxylapatite, Fast Flow, in 10 mM Tris, pH 8.0 and 1 mM EDTA.

Wash Buffer: 40 mM Tris, pH7.5, 100 mM KCl, 1 mM EDTA and 1 mM EGTA.

95% EtOH

Methyltrienolone, [17α-methyl-$^3$H], (R1881*); NEN NET590

Methyltrienolone (R1881), NEN NLP005 (dissolve in 95% EtOH)

Dihydrotestosterone (DHT) [1,2,4,5,6,7-$^3$H(N)] NEN NET453

Hydroxylapatite Fast Flow; Calbiochem Cat#391947

Molybdate=Molybdic Acid (Sigma, M1651)

MDA-MB453 Cell Culture Media:

| RPMI 1640 (Gibco 11835-055) w/23.8 mM NaHCO$_3$, 2 mM L-glutamine in 500 mL of complete media | Final conc. |
|---|---|
| 10 mL(1M Hepes) | 20 mM |
| 5 mL (200 mM L-glu) | 4 mM |
| 0.5 mL (10 mg/mL human insulin) in 0.01 N HCl Calbiochem#407694-S) | 10 µg/mL |
| 50 mL FBS (Sigma F2442) | 10% |
| 1 mL (10 mg/mL Gentamicin Gibco#15710-072) | 20 µg/mL |

Cell Passaging

Cells (Hall R. E., et al., *European Journal of Cancer*, 30A: 484-490 (1994)) are rinsed twice in PBS, phenol red-free Trypsin-EDTA is diluted in the same PBS 1:10. The cell layers are rinsed with 1× Trypsin, extra Trypsin is poured out, and the cell layers are incubated at 37° C. for ~2 min. The flask is tapped and checked for signs of cell detachment. Once the cells begin to slide off the flask, the complete media is added to kill the trypsin. The cells are counted at this point, then diluted to the appropriate concentration and split into flasks or dishes for further culturing (Usually 1:3 to 1:6 dilution).

Preparation of MDA-MB-453 Cell Lysate

When the MDA cells are 70 to 85% confluent, they are detached as described above, and collected by centrifuging at 1000 g for 10 minutes at 4° C. The cell pellet is washed twice with TEGM (10 mM Tris-HCl, 1 mM EDTA, 10% glycerol, 1 mM beta-mercaptoethanol, 10 mM Sodium Molybdate, pH 7.2). After the final wash, the cells are resuspended in TEGM at a concentration of $10^7$ cells/mL. The cell suspension is snap frozen in liquid nitrogen or ethanol/dry ice bath and transferred to −80° C. freezer on dry ice. Before setting up the binding assay, the frozen samples are left on ice-water to just thaw (~1 hr). Then the samples are centrifuged at 12,500 g to 20,000 g for 30 min at 4° C. The supernatant is used to set-up assay right away. If using 50 µL of supernatant, the test compound can be prepared in 50 µL of the TEGM buffer.

Procedure for Multiple Compound Screening

1× TEGM buffer is prepared, and the isotope-containing assay mixture is prepared in the following order: EtOH (2% final concentration in reaction), $^3$H-R1881 or $^3$H-DHT (0.5 nM final Conc. in reaction) and 1×TEGM. [eg. For 100 samples, 200 μL (100×2) of EtOH+4.25 μL of 1:10 $^3$H-R1881 stock+2300 μL (100×23) 1× TEGM]. The compound is serially diluted, e.g., if starting final conc. is 1 μM, and the compound is in 25 μL of solution, for duplicate samples, 75 μL of 4×1 μM solution is made and 3 μL of 100 μM is added to 72 μL of buffer, and 1:5 serial dilution.

25 μL of $^3$H-R1881 trace and 25 μL compound solution are first mixed together, followed by addition of 50 μL receptor solution. The reaction is gently mixed, spun briefly at about 200 rpm and incubated at 4° C. overnight. 100 μL of 50% HAP slurry is prepared and added to the incubated reaction which is then vortexed and incubated on ice for 5 to 10 minutes. The reaction mixture is vortexed twice more to resuspend HAP while incubating reaction. The samples in 96-well format are then washed in wash buffer using The FilterMate™ Universal Harvester plate washer (Packard). The washing process transfers HAP pellet containing ligand-bound expressed receptor to Unifilter-96 GF/B filter plate (Packard). The HAP pellet on the filter plate is incubated with 50 μL of MICROSCINT (Packard) scintillint for 30 minutes before being counted on the TopCount microscintillation counter (Packard). $IC_{50}$s are calculated using R1881 as a reference.

The compound of formula I was tested in the above assay and found to have an $IC_{50}$ value of 1 micromolar or less.

Mammalian Two-Hybrid Assay for the Ligand-Induced Interaction of N-Terminus and C-Terminus Domains of the Androgen Receptor (Agonist Mode: VIRCON)

This assay assesses the ability of AR agonists to induce the interaction between the N-terminal domain (NTD) and C-terminal domain (CTD) of rhAR that reflects the in vivo virilizing potential mediated by activated androgen receptors. The interaction of NTD and CTD of rhAR is quantified as ligand induced association between a Gal4DBD-rh-ARCTD fusion protein and a VP16-rhARNTD fusion protein as a mammalian two-hybrid assay in CV-1 monkey kidney cells.

The day before transfection, CV-1 cells are trypsinized and counted, and then plated at 20,000 cells/well in 96-well plates or larger plates (scaled up accordingly) in DMEM+10% FCS. The next morning, CV-1 cells are cotransfected with pCBB1 (Gal4DBD-rhARLBD fusion construct expressed under the SV40 early promoter), pCBB2 (VP16 -rhAR NTD fusion construct expressed under the SV40 early promoter) and pFR (Gal4 responsive luciferase reporter, Promega) using LIPOFECTAMINE PLUS reagent (GIBCO-BRL) following the procedure recommended by the vendor. Briefly, DNA admixture of 0.05 μg pCBB 1, 0.05 μg pCBB2 and 0.1 μg of pFR is mixed in 3.4 μL OPTI-MEM (GIBCO-BRL) mixed with "PLUS Reagent" (1.6 μL, GIBCO-BRL) and incubated at room temperature (RT) for 15 min to form the pre-complexed DNA.

For each well, 0.4 μL LIPOFECTAMINE Reagent (GIBCO-BRL) is diluted into 4.6 μL OPTI-MEM in a second tube and mixed to form the diluted LIPO-FECTAMINE Reagent. The pre-complexed DNA (above) and the diluted LIPOFECTAMINE Reagent (above) are combined, mixed and incubated for 15 minutes at room temperature. The medium on the cells is replaced with 40 μL/well OPTI-MEM, and 10 μL DNA-lipid complexes are added to each well. The complexes are mixed into the medium gently and incubated at 37° C. at 5% $CO_2$ for 5 hours. Following incubation, 200 μL/well D-MEM and 13% charcoal-stripped FCS are added, followed by incubation at 37° C. at 5% $CO_2$. After 24 hours, the test compounds are added at the desired concentration(s) (1 nM-10 μM). Forty eight hours later, luciferase activity is measured using LUC-Screen system (TROPIX) following the manufacturer's protocol. The assay is conducted directly in the wells by sequential addition of 50 μL each of assay solution 1 followed by assay solution 2. After incubation for 40 minutes at room temperature, luminescence is directly measured with 2-5 second integration.

Activity of test compounds is calculated as the $E_{max}$ relative to the activity obtained with 3 nM R1881. The tissue-selective androgen receptor modulator of the present invention display weak or no agonist activity in this assay with less than 50% agonist activity at 10 micromolar.

See He B, Kemppainen J A, Voegel J J, Gronemeyer H, Wilson E M, "Activation function in the human androgen receptor ligand binding domain mediates inter-domain communication with the NH(2)-terminal domain," J. Biol. Chem. 274: 37219-37225 (1999).

Trans-Activation Modulation of Androgen Receptor (TAMAR)

This assay assesses the ability of test compounds to control transcription from the MMTV-LUC reporter gene in MDA-MB-453 cells, a human breast cancer cell line that naturally expresses the human AR. The assay measures induction of a modified MMTV LTR/promoter linked to the LUC reporter gene.

20,000 to 30,000 cells/well are plated in a white, clear-bottom 96-well plate in "Exponential Growth Medium" which consists of phenol red-free RPMI 1640 containing 10%FBS, 4 mM L-glutamine, 20 mM HEPES, 10 ug/mL human insulin, and 20 ug/mL gentamicin. Incubator conditions are 37° C. and 5% $CO_2$. The transfection is done in batch mode. The cells are trypsinized and counted to the right cell number in the proper amount of fresh media, and then gently mixed with the Fugene/DNA cocktail mix and plated onto the 96-well plate. All the wells receive 200 Tl of medium+lipid/DNA complex and are then incubated at 37° C. overnight. The transfection cocktail consists of serum-free Optimem, Fugene6 reagent and DNA. The manufacturer's (Roche Biochemical) protocol for cocktail setup is followed. The lipid (Tl) to DNA (Tg) ratio is approximately 3:2 and the incubation time is 20 minutes at room temperature. Sixteen to 24 hrs after transfection, the cells are treated with test compounds such that the final DMSO (vehicle) concentration is <3%. The cells are exposed to the test compounds for 48 hours. After 48 hours, the cells are lysed by a Promega cell culture lysis buffer for 30-60 minutes and then the luciferase activity in the extracts is assayed in the 96-well format luminometer.

Activity of test compounds is calculated as the $E_{max}$ relative to the activity obtained with 100 nM R1881. See R. E. Hall, et al., "MDA-MB-453, an androgen-responsive human breast carcinoma cell line with high androgen receptor expression," Eur. J. Cancer, 30A: 484-490 (1994) and R. E. Hall, et al., "Regulation of androgen receptor gene expression by steroids and retinoic acid in human breast-cancer cells," Int. J. Cancer., 52: 778-784 (1992). The tissue selective androgen receptor modulator of the present invention displays partial agonist activity in this assay of greater than 10%.

In Vivo Prostate Assay

Male Sprague-Dawley rats aged 9-10 weeks, the earliest age of sexual maturity, are used in prevention mode. The goal is to measure the degree to which androgen-like compounds delay the rapid deterioration (~–85%) of the ventral prostate gland and seminal vesicles that occurs during a seven day period after removal of the testes (orchiectomy [ORX]).

Rats are orchiectomized (ORX). Each rat is weighed, then anesthetized by isoflurane gas that is maintained to effect. A 1.5 cm anteroposterior incision is made in the scrotum. The right testicle is exteriorized. The spermatic artery and vas deferens are ligated with 4.0 silk 0.5 cm proximal to the testicle. The testicle is freed by one cut of a small surgical scissors distal to the ligation site. The tissue stump is returned to the scrotum. The same is repeated for the left testicle. When both stumps are returned to the scrotum, the scrotum and overlying skin are sutured closed with 4.0 silk. For Sham-ORX, all procedures excepting ligation and scissors cutting are completed. The rats fully recover consciousness and full mobility within 10-15 minutes.

A dose of test compound is administered subcutaneously or orally to the rat immediately after the surgical incision is sutured. Treatment continues for an additional six consecutive days.

Necropsy and Endpoints

The rat is first weighed, then anesthetized in a $CO_2$ chamber until near death. Approximately 5 ml whole blood is obtained by cardiac puncture. The rat is then examined for certain signs of death and completeness of ORX. Next, the ventral portion of the prostate gland is located and blunt dissected free in a highly stylized fashion. The ventral prostate is blotted dry for 3-5 seconds and then weighed (VPW). Finally, the seminal vesicle is located and dissected free. The ventral seminal vesicle is blotted dry for 3-5 seconds and then weighed (SVWT).

Primary data for this assay are the weights of the ventral prostate and seminal vesicle. Secondary data include serum LH (luteinizing hormone) and FSH (follicle stimulating hormone), and possible serum markers of bone formation and virilization. Data are analyzed by ANOVA plus Fisher PLSD post-hoc test to identify intergroup differences. The extent to which test compounds inhibit ORX-induced loss of VPW and SVWT is assessed.

In Vivo Bone Formation Assay:

Female Sprague-Dawley rats aged 7-10 months are used in treatment mode to simulate adult human females. The rats have been ovariectomized (OVX) 75-180 days previously, to cause bone loss and simulate estrogen deficient, osteopenic adult human females. Pre-treatment with a low dose of a powerful anti-resorptive, alendronate (0.0028mpk SC, 2×/wk) is begun on Day 0. On Day 15, treatment with test compound is started. Test compound treatment occurs on Days 15-31 with necropsy on Day 32. The goal is to measure the extent to which androgen-like compounds increase the amount of bone formation, shown by increased fluorochrome labeling, at the periosteal surface.

In a typical assay, nine groups of seven rats each are studied. On Days 19 and 29 (fifth and fifteenth days of treatment), a single subcutaneous injection of calcein (8 mg/kg) is given to each rat.

Necropsy and Endpoints

The rat is first weighed, then anesthetized in a $CO_2$ chamber until near death. Approximately 5 mL whole blood is obtained by cardiac puncture. The rat is then examined for certain signs of death and completeness of OVX. First, the uterus is located, blunt dissected free in a highly stylized fashion, blotted dry for 3-5 seconds and then weighed (UW). The uterus is placed in 10% neutral-buffered formalin. Next, the right leg is disarticulated at the hip. The femur and tibia are separated at the knee, substantially defleshed, and then placed in 70% ethanol.

A 1-cm segment of the central right femur, with the femoral proximal-distal midpoint ats center, is placed in a scintillation vial and dehydrated and defatted in graded alcohols and acetone, then introduced to solutions with increasing concentrations of methyl methacrylate. It is embedded in a mixture of 90% methyl methacrylate: 10% dibutyl phthalate that is allowed to polymerize over a 48-72 hours period. The bottle is cracked and the plastic block is trimmed into a shape that conveniently fits the vice-like specimen holder of a Leica 1600 Saw Microtome, with the long axis of the bone prepared for cross-sectioning. Three cross-sections of 85 µm thickness are prepared and mounted on glass slides. One section from each rat that approximates the midpoint of the bone is selected and blind-coded. The periosteal surface of each section is assessed for total periosteal surface, single fluorochrome label, double fluorochrome label, and interlabel distance.

Primary data for this assay are the percentage of periosteal surface bearing double label and the mineral apposition rate (interlabel distance (µm)/10 d), semi-independent markers of bone formation. Secondary data include uterus weight and histologic features. Tertiary endpoints can include serum markers of bone formation and virilization. Data are analyzed by ANOVA plus Fisher PLSD post-hoc test to identify intergroup differences. The extent to which test compounds increase bone formation endpoints are assessed.

What is claimed is:

1. An anhydrous crystalline Form A of N-(3H-imidazo[4,5-b]pyridin-2-ylmethyl)-2-fluoro-4-methyl-3-oxo-4-aza-5-alpha-androst-1-en-17-beta-carboxamide having an X-ray powder diffraction pattern with diffraction peaks at 2-theta values of 5.6±0.1, 7.6±0.1, and 9.6±0.1.

2. An anhydrous crystalline Form A of N-(3H-imidazo[4,5-b]pyridin-2-ylmethyl)-2-fluoro-4-methyl-3-oxo-4-aza-5-alpha-androst-1-en-17-beta-carboxamide according to claim 1 having a carbon-13 CPMAS NMR spectrum signal with chemical shift values of about 39.7±0.1, 118.3±0.1, 169.2±0.1, and 12.6±0.1 p.p.m.

3. An anhydrous crystalline Form A of N-(3H-imidazo[4,5-b]pyridin-2-ylmethyl)-2-fluoro-4-methyl-3-oxo-4-aza-5-alpha-androst-1-en-17-beta-carboxamide according to claim 1 having a fluorine-19 MAS NMR spectrum signal with chemical shift value of about –128.9±0.1 p.p.m.

4. An anhydrous crystalline Form A of claim 1, having a melting point at about 281.2° C.

5. A hygroscopic crystalline Form B of N-(3H-imidazo[4,5-b]pyridin-2-ylmethyl)-2-fluoro-4-methyl-3-oxo-4-aza-5-alpha-androst-1-en-17-beta-carboxamide having a XRPD pattern with diffraction peaks at 2-theta values of about 7.8±0.1, 8.5±0.1, and 10.2±0.1.

6. A hygroscopic crystalline Form B of claim 5, having a melting point at about 164.0° C.

7. A crystalline hydrate Form C of N-(3H-imidazo[4,5-b]pyridin-2-ylmethyl)-2-fluoro-4-methyl-3-oxo-4-aza-5-alpha-androst-1-en-17-beta-carboxamide having a XRPD pattern with diffraction peaks at 2-theta values of about 10.1±0.1, 11.0±0.1, and 12.4±01.

8. A crystalline hydrate Form C of claim 7, further having a melting/decomposition endotherm at about 268.0° C.

9. An anhydrous crystalline Form D of N-(3H-imidazo[4,5-b]pyridin-2-ylmethyl)-2-fluoro-4-methyl-3-oxo-4-aza-5-alpha-androst-1-en-17-beta-carboxamide having a XRPD pattern with diffraction peaks at 2-theta values of about 8.9±0.1, 9.9±0.1, and 12.5±0.1.

10. An anhydrous crystalline Form D of N-(3H-imidazo[4,5-b]pyridin-2-ylmethyl)-2-fluoro-4-methyl-3-oxo-4-aza-5-alpha-androst-1-en-17-beta-carboxamide according to claim 9 having a carbon-13 CPMAS NMR spectrum signal with chemical shift values of about 174.2±0.1, 12.2±0.1, 56.0±0.1, and 23.9±0.1 p.p.m.

11. A crystalline hydrate Form D of claim 9 further having a melting endotherm at about 263.6° C.

12. A crystalline tetrahydrate Form E of N-(3H-imidazo[4,5-b]pyridin-2-ylmethyl)-2-fluoro-4-methyl-3-oxo-4-aza-5-alpha-androst-1-en-17-beta-carboxamide having a XRPD pattern with diffraction peaks at 2-theta values of about 6.1±0.1, 12.8±0.1, and 13.1±0.1.

13. A crystalline tetrahydrate Form E of N-(3H-imidazo[4,5-b]pyridin-2-ylmethyl)-2-fluoro-4-methyl-3-oxo-4-aza-5-alpha-androst-1-en-17-beta-carboxamide according to claim 12 having a carbon-13 CPMAS NMR spectrum signal with chemical shift values of about 13.1±0.1, 28.9±0.1, 39.3.0±0.1, and 154.2±0.1 p.p.m.

14. A crystalline tetrahydrate Form E of N-(3H-imidazo[4,5-b]pyridin-2-ylmethyl)-2-fluoro-4-methyl-3-oxo-4-aza-5-alpha-androst-1-en-17-beta-carboxamide according to claim 12 having a fluorine-19 MAS NMR spectrum signal with chemical shift value of about −126.5±0.1, −128.0±0.1, and −129.3±0.1 p.p.m.

15. A crystalline sesquihydrate Form F of N-(3H-imidazo[4,5-b]pyridin-2-ylmethyl)-2-fluoro-4-methyl-3-oxo-4-aza-5-alpha-androst-1-en-17-beta-carboxamide having a XRPD pattern with diffraction peaks at 2-theta values of about 6.3±0.1, 7.6±0.1, and 12.5±0.1.

16. A crystalline ethanolate Form G of N-(3H-imidazo[4,5-b]pyridin-2-ylmethyl)-2-fluoro-4-methyl-3-oxo-4-aza-5-alpha-androst-1-en-17-beta-carboxamide having a XRPD pattern with diffraction peaks at 2-theta values of about 8.2±0.1, 10.0±0.1, and 13.4±0.1.

17. A crystalline ethanolate Form G of claim 16, further having a melting endotherm at about 165.9° C.

18. A method of making an anhydrous crystalline form A of compound of N-(3H-imidazo[4,5-b]pyridin-2-ylmethyl)-2-fluoro-4-methyl-3-oxo-4-aza-5-alpha-androst-1-en-17-beta-carboxamide comprising:
    a) dissolving the compound in at least one solvent to form a mixture;
    b) refluxing the mixture until crystallization is complete and solids are formed;
    c) isolating the solids; and
    d) drying the solids.

19. A method according to claim 18, wherein the at least one solvent is selected from 1,2-dimethoxyethane, isopropyl alcohol, isopropyl acetate, and acetone.

20. A method according to claim 19, wherein isolating the solids further comprises filtering of the solids via a vacuum filter and washing the solids with at least one wash solvent selected from 1,2-dimethoxyethane, isopropyl alcohol, isopropyl acetate, and acetone.

21. A method of making a tetrahydrate Form E of N-(3H-imidazo[4,5-b]pyridin-2-ylmethyl)-2-fluoro-4-methyl-3-oxo-4-aza-5-alpha-androst-1-en-17-beta-carboxamide comprising: adding anhydrous crystalline free base Form A into an aqueous solution having a pH of about 2 or less to form a solution; aging the solution to precipitate solids; isolating the solids; and drying the solids.

22. A method of claim 21, wherein the addition of anhydrous crystalline free base Form A is done at room temperature.

23. A method of forming crystalline anhydrous Form D of N-(3H-imidazo[4,5-b]pyridin-2-ylmethyl)-2-fluoro-4-methyl-3-oxo-4-aza-5-alpha-androst-1-en-17-beta-carboxamide comprising: dissolving tetrahydrate Form E in at least one solvent to form a solution; charging at least one antisolvent to the solution until the solution is supersaturated; aging the supersaturated solution to form solids; isolating the solids; and drying the solids.

24. A method of claim 23, wherein the in at least one solvent is chosen from dimethylacetamide, methanol, dimethyl sulfoxide, N,N-Dimethylformamide, and N-Methyl-2-pyrrolidone.

25. A method of claim 24, wherein the at least one antisolvent is chosen from heptane, toluene, cyclohexane, water, acetonitrile, isopropyl acetate, isobutyl acetate and methyl tertiary-butyl ether.

26. A method of claim 25, wherein the at least one solvent is chosen from methanol, dimethyl sulfoxide, and N-Methyl-2-pyrrolidone; and the at least one antisolvent is chosen from water and acetonitrile.

27. A method of claim 26, wherein the aging step optionally includes adding more anti-solvent or cooling the batch until solids form.

28. A method of forming crystalline Sesquihydrate Form F of N-(3H-imidazo[4,5-b]pyridin-2-ylmethyl)-2-fluoro-4-methyl-3-oxo-4-aza-5-alpha-androst-1-en-17-beta-carboxamide comprising vacuum drying tetrahydrate Form E at 40° C. for at least 10 hours.

29. A method of forming crystalline ethanolate Form G of N-(3H-imidazo[4,5-b]pyridin-2-ylmethyl)-2-fluoro-4-methyl-3-oxo-4-aza-5-alpha-androst-1-en-17-beta-carboxamide comprising dissolving amorphous N-(3H-imidazo[4,5-b]pyridin-2-ylmethyl)-2-fluoro-4-methyl-3-oxo-4-aza-5α-androst-1-en-17β-carboxamide in ethanol to form a solution; heating the solution to about 60° C.; aging the solution by cooling the solution to room temperature to precipitate solids; isolating the solids from the solution; and drying the solids.

30. A method of forming hygroscopic crystalline Form B of N-(3H-imidazo[4,5-b]pyridin-2-ylmethyl)-2-fluoro-4-methyl-3-oxo-4-aza-5-alpha-androst-1-en-17-beta-carboxamide comprising dissolving amorphous form of N-(3H-imidazo[4,5-b]pyridin-2-ylmethyl)-2-fluoro-4-methyl-3-oxo-4-aza-5α-androst-1-en-17β-carboxamide in ethanol to form a solution, wherein the ratio of amorphous form to ethanol is about 3:4 on a mass basis; heating the solution to about 60° C.; aging the solution by cooling the solution to room temperature to precipitate solids; isolating the solids from the solution; and drying the solids.

31. A method of forming a crystalline hydrate Form C of N-(3H-imidazo[4,5-b]pyridin-2-ylmethyl)-2-fluoro-4-methyl-3-oxo-4-aza-5-alpha-androst-1-en-17-beta-carboxamide comprising dissolving crystalline ethanolate Form G of N-(3H-imidazo[4,5-b]pyridin-2-ylmethyl)-2-fluoro-4-methyl-3-oxo-4-aza-5α-androst-1-en-17β-carboxamide in water in an agitated vessel to form a solution, wherein the ratio of crystalline ethanolate Form G to water is about 1:100 on a mass basis; aging the solution to precipitate solids; isolating the solids from the solution; and drying the solids.

* * * * *